(12) United States Patent
Kirrane et al.

(10) Patent No.: US 9,000,154 B2
(45) Date of Patent: Apr. 7, 2015

(54) RHO KINASE INHIBITORS

(75) Inventors: Thomas Martin Kirrane, Middlebury, CT (US); Daniel Richard Marshall, Norwalk, CT (US); Robert Sibley, North Haven, CT (US); Roger John Snow, Danbury, CT (US); Fariba Soleymanzadeh, Danbury, CT (US); Ronald John Sorcek, Bethel, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 320 days.

(21) Appl. No.: 13/274,610

(22) Filed: Oct. 17, 2011

(65) Prior Publication Data

US 2012/0270868 A1    Oct. 25, 2012

Related U.S. Application Data

(60) Provisional application No. 61/394,414, filed on Oct. 19, 2010.

(51) Int. Cl.
*C07D 417/14* (2006.01)
*A61K 31/5355* (2006.01)
*C07D 417/12* (2006.01)
*C07D 277/60* (2006.01)

(52) U.S. Cl.
CPC ............ *C07D 417/12* (2013.01); *C07D 277/60* (2013.01); *C07D 417/14* (2013.01)

(58) Field of Classification Search
CPC .................................................... C07D 277/82
USPC ................................ 544/106, 135; 514/233.8
See application file for complete search history.

(56) References Cited

U.S. PATENT DOCUMENTS

| | | | |
|---|---|---|---|
| 6,521,754 B2 * | 2/2003 | Alanine et al. ................ 544/129 |
| 8,093,266 B2 | 1/2012 | Dahmann et al. |
| 2004/0082563 A1 | 4/2004 | Dorsch et al. |
| 2007/0173530 A1 | 7/2007 | deLong et al. |
| 2009/0270359 A1 | 10/2009 | Ito et al. |
| 2010/0041645 A1 | 2/2010 | Dahmann et al. |
| 2010/0227846 A1 | 9/2010 | Ito et al. |
| 2012/0165322 A1 | 6/2012 | Cook et al. |
| 2012/0178752 A1 | 7/2012 | Ginn et al. |
| 2012/0270868 A1 | 10/2012 | Kirrane et al. |

FOREIGN PATENT DOCUMENTS

| | | |
|---|---|---|
| DE | 10112768 A1 | 9/2002 |
| EP | 1256574 A1 | 11/2002 |
| EP | 1403255 A1 | 3/2004 |
| JP | 11130751 A | 5/1999 |
| WO | 9205145 A1 | 4/1992 |
| WO | 9304682 A1 | 3/1993 |
| WO | 9304684 A1 | 3/1993 |
| WO | 0244126 A2 | 6/2002 |
| WO | 03015774 A1 | 2/2003 |
| WO | 2004071448 A2 | 8/2004 |
| WO | 2005051892 A1 | 6/2005 |
| WO | 2006034441 A1 | 3/2006 |
| WO | 2006052542 A2 | 5/2006 |
| WO | 2006129199 A1 | 12/2006 |
| WO | 2007008926 A1 | 1/2007 |
| WO | 2008053319 A1 | 5/2008 |
| WO | 2008083124 A1 | 7/2008 |
| WO | 2008086047 A1 | 7/2008 |
| WO | 2008157330 A1 | 12/2008 |
| WO | 2009027392 A1 | 3/2009 |
| WO | 2009028543 A1 | 3/2009 |
| WO | 2009065131 A1 | 5/2009 |
| WO | 2009119880 A1 | 10/2009 |
| WO | 2012006202 A1 | 1/2012 |
| WO | 2012006203 A1 | 1/2012 |
| WO | 2012054367 A1 | 4/2012 |

OTHER PUBLICATIONS

STN search result, US 6,521,754, Alanine et al. (2003).*
Chen, Jichou, et al; Synthesis of Carboxyphenoxyacetic Acid Derivatives Using Liquid-Liquid Phase Transfer Catalysis; Gaodeng Xuexiao Huaxue Xuebao (1991) vol. 12, No. 9 pp. 1195-1199.
Hoering, Heidi, et al; From Bench to Clinic and Back: Perspective on the 1st IQPC Translational Research Conference; Journal of Translational Medicine (2004) vol. 2, Chapter 44 pp. 1-8.
International Search Report and Written Opinion for PCT/US2008/050014 mailed May 8, 2008.
International Search Report and Written Opinion for PCT/US2011/042507 mailed Oct. 11, 2011.
International Search Report and Written Opinion for PCT/US2011/042508 mailed Oct. 12, 2011.

(Continued)

*Primary Examiner* — Yong Chu
*Assistant Examiner* — Sonya Wright
(74) *Attorney, Agent, or Firm* — Michael P. Morris; Edward S. Lazer

(57) ABSTRACT

The present invention relates to compounds of formula (I):

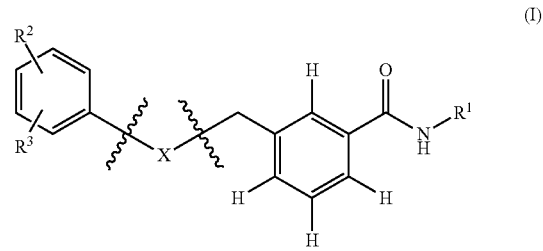

(I)

and pharmaceutically acceptable salts thereof, wherein $R^1$, $R^2$, $R^3$ and X are as defined herein. The invention also relates to pharmaceutical compositions comprising these compounds, methods of using these compounds in the treatment of various diseases and disorders, processes for preparing these compounds and intermediates useful in these processes.

11 Claims, No Drawings

(56) References Cited

OTHER PUBLICATIONS

International Search Report and Written Opinion for PCT/US2011/056505 mailed Dec. 23, 2011.

Loirand, Gervaise, et al; Rho Kinases in Cardiovasculasr Physiology and Phathophysiology; Circulation Research (2006) vol. 98 pp. 322-334.

Lorthioir, Olivier, et al; Single Bead Characterization Using Analytical Constructs: Application to Quality Control of Libraries; Analytical Chemistry (2001) vol. 73 pp. 963-970.

Morwick, Tina, et al; Hit to Lead Account of the Discovery of Bisbenzamide and Related Ureidobenzamide inhibitors of Rho Kinase; Journal of Medicinal Chemistry (2010) vol. 53 pp. 759-777.

Schaefer, Stefan, et al; Failure is an Option: Learning From Unsuccessfull Proof-Of-Concept Trials; Drug Discovery Today (2008) vol. 13, No. 21/22 pp. 913-916.

Tawara, Shunsuke, et al; Progress of the Study of Rho-Kinase and Future Perspective of the Inhibitor; Yakugarku Zasshi (2007) vol. 127, No. 3 Abstract p. 501.

* cited by examiner

RHO KINASE INHIBITORS

FIELD OF THE INVENTION

This invention relates to substituted amide derivatives which are useful as inhibitors of Rho kinase and are thus useful for treating a variety of diseases and disorders that are mediated or sustained through the activity of Rho kinase, including cardiovascular diseases, cancer, neurological diseases, renal diseases, bronchial asthma, erectile dysfunction, and glaucoma. This invention also relates to pharmaceutical compositions comprising these compounds, methods of using these compounds in the treatment of various diseases and disorders, processes for preparing these compounds and intermediates useful in these processes.

BACKGROUND

Rho-Kinase (ROCK) is a member of the serine-threonine protein kinase family. ROCK exists in two isoforms, ROCK1 and ROCK2 (T. Ishizaki et al., EMBO J., 1996, 15, 1885-1893). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (K. Riento and A. J. Ridley, Nat Rev Mol Cell Biol, 2003, 4, 446-56). It is also directly involved in regulating smooth muscle contraction (A. P. Somlyo, Nature, 1997, 389, 908-911). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the RhoA/ROCK signaling pathway plays an important role in signal transduction initiated by several vasoactive factors, for example angiotensin II (T. Yamakawa et al., Hypertension, 2000, 35, 313-318), urotensin II (V. Sauzeau et al., Circ. Res., 2001, 88, 1102-1104), endothelin-1 (P. Tangkijvanich et al., Hepatology, 2001, 33, 74-80), serotonin (H. Shimokawa, Jpn. Circ. J., 2000, 64, 1-12), norepinephrine (M. C. Martinez, et al., Am. J. Physiol., 2000, 279, H1228-H1238) and platelet-derived growth factor (PDGF) (H. Kishi et al., J. Biochem., 2000, 128, 719-722). Many of these factors are implicated in the pathogenesis of cardiovascular disease.

Additional studies in the literature, some using the known ROCK inhibitors fasudil (T. Asano et al., J. Pharmacol. Exp. Ther., 1987, 241, 1033-1040) or Y-27632 (M. Uehata et al., Nature, 1997, 389, 990-994) further illustrate the link between ROCK and cardiovascular disease. For example, ROCK expression and activity have been shown to be elevated in spontaneously hypertensive rats, suggesting a link to the development of hypertension in these animals (Y. Mukai et al., FASEB J., 2001, 15, 1062-1064). The ROCK inhibitor Y-27632 (M. Uehata et al., Nature, ibid) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Y. Eto et al., Am. J. Physiol. Heart Circ. Physiol., 2000, 278, H1744-H1750). In a similar model, ROCK inhibitor Y-27632 also inhibited neointimal formation in rats (N. Sawada et al., Circulation, 2000, 101, 2030-2033). In a porcine model of IL-1 beta-induced coronary stenosis, long term treatment with the ROCK inhibitor fasudil was shown to progressively reduce coronary stenosis, as well as promote a regression of coronary constrictive remodeling (H. Shimokawa et al., Cardiovascular Res., 2001, 51, 169-177).

Additional investigations suggest that a ROCK inhibitor would be useful in treating other cardiovascular diseases. For example, in a rat stroke model, fasudil was shown to reduce both the infarct size and neurologic deficit (Y. Toshima, Stroke, 2000, 31, 2245-2250). The ROCK inhibitor Y-27632 was shown to improve ventricular hypertrophy and function in a model of congestive heart failure in Dahl salt-sensitive rats (N. Kobayashi et al., Cardiovascular Res., 2002, 55, 757-767).

Other animal or clinical studies have implicated ROCK in additional diseases including coronary vasospasm (H. Shimokawa et al., Cardiovasc. Res., 1999, 43, 1029-1039), cerebral vasospasm (M. Sato et al., Circ. Res., 2000, 87, 195-200), ischemia/reperfusion injury (T. Yada et al., J. Am. Coll. Cardiol., 2505, 45, 599-607), pulmonary hypertension (Y. Fukumoto et al., Heart, 2005, 91, 391-392), angina (H. Shimokawa et al., J. Cardiovasc. Pharmacol., 2002, 39, 319-327), renal disease (S. Satoh et al., Eur. J. Pharmacol., 2002, 455, 169-174) and erectile dysfunction (N. F. Gonzalez-Cadavid and J. Rajifer, Endocrine, 2004, 23, 167-176).

In another study, it has been demonstrated that inhibition of the RhoA/ROCK signaling pathway allows formation of multiple competing lamellipodia that disrupt the productive migration of monocytes (R. A. Worthylake et al. The Journal of Biol. Chem., 2003, 278, 13578-13584). It has also been reported that small molecule inhibitors of Rho Kinase are capable of inhibiting MCP-1 mediated chemotaxis in vitro (H. Iijima, Biorganic and Medicinal Chemistry, 2007, 15, 1022-1033). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (H. Shimokawa et al., Arterioscler. Thromb. Vasc. Biol., 2005, 25, 1767-1775). Furthermore, Rho-kinase has been indicated as a drug target for the treatment of various other diseases, including airway inflammation and hyperresponsiveness (P. J. Henry et al., Pulm Pharmacol Ther., 2005, 18, 67-74), cancer (R. Rattan et al., J. Neurosci. Res., 2006, 83, 243-55. D. Lepley et al., Cancer Res., 2005, 65, 3788-95), as well as neurological disorders, such as spinal-cord injury, Alzheimer disease, multiple sclerosis, stroke and neuropathic pain (B. K. Mueller et al., Nat Rev Drug Disc, 2005, 4, 387-398; X. Sun et. al., J. Neuroimmunology, 2006, 180, 126-134).

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in patients with diabetes and hypertension where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, cardiac failure, renal failure and peripheral artery disease.

Although there are many reports of ROCK inhibitors under investigation (see, for example, U.S. 20100041645 A1, U.S. 20080161297 A1 and E. Hu and D. Lee, Expert Opin. Ther. Targets, 2005, 9, 715-736), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, bronchial asthma, erectile dysfunction, and glaucoma.

BRIEF SUMMARY OF THE INVENTION

In a general aspect, the present invention is directed to the compounds of the formula I:

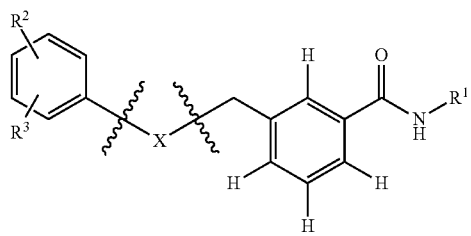

wherein $R^1$, $R^2$, $R^3$ and X are as defined herein, as well as the tautomers and pharmaceutically acceptable salts thereof. It has been found that the compounds of formula I have valuable pharmacological properties, particularly on inhibiting activity of Rho kinase.

In another aspect, the present invention is directed to a method of inhibiting Rho kinase activity in a patient comprising administering to the patient a compound of the present invention as described above.

In another aspect, the present invention is directed to a method for treating a disease or disorder associated with the activation of Rho kinase which method comprises administering to a patient in need of such treatment a compound of the present invention as described above.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, cardiac failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma and glaucoma, which method comprises administering to a patient in need of such treatment a compound of the present invention as described above.

In another aspect, the present invention is directed to a method of treating diseases mediated at least partially by Rho kinase including spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

DETAILED DESCRIPTION OF THE INVENTION

In an embodiment, there are provided compounds of the formula I

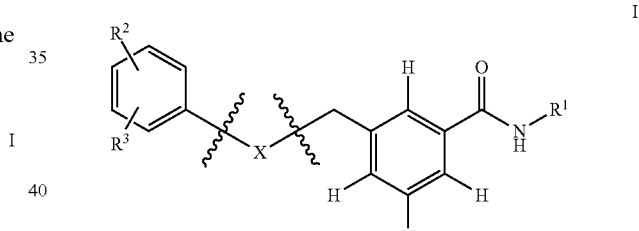

wherein:
X is selected from the group $X^a$ consisting of

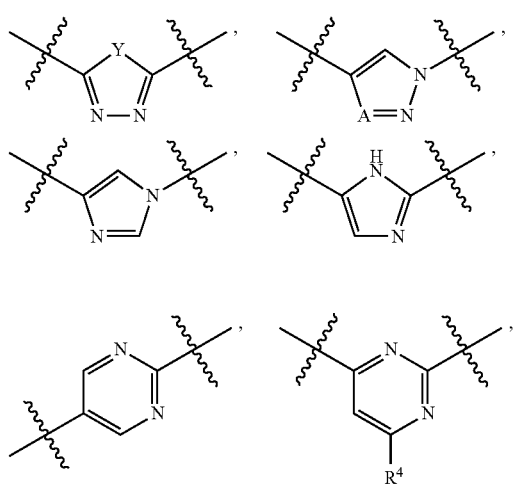

-continued

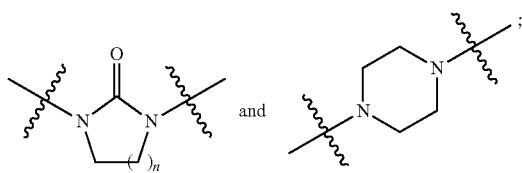

A is C or N;

Y is O or S;

R¹ is selected from the group $R^{1a}$ consisting of

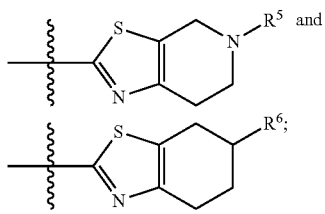

$R^2$ and $R^3$ are independently selected from H, —CH₃, —OCH₃, —F, —Cl, —C(O)NH₂, and —CN, provided that $R^2$ and $R^3$ are not both H;

$R^4$ is H or —CH₃;

$R^5$ is $C_{1-6}$alkyl;

$R^6$ is selected from a heterocyclyl group selected from piperidinyl, piperazinyl, morpholinyl, 2,3-dihydroindolyl and pyrrolidinyl, and

—N(R⁷)(R⁸), wherein the heterocyclyl group may be substituted with one to three groups selected from halogen, oxo, $C_{1-3}$alkyl and $C_{3-6}$cycloalkyl;

$R^7$ and $R^8$ are independently selected from H, $C_{1-3}$alkyl, $C_{3-6}$cycloalkyl and $CO_2C_{1-4}$alkyl, wherein the $C_{1-3}$alkyl and $C_{3-6}$cycloalkyl are optionally substituted with —OCH₃, —CF₃, —CHF₂ or —CN; and n is 1 or 2;

or a salt thereof.

In another embodiment, there are provided compounds of formula I as described above wherein:

$R^2$ is selected from 3-CN and 4-CN;

$R^3$ is H; and $R^5$ is —CH₃;

or a salt thereof.

In another embodiment, there are provided compounds of formula I as described in the first embodiment wherein:

$R^1$ is selected from the group $R^{1b}$ consisting of

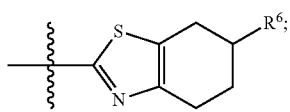

or a salt thereof.

In another embodiment, there are provided compounds of formula I as described in the first embodiment wherein:

$R^1$ is selected from the group $R^{1c}$ consisting of

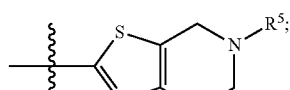

or a salt thereof.

In another embodiment, there are provided compounds of formula I as described in the first embodiment wherein:

X is selected from the group $X^b$ consisting of

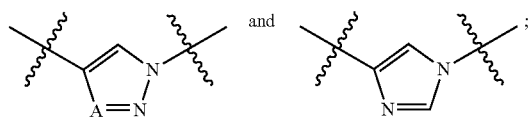

or a salt thereof.

In another embodiment, there are provided compounds of formula I as described in the first embodiment wherein:

X is selected from the group X' consisting of

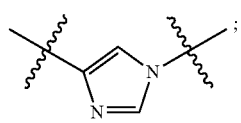 [SMILES: *c1cn(*)cn1]

or a salt thereof.

In another embodiment, there are provided compounds of formula I as described in the first embodiment wherein:

X is selected from the group $X^d$ consisting of

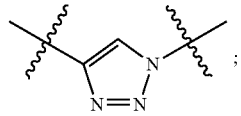 [SMILES: *c1cn(*)nn1]

or a salt thereof.

In another embodiment, there are provided compounds of formula I as described in the first embodiment wherein:

X is selected from the group $X^e$ consisting of

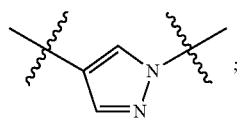 [SMILES: *c1cnn(*)c1]

or a salt thereof.

In another embodiment, there are provided compounds of formula I as described in the first embodiment wherein:

X is selected from the group $X^f$ consisting of

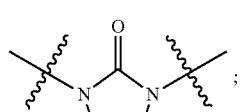

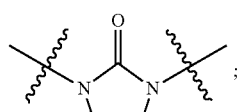

or a salt thereof.

In another embodiment, there are provided compounds of formula I as described in the first embodiment wherein:

X is selected from the group $X^g$ consisting of

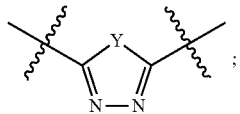

or a salt thereof.

Groups $R^1$ and X may be combined to form additional embodiments. For example further embodiments include compounds of formula I as described in the first embodiment or a salt thereof wherein $R^1$ and X are as shown in the table below:

| Embodiment | $R^1$ | X |
|---|---|---|
| I-a | $R^{1b}$ | $X^c$ |
| I-b | $R^{1b}$ | $X^d$ |
| I-c | $R^{1b}$ | $X^e$ |
| I-d | $R^{1b}$ | $X^f$ |
| I-e | $R^{1b}$ | $X^g$ |
| I-f | $R^{1c}$ | $X^c$ |
| I-g | $R^{1c}$ | $X^d$ |
| I-h | $R^{1c}$ | $X^e$ |
| I-i | $R^{1c}$ | $X^f$ |
| I-j | $R^{1c}$ | $X^g$ |

Still further embodiments would include compounds of formula I as described in the second embodiment or a salt thereof where $R^1$ and X are as shown in the table above.

The following are representative compounds of the invention which can be made by the general synthetic schemes, the examples, and known methods in the art.

TABLE 1

| Cpd Number | Structure |
|---|---|
| 1 | 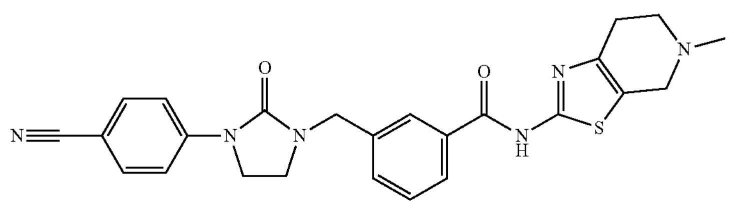 [SMILES: CN1CCc2nc(NC(=O)c3cccc(CN4CCN(c5ccc(C#N)cc5)C4=O)c3)sc2C1] |
| 2 | 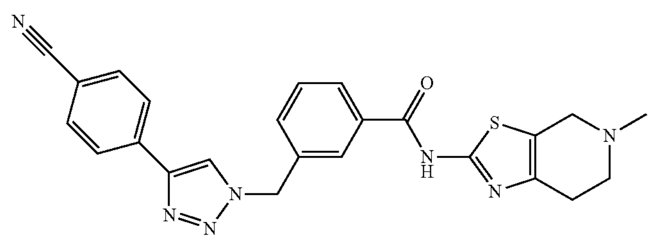 [SMILES: CN1CCc2nc(NC(=O)c3cccc(Cn4cc(-c5ccc(C#N)cc5)nn4)c3)sc2C1] |
| 3 | 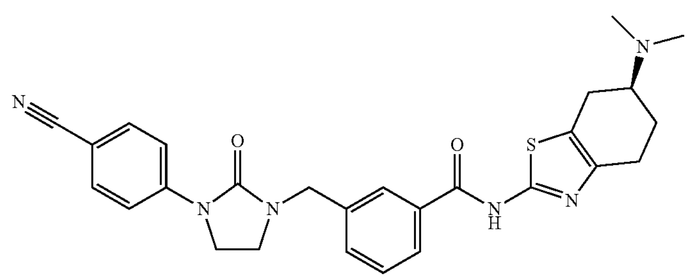 [SMILES: CN(C)[C@H]1CCc2nc(NC(=O)c3cccc(CN4CCN(c5ccc(C#N)cc5)C4=O)c3)sc2C1] |
| 4 | 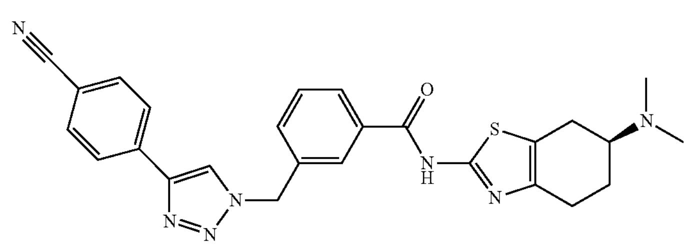 |

TABLE 1-continued
| Cpd Number | Structure |
|---|---|
| 5 | 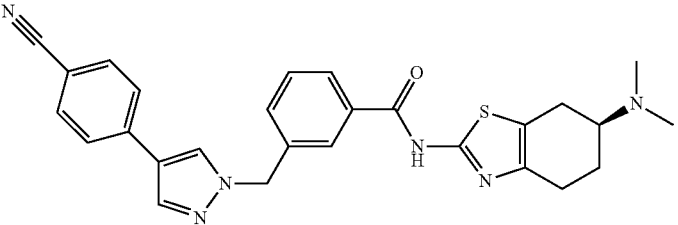 [SMILES: CN(C)[C@H]1CCc2nc(NC(=O)c3cccc(Cn4cc(-c5ccc(C#N)cc5)nn4)c3)sc2C1] |
| 6 | 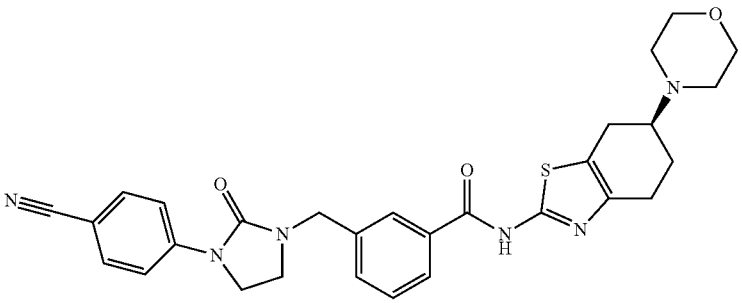 [SMILES: N#Cc1ccc(N2CCN(Cc3cccc(C(=O)Nc4nc5c(s4)C[C@@H](N4CCOCC4)CC5)c3)C2=O)cc1] |
| 7 | 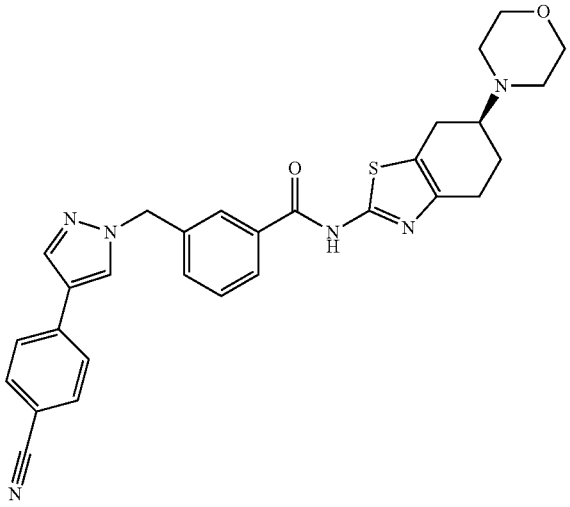 |
| 8 | 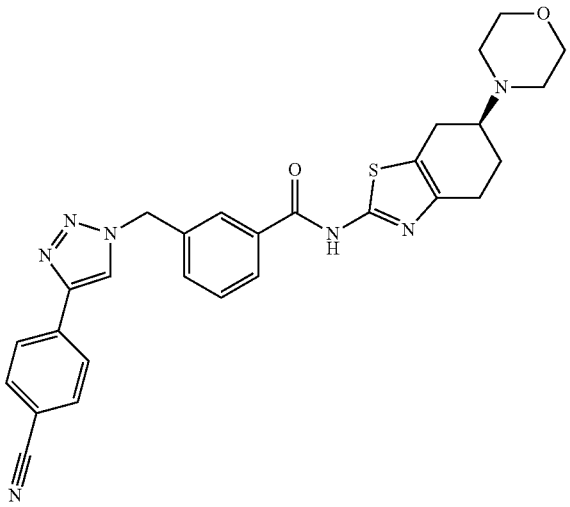 [SMILES: N#Cc1ccc(-c2cn(Cc3cccc(C(=O)Nc4nc5c(s4)C[C@@H](N4CCOCC4)CC5)c3)nn2)cc1] |

TABLE 1-continued
| Cpd Number | Structure |
|---|---|
| 9 | 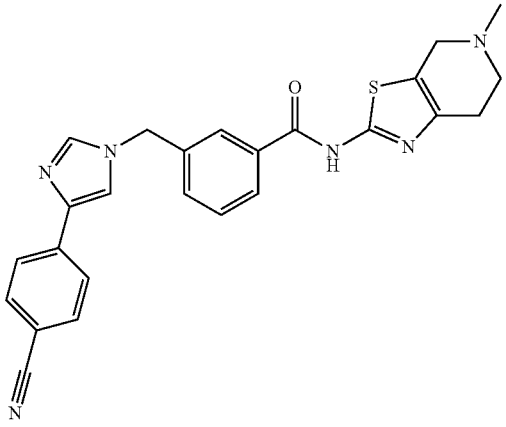 [SMILES: CN1CCc2nc(NC(=O)c3cccc(Cn4cnc(-c5ccc(C#N)cc5)c4)c3)sc2C1] |
| 10 | 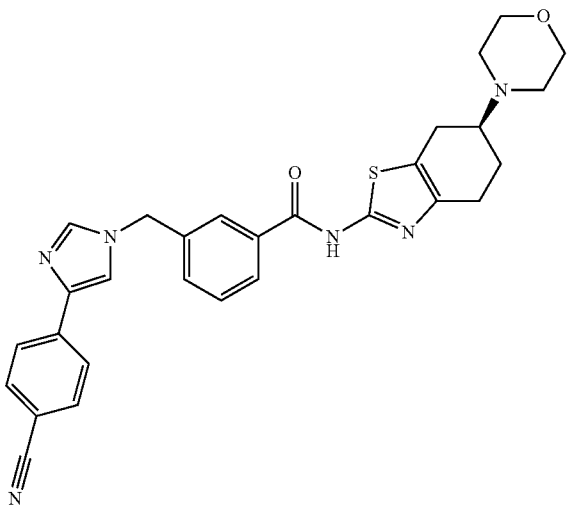 |
| 11 | 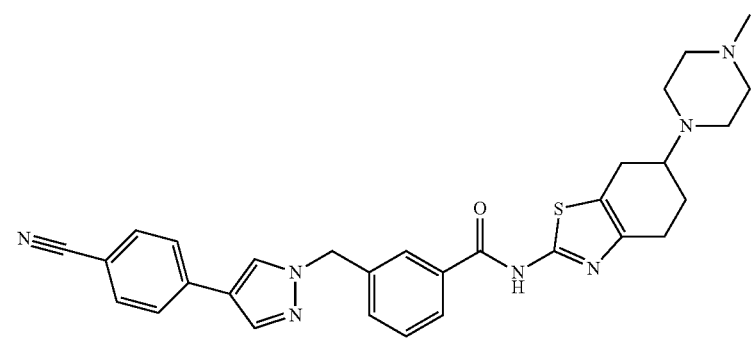 [SMILES: CN1CCN(C2CCc3nc(NC(=O)c4cccc(Cn5cc(-c6ccc(C#N)cc6)cn5)c4)sc3C2)CC1] |

TABLE 1-continued
| Cpd Number | Structure |
|---|---|
| 12 | 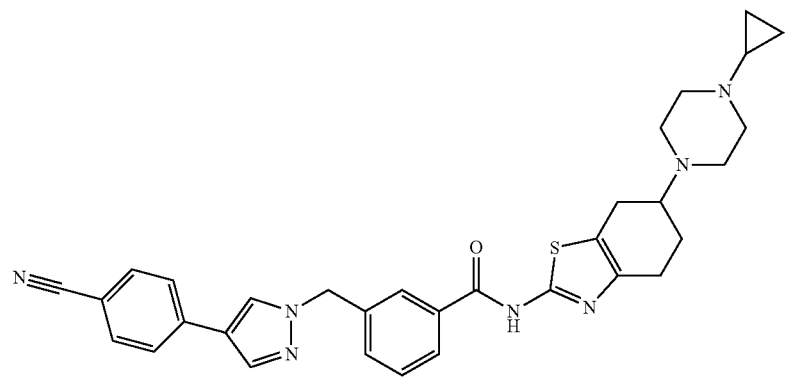 [SMILES: N#Cc1ccc(-c2cnn(Cc3cccc(C(=O)Nc4nc5c(s4)CC(N4CCN(C6CC6)CC4)CC5)c3)c2)cc1] |
| 13 | 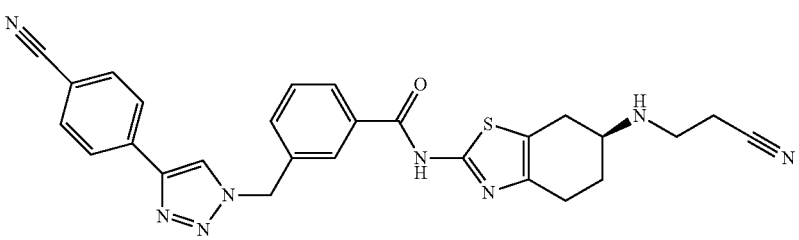 |
| 14 | 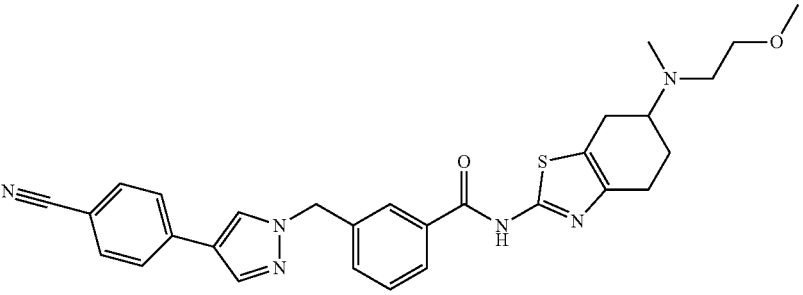 [SMILES: COCCN(C)C1CCc2nc(NC(=O)c3cccc(Cn4cc(-c5ccc(C#N)cc5)cn4)c3)sc2C1] |
| 15 | 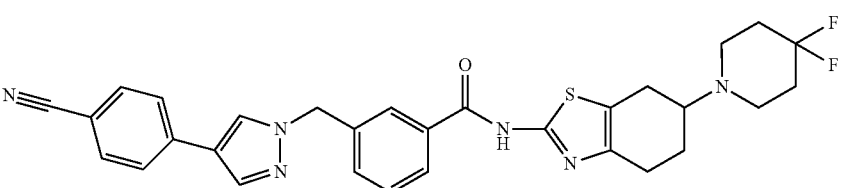 |
| 16 | 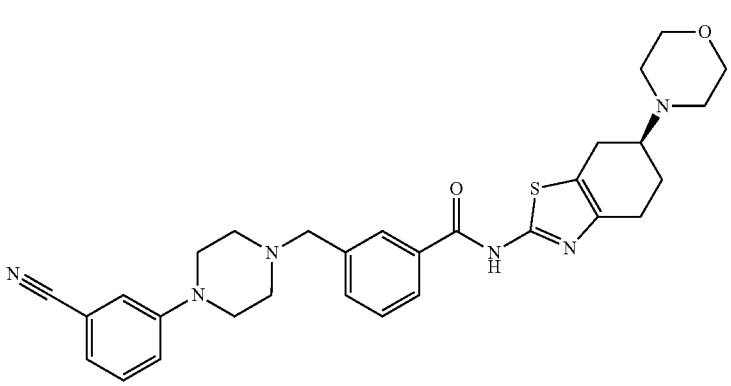 [SMILES: N#Cc1cccc(N2CCN(Cc3cccc(C(=O)Nc4nc5c(s4)C[C@@H](N4CCOCC4)CC5)c3)CC2)c1] |

TABLE 1-continued
| Cpd Number | Structure |
|---|---|
| 17 | 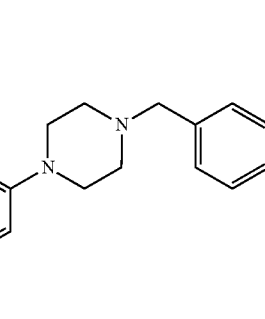 |
| 18 | 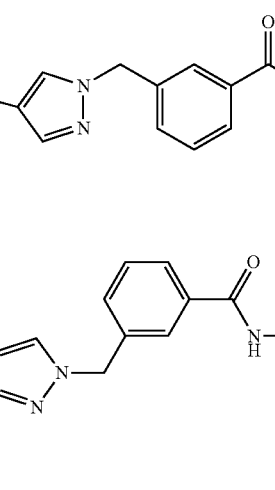 |
| 19 | 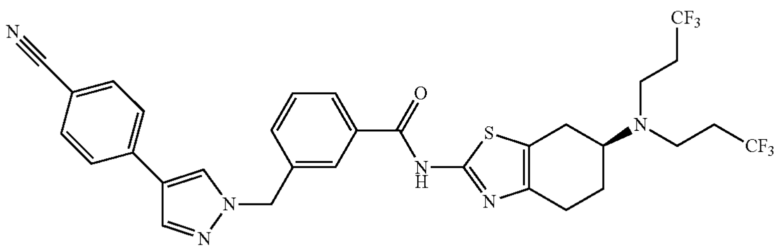 [SMILES: N#Cc1ccc(-c2cnn(Cc3cccc(C(=O)Nc4nc5c(s4)C[C@@H](N(CCC(F)(F)F)CCC(F)(F)F)CC5)c3)c2)cc1] |
| 20 | 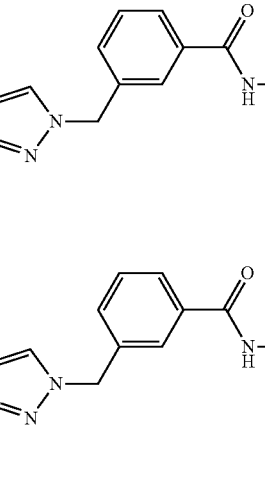 |
| 21 | 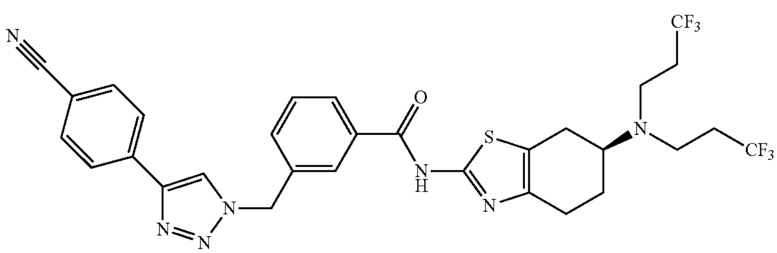 [SMILES: N#Cc1ccc(-c2cn(Cc3cccc(C(=O)Nc4nc5c(s4)C[C@@H](N(CCC(F)(F)F)CCC(F)(F)F)CC5)c3)nn2)cc1] |
| 22 | 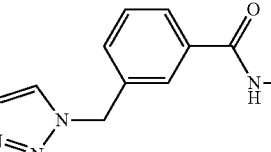 |

TABLE 1-continued

| Cpd Number | Structure |
|---|---|
| 23 | 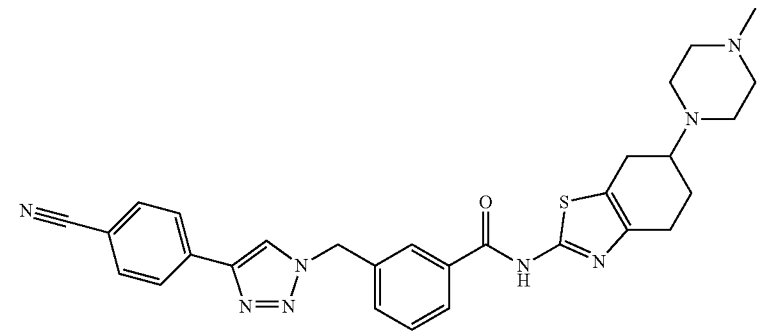 [SMILES: CN1CCN(C2CCc3nc(NC(=O)c4cccc(Cn5cc(-c6ccc(C#N)cc6)nn5)c4)sc3C2)CC1] |
| 24 | 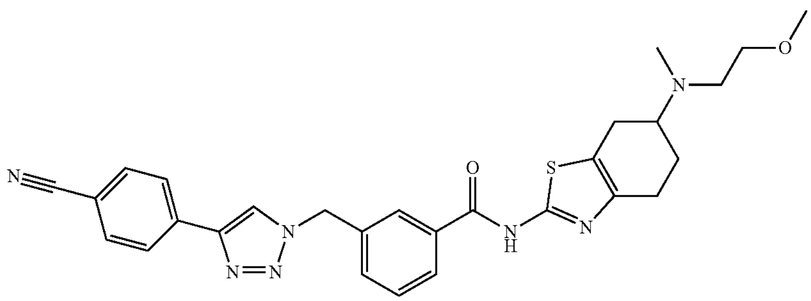 [SMILES: COCCN(C)C1CCc2nc(NC(=O)c3cccc(Cn4cc(-c5ccc(C#N)cc5)nn4)c3)sc2C1] |
| 25 | 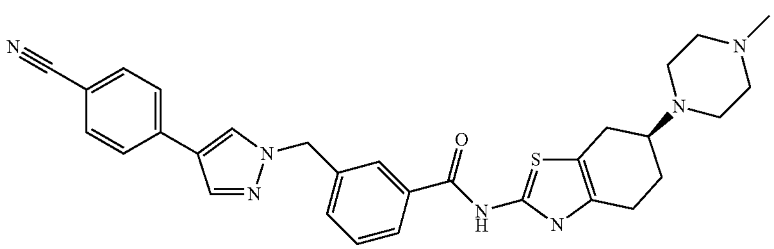 |
| 26 | 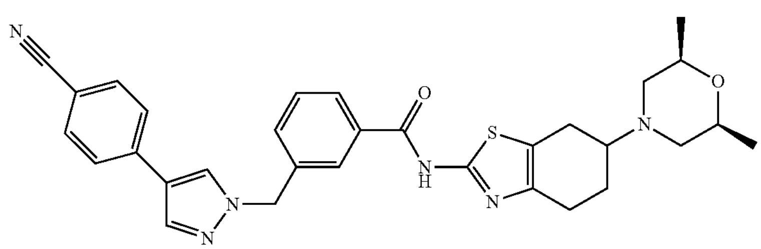 [SMILES: C[C@@H]1CN(C2CCc3nc(NC(=O)c4cccc(Cn5cc(-c6ccc(C#N)cc6)cn5)c4)sc3C2)C[C@H](C)O1] |
| 27 | 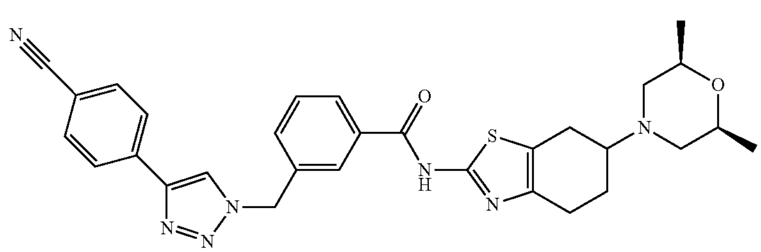 [SMILES: C[C@@H]1CN(C2CCc3nc(NC(=O)c4cccc(Cn5cc(-c6ccc(C#N)cc6)nn5)c4)sc3C2)C[C@H](C)O1] |

TABLE 1-continued
| Cpd Number | Structure |
|---|---|
| 28 | 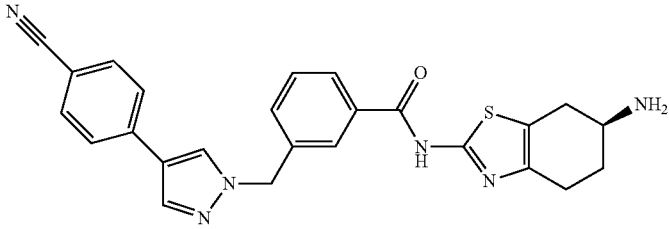 |
| 29 | 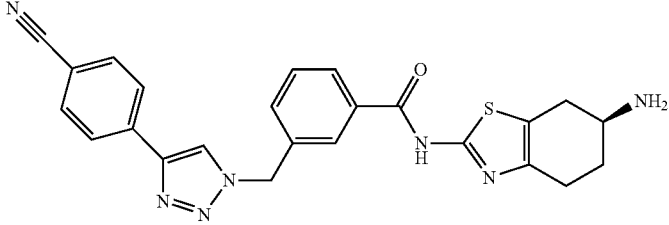 [SMILES: N#Cc1ccc(-c2cn(Cc3cccc(C(=O)Nc4nc5c(s4)C[C@@H](N)CC5)c3)nn2)cc1] |
| 30 | 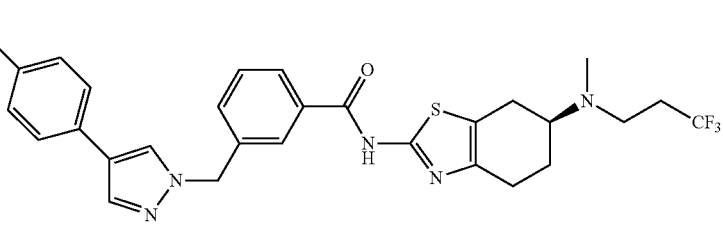 |
| 31 | 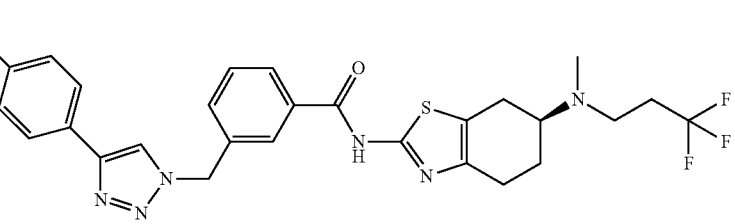 |
| 32 | 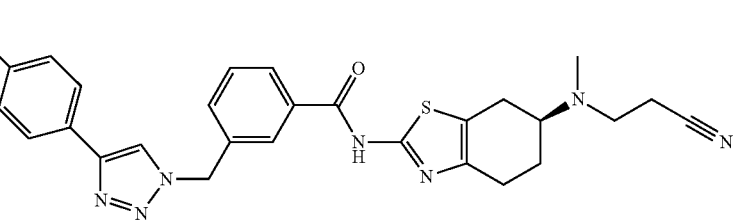 |
| 33 | 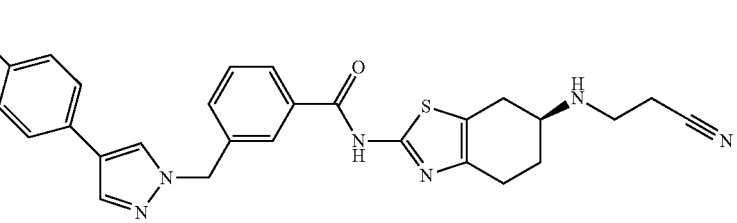 |

TABLE 1-continued
| Cpd Number | Structure |
|---|---|
| 34 | 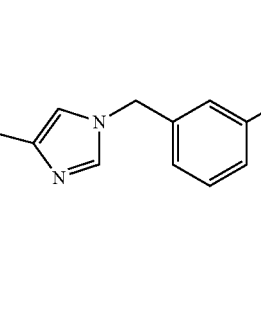 |
| 35 | 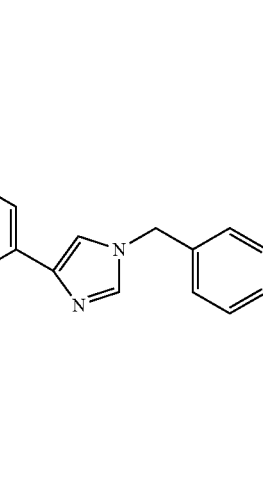 |
| 36 | 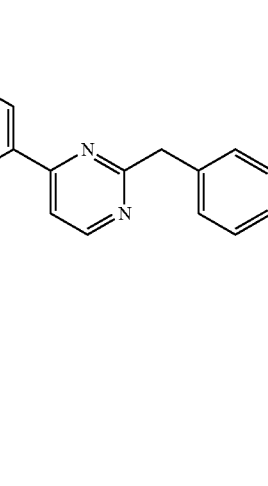 |
| 37 | 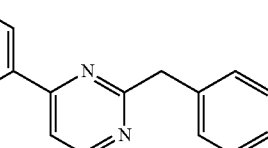 |

TABLE 1-continued

| Cpd Number | Structure |
|---|---|
| 38 | 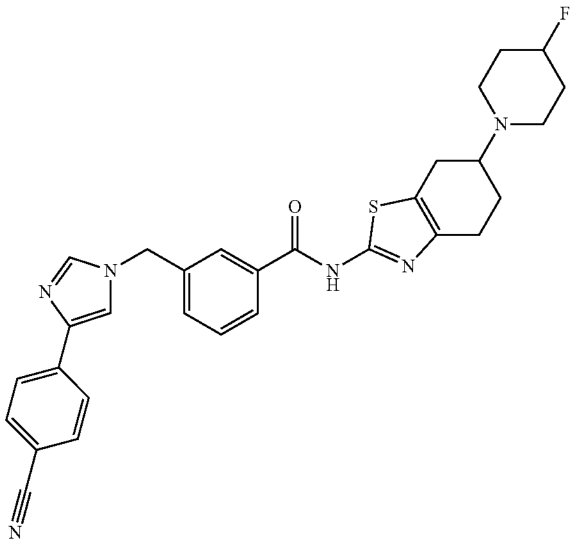 [SMILES: N#Cc1ccc(-c2cn(Cc3cccc(C(=O)Nc4nc5c(s4)CC(N4CCC(F)CC4)CC5)c3)cn2)cc1] |
| 39 | 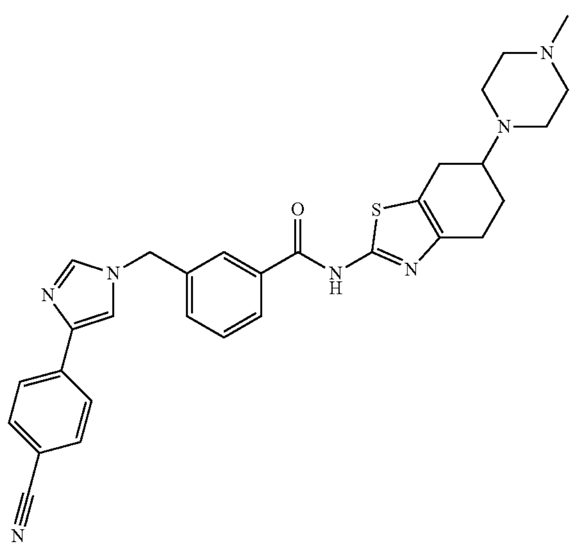 [SMILES: CN1CCN(C2CCc3nc(NC(=O)c4cccc(Cn5cnc(-c6ccc(C#N)cc6)c5)c4)sc3C2)CC1] |
| 40 | 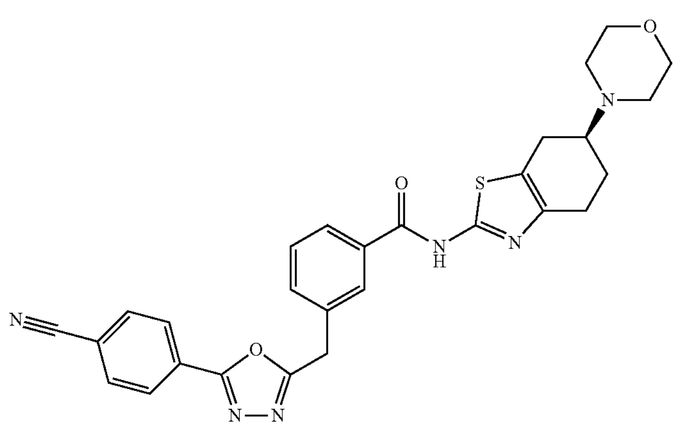 |

TABLE 1-continued

| Cpd Number | Structure |
|---|---|
| 41 | 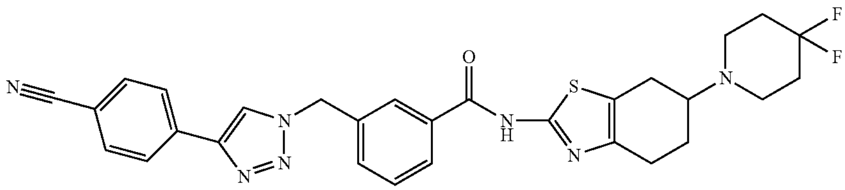 [SMILES: N#Cc1ccc(-c2cn(Cc3cccc(C(=O)Nc4nc5c(s4)CC(N4CCC(F)(F)CC4)CC5)c3)nn2)cc1] |
| 42 | 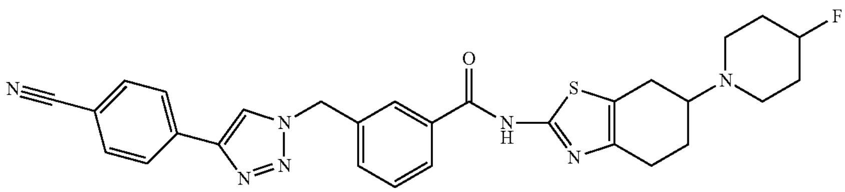 [SMILES: N#Cc1ccc(-c2cn(Cc3cccc(C(=O)Nc4nc5c(s4)CC(N4CCC(F)CC4)CC5)c3)nn2)cc1] |
| 43 | 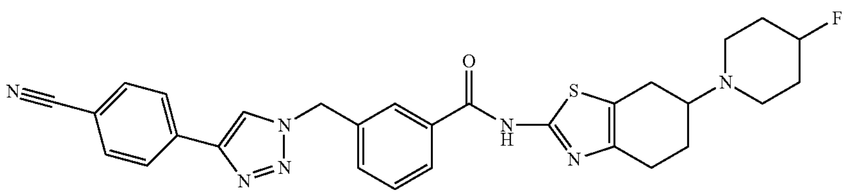 [SMILES: N#Cc1ccc(-c2cn(Cc3cccc(C(=O)Nc4nc5c(s4)CC(N4CCC(F)CC4)CC5)c3)nn2)cc1] |
| 44 | 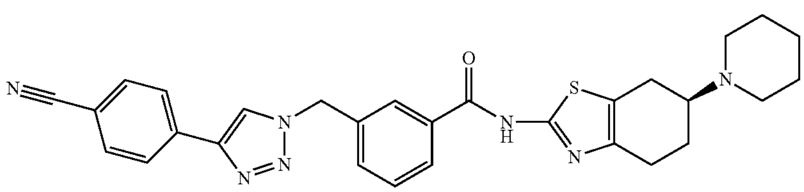 [SMILES: N#Cc1ccc(-c2cn(Cc3cccc(C(=O)Nc4nc5c(s4)C[C@@H](N4CCCCC4)CC5)c3)nn2)cc1] |
| 45 | 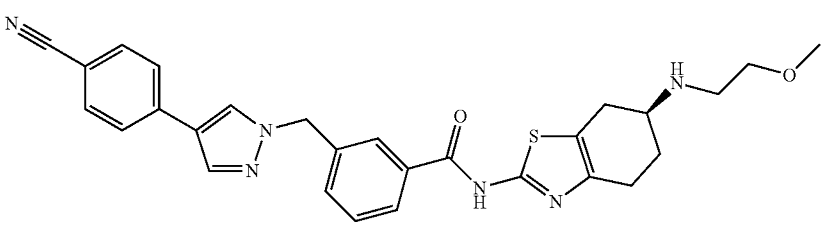 |
| 46 | 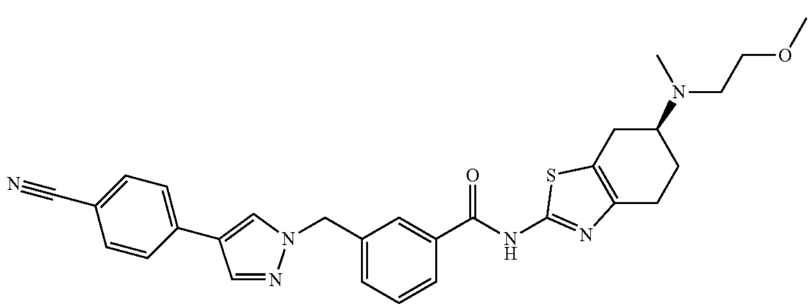 [SMILES: COCCN(C)[C@H]1CCc2nc(NC(=O)c3cccc(Cn4cc(-c5ccc(C#N)cc5)cn4)c3)sc2C1] |

TABLE 1-continued
| Cpd Number | Structure |
|---|---|
| 47 | 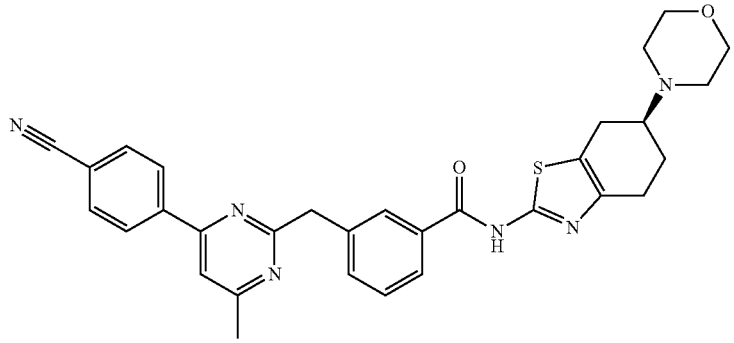 [SMILES: Cc1cc(-c2ccc(C#N)cc2)nc(Cc2cccc(C(=O)Nc3nc4c(s3)C[C@@H](N3CCOCC3)CC4)c2)n1] |
| 48 | 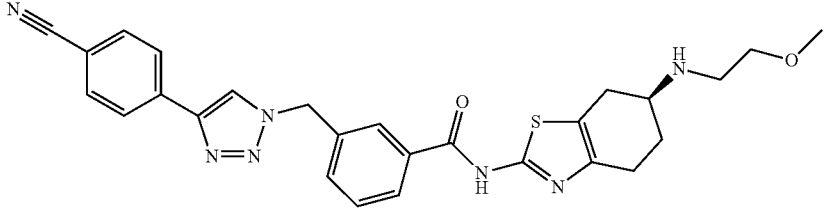 [SMILES: COCCN[C@H]1CCc2nc(NC(=O)c3cccc(Cn4cc(-c5ccc(C#N)cc5)nn4)c3)sc2C1] |
| 49 | 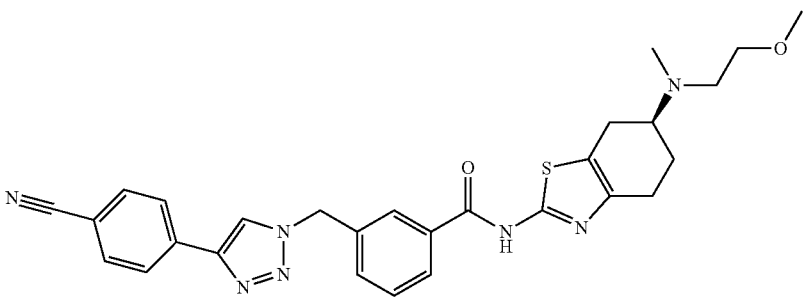 [SMILES: COCCN(C)[C@H]1CCc2nc(NC(=O)c3cccc(Cn4cc(-c5ccc(C#N)cc5)nn4)c3)sc2C1] |
| 50 | 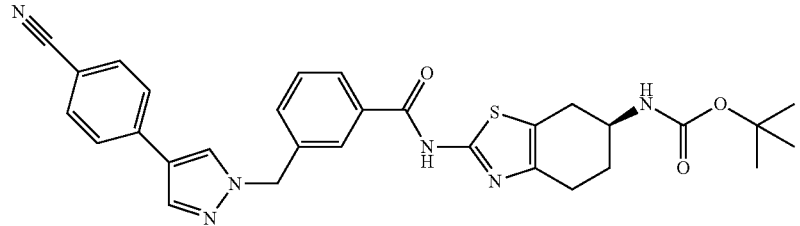 [SMILES: CC(C)(C)OC(=O)N[C@H]1CCc2nc(NC(=O)c3cccc(Cn4cc(-c5ccc(C#N)cc5)cn4)c3)sc2C1] |
| 51 | 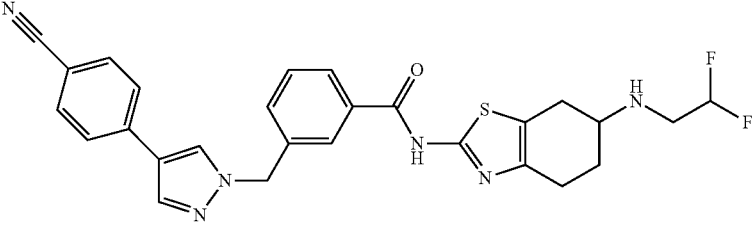 [SMILES: N#Cc1ccc(-c2cnn(Cc3cccc(C(=O)Nc4nc5c(s4)CC(NCC(F)F)CC5)c3)c2)cc1] |
| 52 | 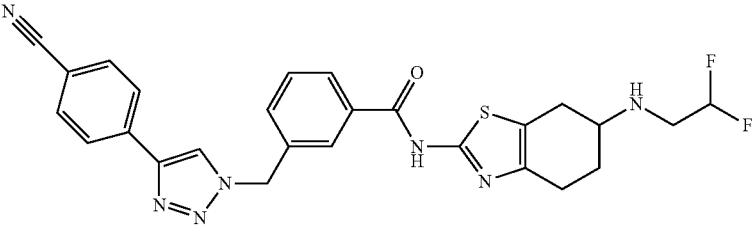 [SMILES: N#Cc1ccc(-c2cn(Cc3cccc(C(=O)Nc4nc5c(s4)CC(NCC(F)F)CC5)c3)nn2)cc1] |

TABLE 1-continued
| Cpd Number | Structure |
|---|---|
| 53 | 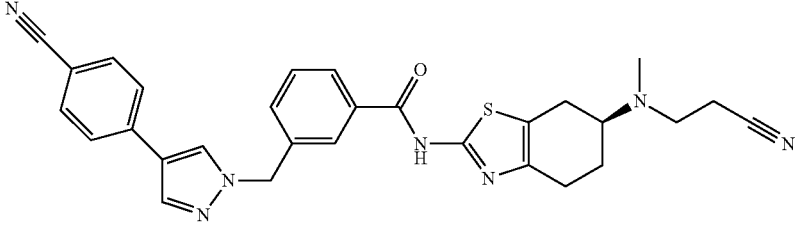 [SMILES: CN(CCC#N)[C@H]1CCc2nc(NC(=O)c3cccc(Cn4cc(-c5ccc(C#N)cc5)cn4)c3)sc2C1] |
| 54 | 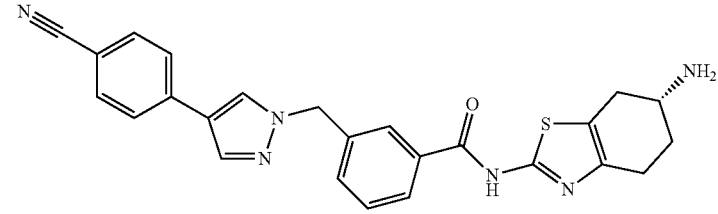 |
| 55 | 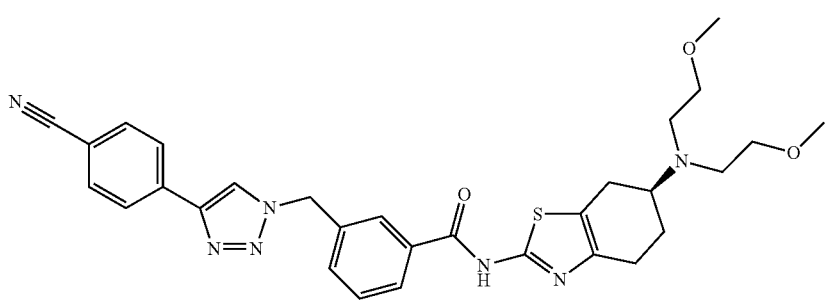 |
| 56 | 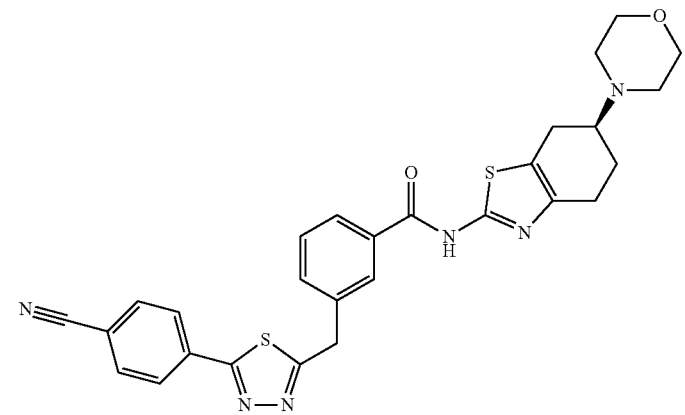 |
| 57 | 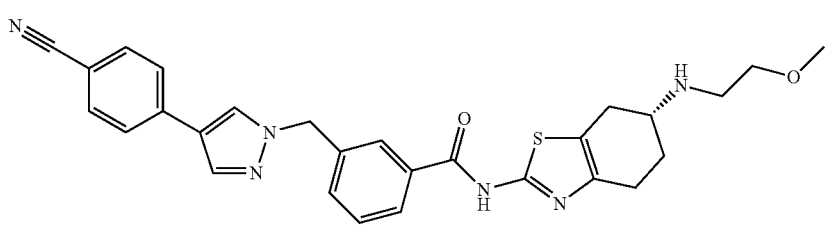 |

TABLE 1-continued

| Cpd Number | Structure |
|---|---|
| 58 | 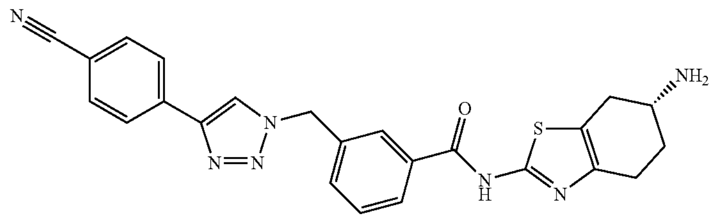 [SMILES: N#Cc1ccc(-c2cnn(Cc3cccc(C(=O)Nc4nc5c(s4)C[C@H](N)CC5)c3)c2)cc1] |
| 59 | 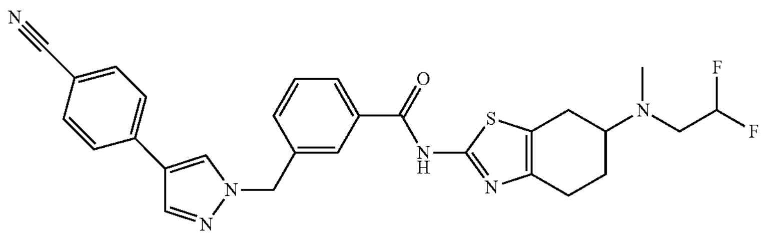 [SMILES: CN(CC(F)F)C1CCc2nc(NC(=O)c3cccc(Cn4cc(-c5ccc(C#N)cc5)cn4)c3)sc2C1] |
| 60 | 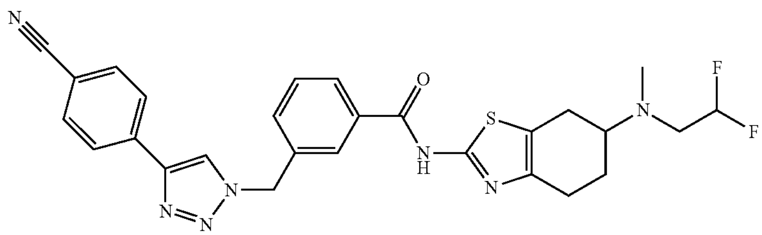 [SMILES: CN(CC(F)F)C1CCc2nc(NC(=O)c3cccc(Cn4cc(-c5ccc(C#N)cc5)nn4)c3)sc2C1] |
| 61 | 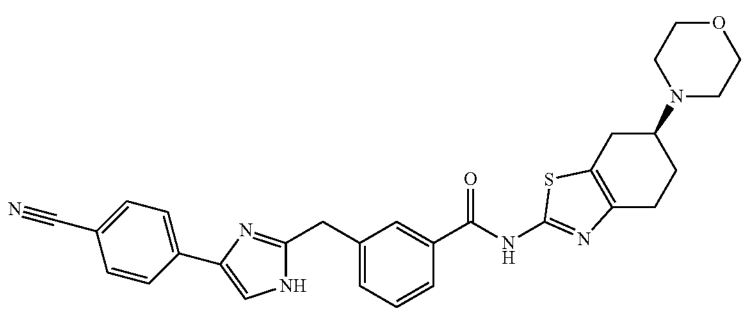 [SMILES: N#Cc1ccc(-c2c[nH]c(Cc3cccc(C(=O)Nc4nc5c(s4)C[C@@H](N4CCOCC4)CC5)c3)n2)cc1] |
| 62 | 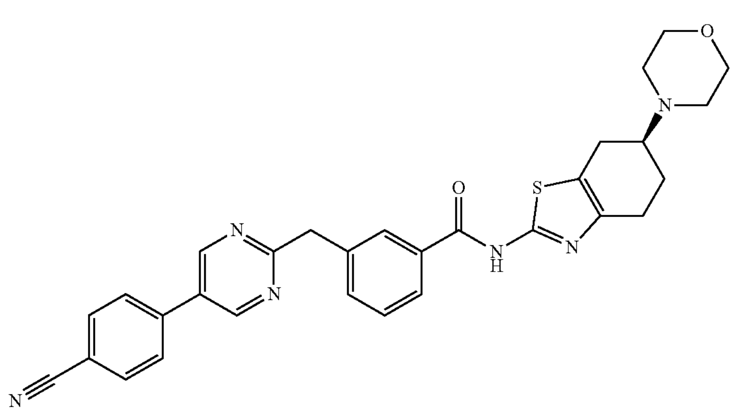 [SMILES: N#Cc1ccc(-c2cnc(Cc3cccc(C(=O)Nc4nc5c(s4)C[C@@H](N4CCOCC4)CC5)c3)nc2)cc1] |

TABLE 1-continued
| Cpd Number | Structure |
|---|---|
| 63 | 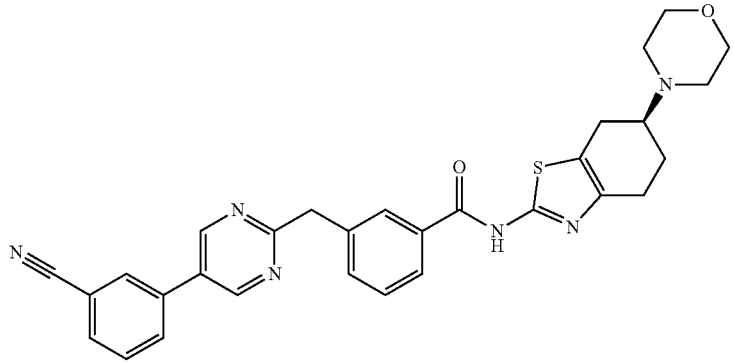 [SMILES: N#Cc1cccc(-c2cnc(Cc3cccc(C(=O)Nc4nc5c(s4)C[C@@H](N4CCOCC4)CC5)c3)nc2)c1] |
| 64 | 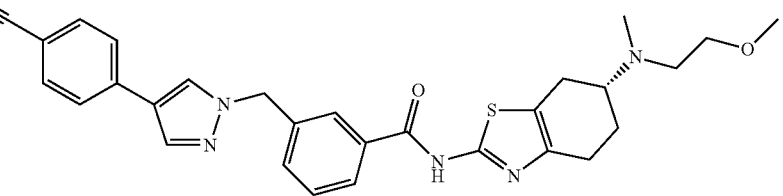 |
| 65 | 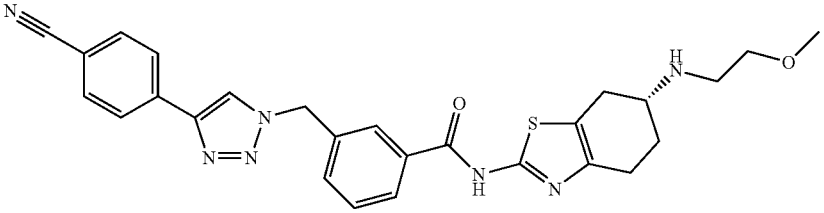 [SMILES: COCCN[C@@H]1CCc2nc(NC(=O)c3cccc(Cn4cc(-c5ccc(C#N)cc5)nn4)c3)sc2C1] |
| 66 | 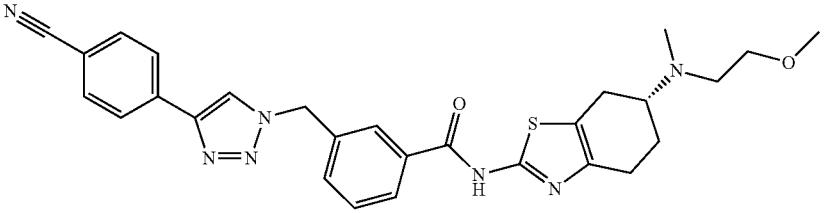 [SMILES: COCCN(C)[C@@H]1CCc2nc(NC(=O)c3cccc(Cn4cc(-c5ccc(C#N)cc5)nn4)c3)sc2C1] |
| 67 | 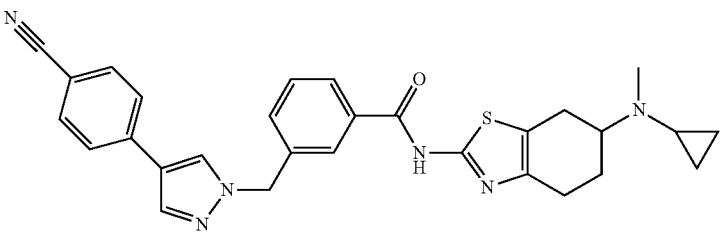 |
| 68 | 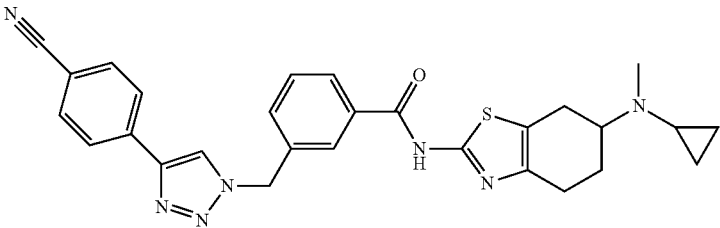 [SMILES: CN(C1CC1)C1CCc2nc(NC(=O)c3cccc(Cn4cc(-c5ccc(C#N)cc5)cn4)c3)sc2C1] |

TABLE 1-continued
| Cpd Number | Structure |
|---|---|
| 69 | 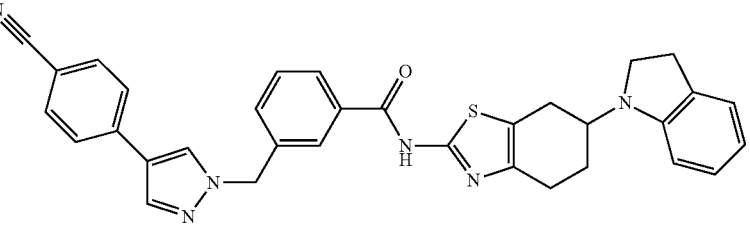 |
| 70 | 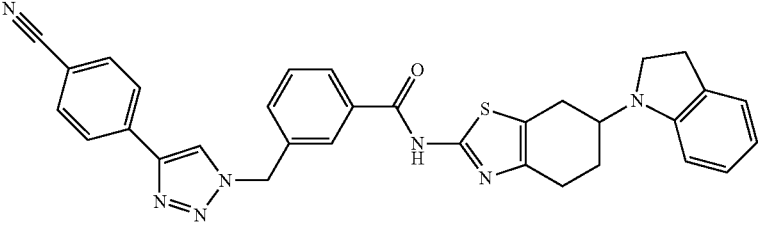 [SMILES: N#Cc1ccc(-c2cn(Cc3cccc(C(=O)Nc4nc5c(s4)CC(N4CCc6ccccc64)CC5)c3)nn2)cc1] |
| 71 | 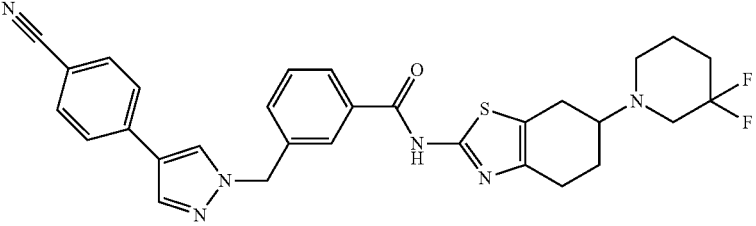 |
| 72 | 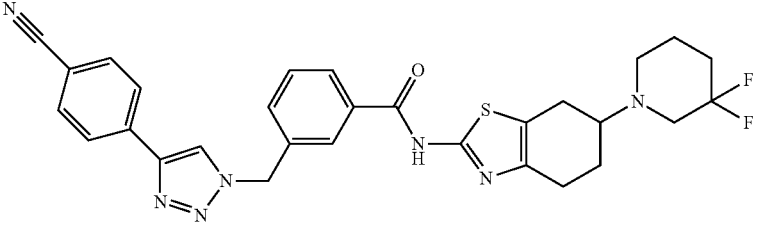 [SMILES: N#Cc1ccc(-c2cn(Cc3cccc(C(=O)Nc4nc5c(s4)CC(N4CCCC(F)(F)C4)CC5)c3)nn2)cc1] |
| 73 | 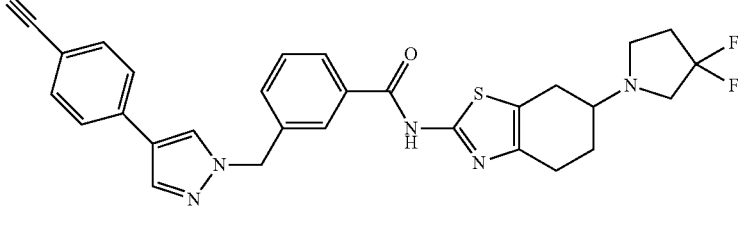 |
| 74 | 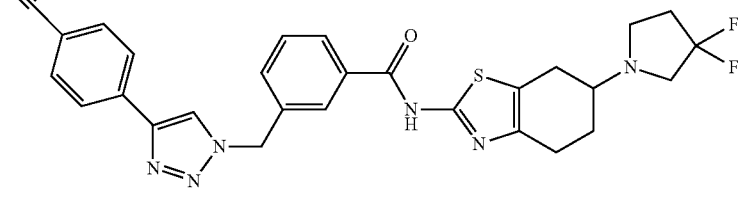 |

TABLE 1-continued

| Cpd Number | Structure |
|---|---|
| 75 | [Structure: 4-cyanophenyl-pyrazole-CH2-benzamide-N-H-tetrahydrobenzothiazole-N-piperidinone] |

In one embodiment, the invention relates to any of the compounds depicted in Table 1 above or the pharmaceutically acceptable salts thereof.

In another embodiment, the invention relates to a compound selected from compounds 1-8, 10, 11, 13-15, 18, 20, 22-33, 36, 40-46, 48, 49, 51-53, 55-59, 64-68, 71 and 73 or the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$ alkyl" is a saturated aliphatic hydrocarbon monovalent radical containing 1-4 carbons such as methyl, ethyl, n-propyl, 1-methylethyl(isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

As used herein, "nitrogen" or N and "sulfur" or S includes any oxidized form of nitrogen and sulfur and the quaternized form of any basic nitrogen. For example, for an —$S$—$C_{1-6}$ alkyl radical, unless otherwise specified, this shall be understood to include —$S(O)$—$C_{1-6}$ alkyl and —$S(O)_2$—$C_{1-6}$ alkyl, likewise, —$S$—$R_a$ may be represented as phenyl-$S(O)_m$— when $R_a$ is phenyl and where m is 0, 1 or 2.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carbocylic acid and an amine in the presence of 1-(3-dimethylaminopropyl)-3-ethylcarbodiimide (EDC) and 1-hydroxybenzotriazole. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

Compounds of formula I having X=

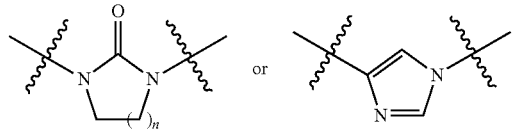

may be prepared as described in Scheme 1 for

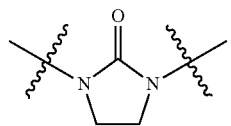 [SMILES: *N1CCN(*)C1=O]

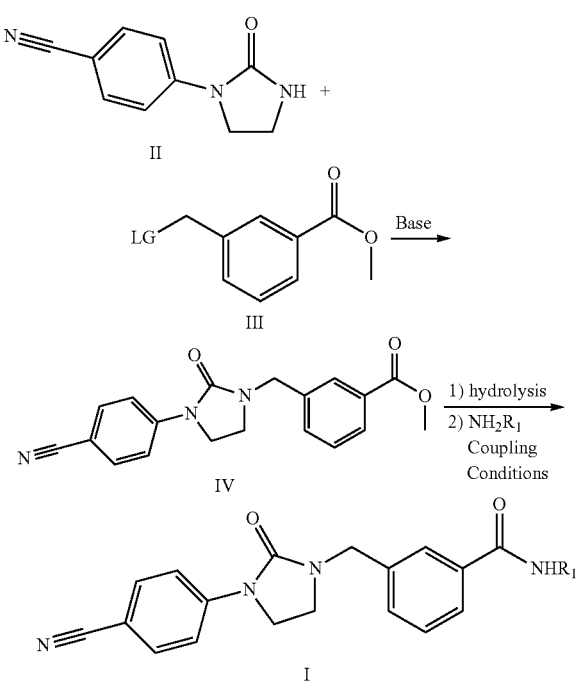

As shown in Scheme 1, N-4-cyanophenyl urea II is treated with a base such as NaH. The subsequent anion is reacted with benzoic acid methyl ester 3-methyl substituent III, containing a leaving group LG, such as Br or Cl, under basic conditions to give a benzylic urea, IV. The ester is hydrolyzed under basic aqueous conditions followed by reacting the subsequent acid with amine $NH_2R_1$ and suitable coupling agent such as EDC in a suitable solvent such DMF to give the desired compound of formula (I).

Compounds of formula I having X=

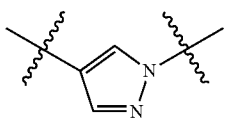

may be prepared as described in Scheme 2.

Compounds of formula I where X=

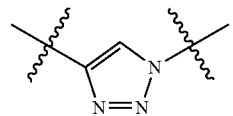 [SMILES: *c1cn(*)nn1]

may be prepared as illustrated in Scheme 3

Scheme 2

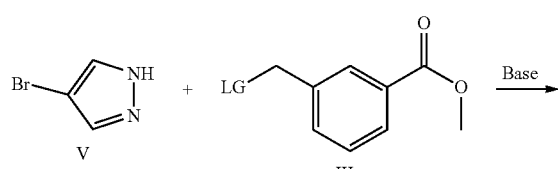

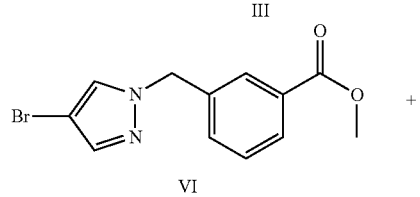

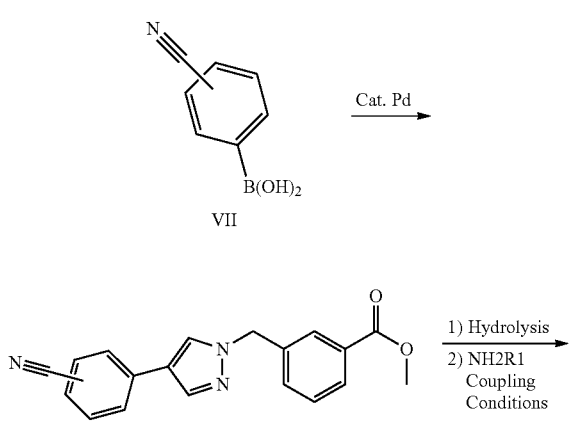

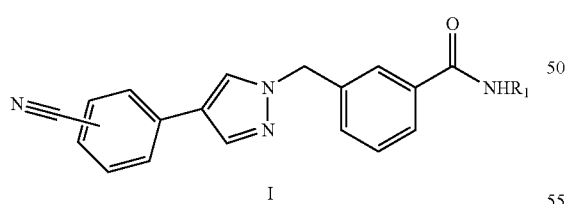

Scheme 3

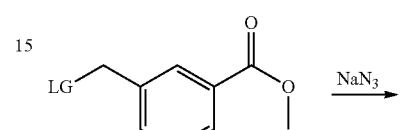

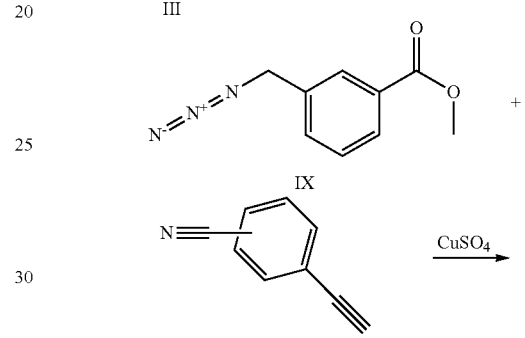

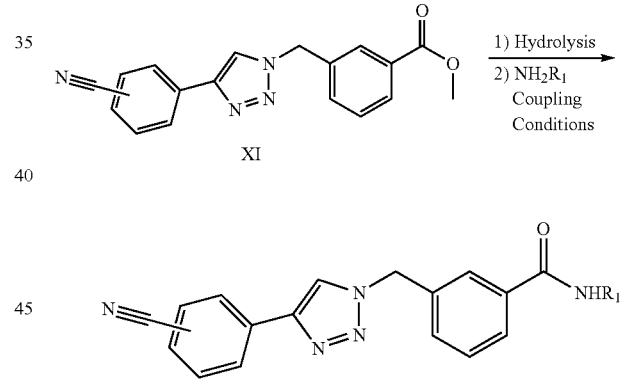

As shown in Scheme 2, 3-bromo pyrazole V is treated base such as NaH. The subsequent anion is reacted with intermediate III, containing a leaving group LG such as Br or Cl under basic conditions to give N-benzylic pyrazole VI. This intermediate is reacted under palladium catalysis with a cyanophenyl boronic acid VII to give cross-coupled product VIII. The ester is hydrolyzed under basic aqueous conditions followed by reacting the subsequent acid with amine NH$_2$R$_1$ and a suitable coupling agent such as EDC in a suitable solvent such DMF to give the desired compound of formula I.

As shown in Scheme 3, intermediate III, containing a leaving group such as Br or Cl is reacted with sodium azide to give a benzylic azide IX. This compound is reacted with cyanophenyl alkyne X with CuSO$_4$ to give triazole XI. The ester is hydrolyzed under basic aqueous conditions followed by reacting the subsequent acid with amine NH$_2$R$_1$ and a suitable coupling agent such as EDC in a suitable solvent such DMF to give the desired compound of formula I.

Compounds of formula I where X=

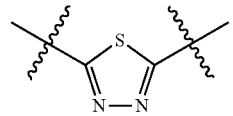 [SMILES: *c1nnc(*)o1] or 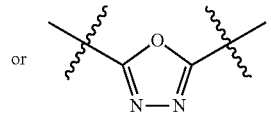

may be prepared as described in Scheme 4 for

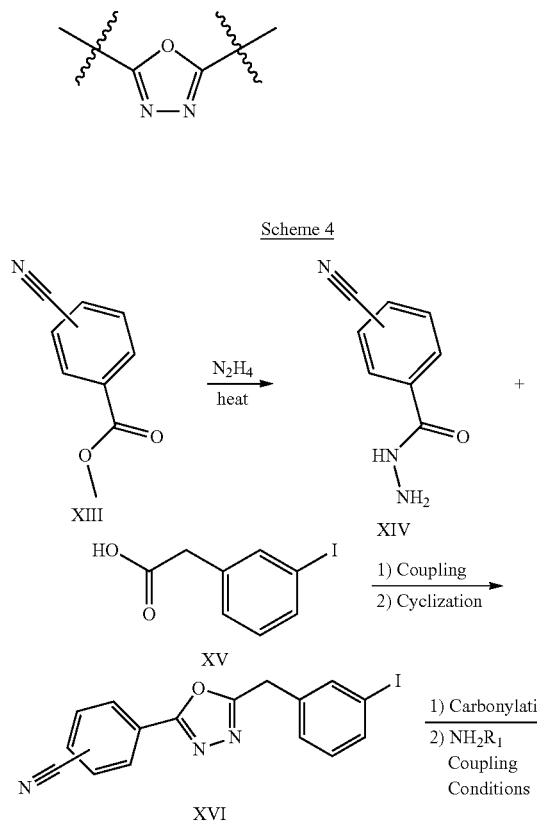

Scheme 4

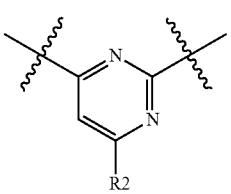

As shown in Scheme 4, cyanobenzoic acid methyl ester XIII is treated with hydrazine while heating to give hydrazide XIV. This intermediate is coupled to 3-iodophenyl acetic acid XV and treated under condensation conditions such as treatment with POCl$_3$ to give oxadiazole XVI. The iodide is reacted under carbonylation conditions with molybdenum hexacarbonyl and the subsequent carboxylic acid is reacted with amine NH$_2$R$_1$ and suitable coupling agent such as EDC in a suitable solvent such DMF to give the desired compound of formula I.

Compounds of formula I where X=

R2 = H, CH3 may be prepared as described in Scheme 5.

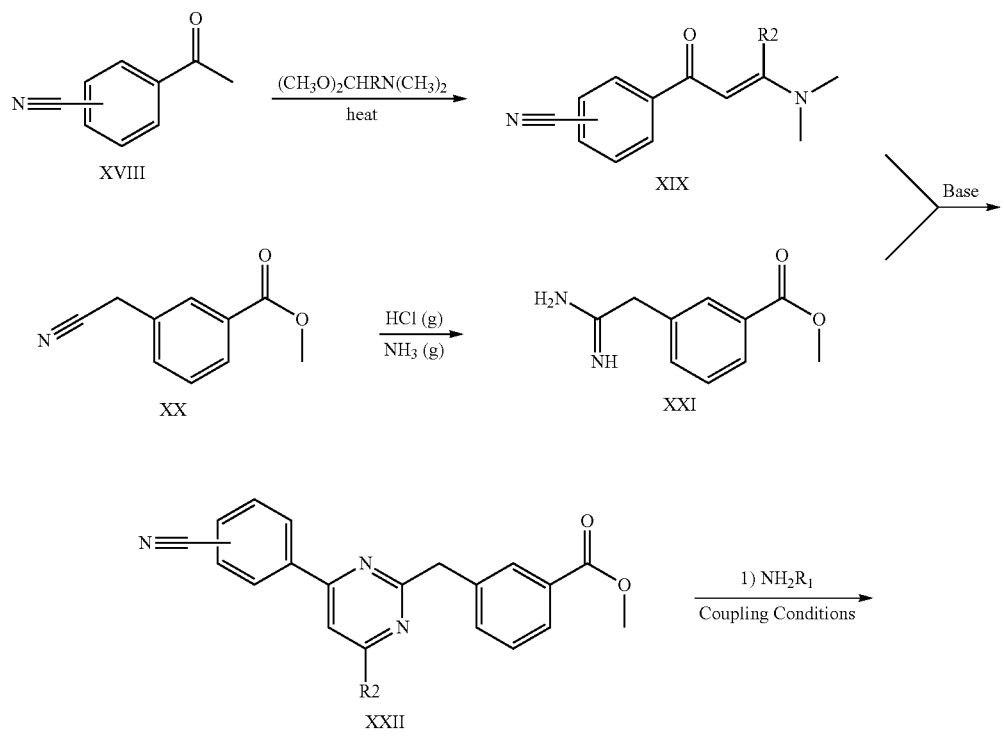

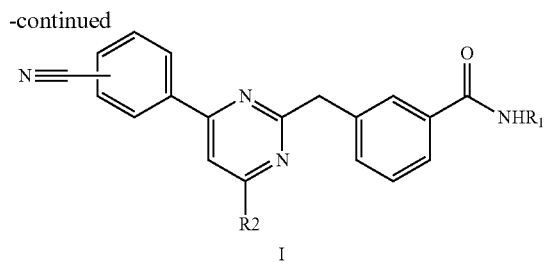

I

As shown is Scheme 5, a cyano acetophenone XVIII is reacted with N-dimethylamino-dimethoxymethane with heating to give the dimethylamino adduct XIX. In parallel, cyanomethylbenzoic acid methyl ester XX is treated with anhydrous HCl gas followed by anhydrous ammonia gas to provide crude amidine XXI. Amidine XXI and intermediate XIX are reacted under basic hydrolytic conditions to provide pyrimidine nitrile benzoic acid XXII. The ester is hydrolyzed under basic aqueous conditions followed by reacting the subsequent carboxylic acid with amine $NH_2R_1$ and a suitable coupling agent such as EDC in a suitable solvent such DMF to give the desired compound of formula I.

Compounds of formula I where X=

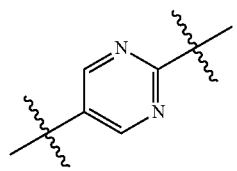 [SMILES: *c1cnc(*)nc1]

may be prepared as described in Scheme 6.

Scheme 6

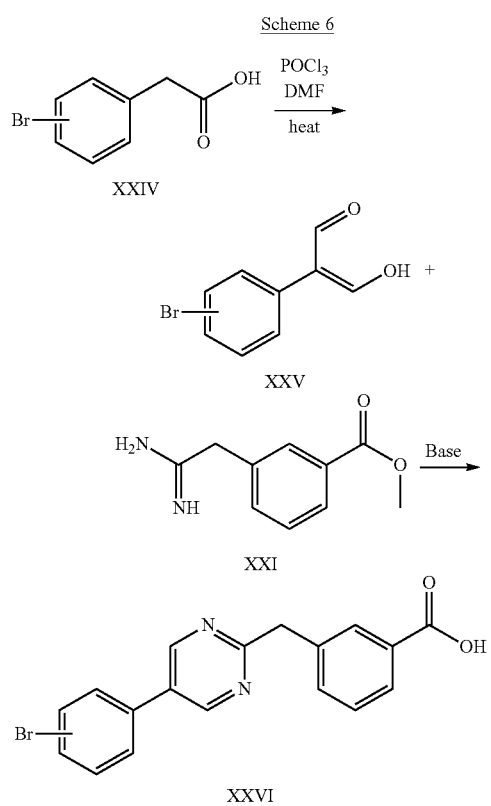

XXVII

I

As shown in Scheme 6, bromophenyl acetic acid XXIV is reacted with $POCl_3$ and DMF with heating to give intermediate XXV. This product is reacted with previously described amidine XXI under basic, hydrolytic conditions to give pyrimidinyl bromo benzoic acid XXVI. This intermediate is reacted with $ZnCN_2$ under catalytic conditions to give aryl nitrile intermediate XXVII. Intermediate XXVII is reacted with amine $NH_2R_1$ and suitable coupling agent such as EDC in a suitable solvent such DMF to give the desired compound of formula I.

Compounds of formula I where X=

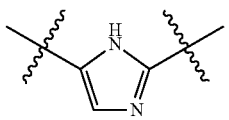 [SMILES: *c1cnc(*)[nH]1]

may be prepared as described in Scheme 7.

Scheme 7

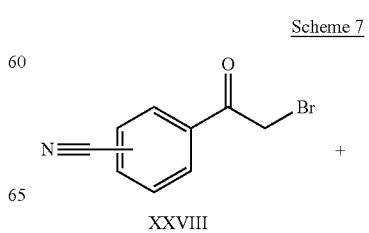

XXVIII

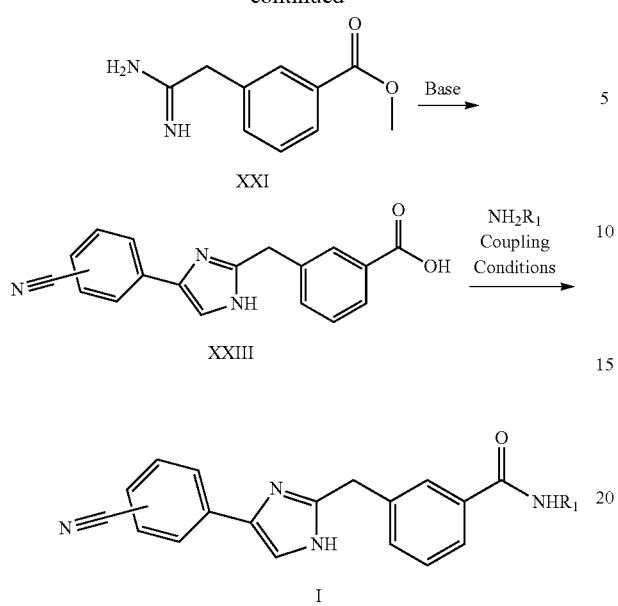

As shown in Scheme 7, bromo cyanoacetophenone XXVIII is combined with previously described amidine XXI under basic hydrolytic conditions to give intermediate XXIII which is then reacted with amine $NH_2R_1$ and suitable coupling agent such as EDC in a suitable solvent such DMF to give the desired compound of formula I.

Compounds of formula I where X=

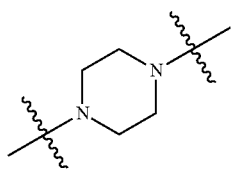 [SMILES: *N1CCN(*)CC1]

may be prepared as described in Scheme 8

Scheme 8

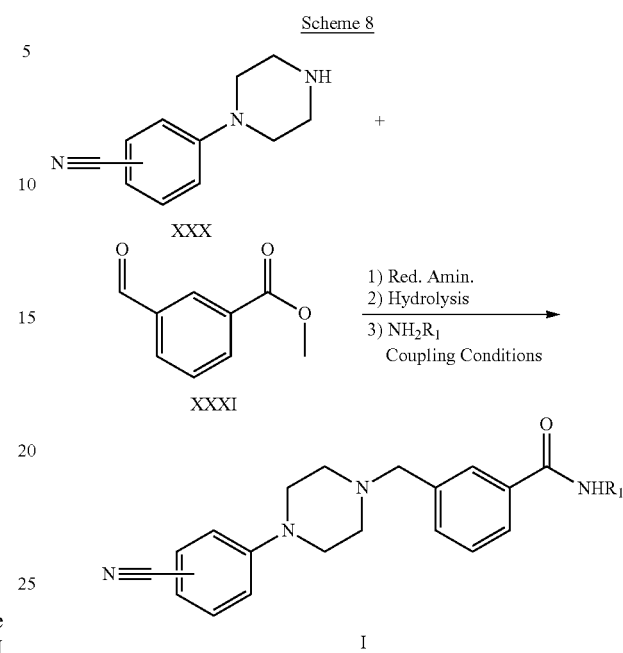

As shown in Scheme 8, N-cyanophenyl piperazine XXX is treated with 3-formyl benzoic acid methyl ester under reductive amination conditions such as reaction under acidic conditions such as AcOH with heating, followed by a reducing agent such as $NaBH(OAc)_3$ to give benzyl piperazinyl esters. The ester is hydrolyzed under basic aqueous conditions followed by reacting the subsequent acid with amine $NH_2R_1$ and a suitable coupling agent such as EDC in a suitable solvent such DMF to give the desired compound of formula I.

All of the compounds in Table I were prepared by the methods illustrated above and in the Synthetic Examples section below.

Retention times (RT) reported for compounds in the Synthetic Examples section were obtained using one of the following methods:

| HPLC Method | Time (min) | Mobile Phase | | Flow (mL/min) | Column |
| --- | --- | --- | --- | --- | --- |
| | | $H_2O$ (0.1% FA) | $CH_3CN$ (0.1% FA) | | |
| A1 | 0 | 95 | 5 | 2.5 | Agilent Zorbax C18 SB |
| | 1.7 | 5 | 95 | 2.5 | 3.5 um 4.6 × 30 mm cartridge |
| | 2 | 5 | 95 | 2.5 | |
| | 2.1 | 95 | 5 | 2.5 | |
| | 2.3 | 95 | 5 | 2.5 | |
| B1 | 0 | 70 | 30 | 2.5 | Agilent Zorbax C18 SB |
| | 1.7 | 5 | 95 | 2.5 | 3.5 um 4.6 × 30 mm cartridge |
| | 2 | 5 | 95 | 2.5 | |
| | 2.1 | 70 | 30 | 2.5 | |
| | 2.3 | 70 | 30 | 2.5 | |
| C1 | 0 | 99 | 1 | 2.5 | Agilent Zorbax C18 SB |
| | 1.7 | 50 | 50 | 2.5 | 3.5 um 4.6 × 30 mm cartridge |
| | 2 | 5 | 95 | 2.5 | |
| | 2.1 | 5 | 95 | 2.5 | |
| | 2.3 | 99 | 1 | 2.5 | |
| D1 | 0 | 95 | 5 | 1.5 | Agilent Zorbax Eclipse |
| | 7 | 5 | 95 | 1.5 | XDB-C8 5 um 4.6 × 150 mm |
| | 9 | 5 | 95 | 1.5 | |
| | 9.3 | 95 | 5 | 1.5 | |
| | 10 | 95 | 5 | 1.5 | |

-continued

| HPLC Method | Time (min) | 95% H$_2$O + 5% CH$_3$CN (0.05% Formic Acid) | CH$_3$CN (0.05% Formic Acid) | Flow (mL/min) | Column |
|---|---|---|---|---|---|
| C2 | 0 | 99 | 1 | 2.5 | Agilent Zorbax C18 SB 3.5 um 4.6 × 30 mm cartridge |
|  | 1.6 | 80 | 20 | 2.5 |  |
|  | 1.7 | 5 | 95 | 2.5 |  |
|  | 2 | 5 | 95 | 2.5 |  |
|  | 2.1 | 99 | 1 | 2.5 |  |
|  | 2.3 | 99 | 1 | 2.5 |  |
| D2 | 0 | 99 | 1 | 1.5 | Agilent Zorbax Eclipse XDB-C8 5 um 4.6 × 150 mm column |
|  | 2 | 80 | 20 | 1.5 |  |
|  | 7 | 5 | 95 | 1.5 |  |
|  | 9 | 5 | 95 | 1.5 |  |
|  | 9.3 | 99 | 1 | 1.5 |  |
|  | 10 | 99 | 1 | 1.5 |  |
| A3 | 0 | 88 | 12 | 1.5 | Agilent SB-C18 1.8 um 3 × 50 mm column |
|  | 0.25 | 70 | 30 | 1.5 |  |
|  | 0.3 | 60 | 40 | 1.5 |  |
|  | 1.19 | 5 | 95 | 1.5 |  |
|  | 1.75 | 0 | 100 | 1.5 |  |
| B3 | 0 | 60 | 40 | 1.5 | Agilent Eclipse C8 1.8 um 3 × 50 mm column |
|  | 1.19 | 15 | 85 | 1.5 |  |
|  | 1.75 | 0 | 100 | 1.5 |  |
| C3 | 0 | 95 | 5 | 1.5 | Agilent SB-AQ 1.8 um 3 × 50mm column |
|  | 0.25 | 50 | 50 | 1.5 |  |
|  | 0.3 | 70 | 30 | 1.5 |  |
|  | 1.3 | 10 | 90 | 1.5 |  |
|  | 1.7 | 0 | 100 | 1.5 |  |
| D3 | 0 | 95 | 5 | 1.5 | Agilent SB-C18 1.8 um 3 × 50 mm column |
|  | 3.8 | 10 | 90 | 1.5 |  |
|  | 4.5 | 0 | 100 | 1.5 |  |

| HPLC Method | Time (min) | 95% H$_2$O + 5% CH$_3$CN (0.05% Formic Acid) | CH$_3$CN (0.05% Formic Acid) | Flow (mL/min) | Column |
|---|---|---|---|---|---|
| E | 0 | 90 | 10 | 0.8 | BEH 2.1 × 50 mm C18, 1.7 um particle diameter |
|  | 1.19 | 5 | 95 | 0.8 |  |
|  | 1.7 | 5 | 95 | 0.8 |  |

SYNTHETIC EXAMPLES

Compound numbers in the following Examples refer to the compound numbers in Table 1.

Example 1

Synthesis of 3-[3-(4-Cyano-phenyl)-2-oxo-imidazolidin-1-ylmethyl]-N-(5-methyl-4,5,6,7-tetrahydrothiazolo[5,4-c]pyridin-2-yl)-benzamide (Compound 1)

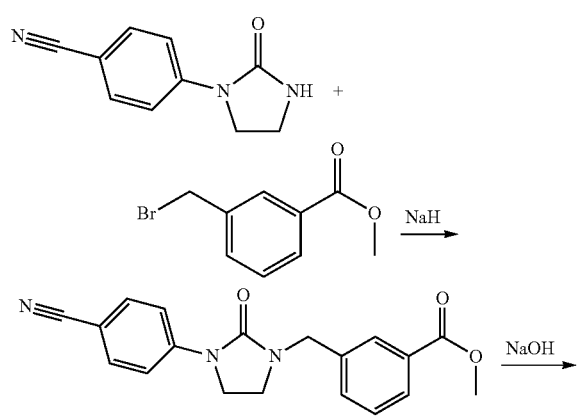

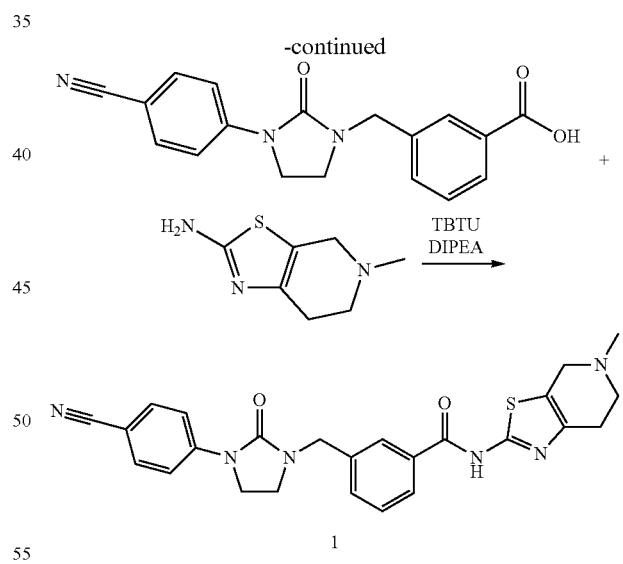

Dissolve 4-(2-oxo-imidazolidin-1-yl)-benzonitrile (0.20 g, 1.07 mmol) into 1 mL of DMF, cool to 0° C. and add a solution of NaH 60% (0.05 g, 1.18 mmol) in 1 mL of DMF. Stir the solution for 30 minutes and add 3-bromomethyl-benzoic acid methyl ester (0.34 g, 1.50 mmol). Warm the reaction to room temperature and stir overnight. Add H$_2$O to the mixture resulting in the precipitation of a white solid. Filter the solid, wash with H$_2$O and dry to give 0.33 g, 92% yield, of 3-[3-(4-cyano-phenyl)-2-oxo-imidazolidine-1-ylmethyl]-benzoic acid methyl ester.

Dissolve 3-[3-(4-cyano-phenyl)-2-oxo-imidazolidine-1-ylmethyl]-benzoic acid methyl ester (0.10 g, 0.30 mmol) into 2 mL of THF. Add NaOH (10 N, 2 mL, 20 mmol) to the solution and stir vigorously at room temperature overnight. Concentrate the mixture to near dryness and suspend in 20 mL of H₂O. Adjust the pH 4.0 by addition of AcOH. Collect the solid and dry to provide the give 0.10 g, 100% yield, of 3-[3-(4-cyano-phenyl)-2-oxo-imidazolidine-1-ylmethyl]-benzoic acid.

Place 3-[3-(4-cyano-phenyl)-2-oxo-imidazolidine-1-ylmethyl]-benzoic acid (0.10 g, 0.31 mmol), 5-methyl-4,5,6,7-tetrahydro-thiazolo[5,4-c]pyridin-2-ylamine (0.05 g, 0.31 mmol), TBTU (O-(benzotriazol-1-yl)-N,N,N',N'-tetramethyluronium tetrafluoroborate) (0.15 g, 0.47 mmol) and DIPEA (0.26 mL, 1.40 mmol) in a flask containing dry DMF (3 mL). Stir the mixture at room temperature overnight under N₂.

Purify the mixture by preparative HPLC (AcCN:H₂O 1:1, 0.1% TFA) to provide 0.09 g, 48% yield, of 3-[3-(4-cyano-phenyl)-2-oxo-imidazolidin-1-ylmethyl]-N-(5-methyl-4,5,6,7-tetrahydro-thiazolo[5,4-c]pyridin-2-yl)-benzamide trifluoroacetic acid as a solid. MS, ES− 471.25 (M−H), rt 0.54 min.

The following compounds were made analogously (Example 1)

Compound 3: 3-[3-(4-Cyano-phenyl)-2-oxo-imidazolidin-1-ylmethyl]-N—((S)-6-dimethylamino-4,5,6,7-tetrahydro-benzothiazol-2-yl)-benzamide. MS, ES+ 501.03 (M+H), rt 0.57 min.

Compound 6: 3-[3-(4-Cyano-phenyl)-2-oxo-imidazolidin-1-ylmethyl]-N—((S)-6-morpholin-4-yl-4,5,6,7-tetrahydro-benzothiazol-2-yl)-benzamide. MS, ES+ 543.4 (M+H), rt 1.19 min.

Example 2

Synthesis of 3-[4-(4-cyano-phenyl)-pyrimidin-2-ylmethyl]-N—((S)-6-morpholin-4-yl-4,5,6,7-tetrahydro-benzothiazol-2-yl)-benzamide (Compound 37)

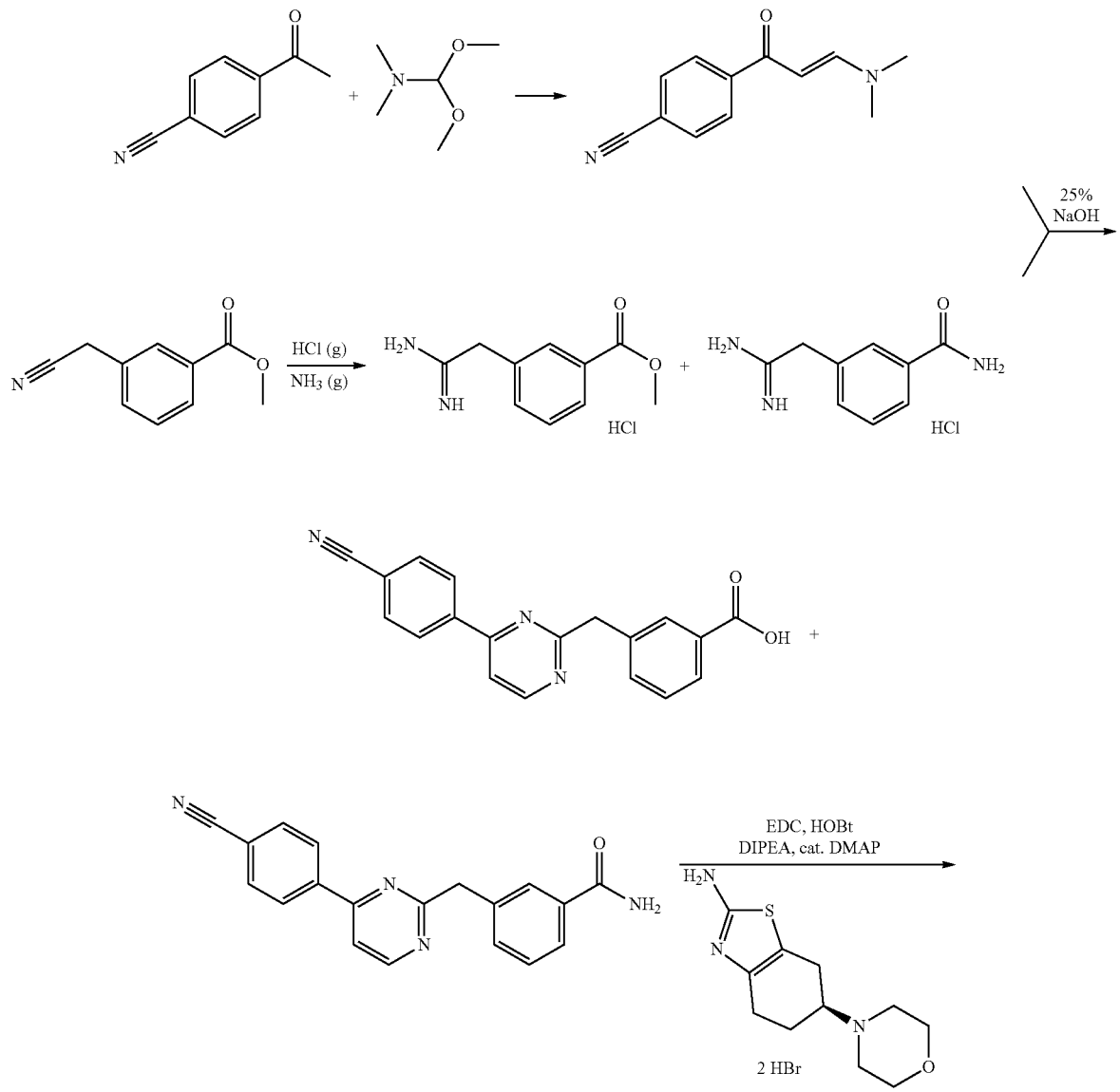

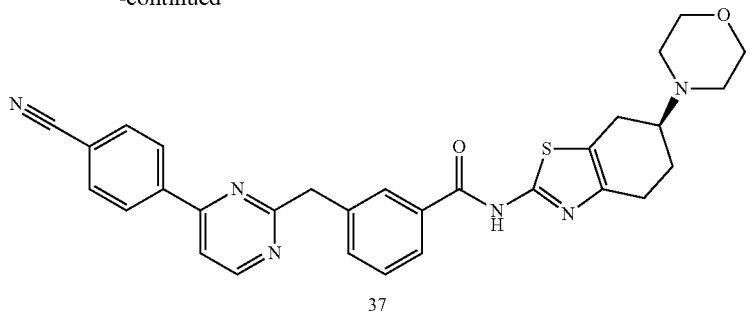

37

Combine dimethoxymethylamine (2.66 mL, 20.0 mmol) and 4-acetyl benzonitrile (1.45 g, 10.0 mmol) in a round bottom flask. Heat the mixture at 110° C. for 1 h. Cool the heterogenous mixture to room temperature, concentrate to dryness and recrystallize in Et$_2$O/Hexanes to give 1.59 g, 79% yield of 4-(3-dimethylamino-acryloyl)-benzonitrile as a solid.

Dissolve 3-cyanomethyl-benzoic acid methyl ester (2.55 g, 14.6 mmol) into 40 mL of absolute MeOH. Cool the flask to 4° C. and bubble HCl (g) in for 20 min with stirring. Cap the flask and keep in <4° C. freezer for 36 h. Concentrate the mixture at 4° C. Dissolve the solid immediately into 100 mL of dry MeOH and bubble NH$_3$ (g) in for 20 min. Seal the flask and heat at 50° C. for 18 h. Concentrate the resulting yellow mixture to give 3.51 g of a solid. LC-MS and $^1$H NMR indicate a 2:1 mixture of 3-carbamimidoylmethyl-benzoic acid methyl ester hydrochloride and 3-carbamimidoylmethyl-benzamide hydrochloride.

Suspend the above mixture (0.17 g) and 4-(3-dimethylamino-acryloyl)-benzonitrile (0.10 g, 0.50 mmol) into 2.5 mL of MeOH in a microwave tube. Add 1 mL of 25% NaOMe in MeOH, seal the tube and heat to 120° C. for 10 min. Concentrate the mixture to dryness and suspend the residue into 20 mL of H$_2$O. Add 5% HCl in a dropwise fashion until pH is acidic. Extract the aqueous phase with 3×20 mL of CH$_2$Cl$_2$. Dry the organic phase with MgSO$_4$, filter and concentrate to give 0.16 g of crude 3-[4-(4-cyano-phenyl)-pyrimidin-2-ylmethyl]-benzoic acid/3-[4-(4-cyano-phenyl)-pyrimidin-2-ylmethyl]-benzamide as powder.

Dissolve 3-[4-(4-cyano-phenyl)-pyrimidin-2-ylmethyl]-benzoic acid/3-[4-(4-cyano-phenyl)-pyrimidin-2-ylmethyl]-benzamide (0.16 g) into 3 mL of DMF. Add EDC (0.19 g, 0.88 mmol) and HOBT hydrate (0.14 g, 0.88 mmol) to the mixture and stir for 1 h. Add (S)-6-morpholin-4-yl-4,5,6,7-tetrahydro-benzothiazol-2-ylamine dihydrobromide (0.30 g, 0.75 mmol), DIPEA (0.37 mL, 2.00 mmol) and catalytic DMAP. Place the mixture in a 60° C. bath under a stream of Ar and stir 14 h. Purify via the Prep HPLC (10%-70% CH$_3$CN/H$_2$O) to give 0.07 g, 79% yield of 3-[4-(4-cyano-phenyl)-pyrimidin-2-ylmethyl]-N—((S)-6-morpholin-4-yl-4,5,6,7-tetrahydro-benzothiazol-2-yl)-benzamide trifluoroacetate. MS, ES+ 537.20 (M+H), rt 1.08 min.

The following compounds were prepared analogously (Example 2)

Compound 36: 3-[4-(3-Cyano-phenyl)-pyrimidin-2-ylmethyl]-N—((S)-6-morpholin-4-yl-4,5,6,7-tetrahydro-benzothiazol-2-yl)-benzamide. MS, ES+ 537.20 (M+H), rt 1.05 min.

Compound 47: 3-[4-(4-Cyano-phenyl)-6-methyl-pyrimidin-2-ylmethyl]-N—((S)-6-morpholin-4-yl-4,5,6,7-tetrahydro-benzothiazol-2-yl)-benzamide. MS, ES+ 551.20 (M+H), rt 1.11 min.

Example 3

Synthesis of 3-[5-(4-Cyano-phenyl)-pyrimidin-2-ylmethyl]-N—((S)-6-morpholin-4-yl-4,5,6,7-tetrahydro-benzothiazol-2-yl)-benzamide (Compound 62)

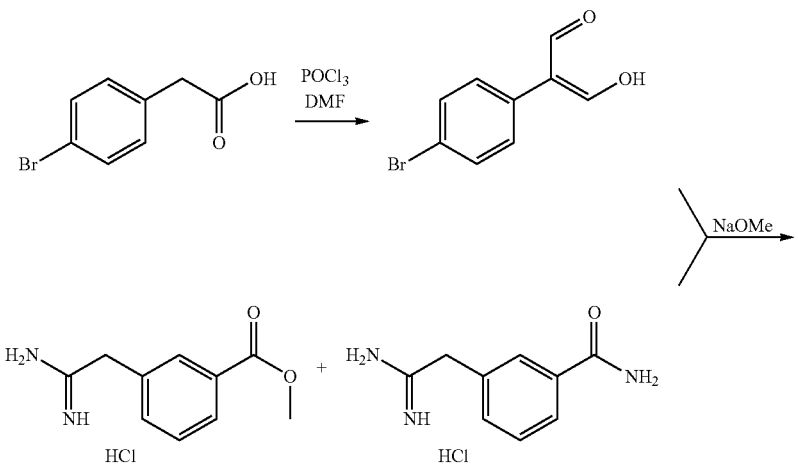

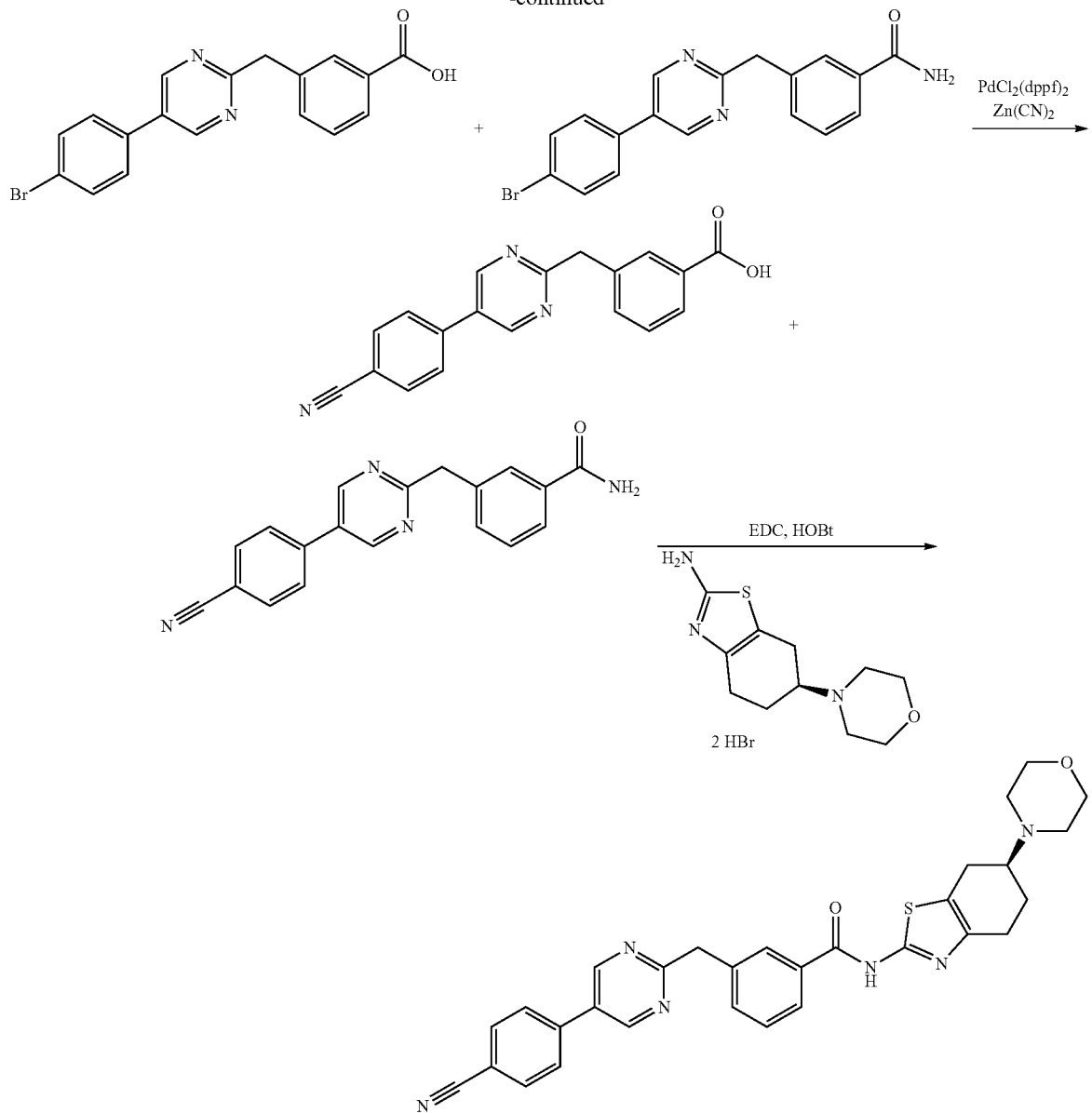

Cool to 4° C. phosphorous oxychloride (2.34 mL, 26.0 mmol) in a 100 mL flask. To this, add 5 mL of DMF and stir mixture for 5 min. Remove the flask from the cooling bath and heat at 75° C. Add (4-bromophenyl)acetic acid (2.00 g, 9.30 mmol) in one portion with an additional 5 mL of DMF and stir the mixture at 75° C. under Ar for 16 h. Pour the mixture into ice and neutralize by slow addition of $K_2CO_3$. Heat the solution at 75° C. and make strongly basic by the addition of 50% aq. NaOH resulting in an oil. Extract the oil from the aq. phase with 2×70 mL of $CH_2Cl_2$, dry with $MgSO_4$, filter and concentrate to give 2.10 g, 99% of 2-(4-bromo-phenyl)-3-hydroxy-propenal.

Suspend a 2:1 mixture of 3-carbamimidoylmethyl-benzoic acid methyl ester hydrochloride/3-carbamimidoylmethyl-benzamide hydrochloride (0.18 g) and 2-(4-bromo-phenyl)-3-hydroxy-propenal (0.18 g, 0.8 mmol) into 2.5 mL of MeOH in a microwave tube. Add 1 mL of 25% NaOMe in MeOH, seal the tube and heat to 120° C. for 10 min. Concentrate the mixture to dryness and suspend the residue into 20 mL of $H_2O$. Add 5% HCl in a drop-wise fashion until pH is acidic. Extract the aqueous phase with 3×20 mL of $CH_2Cl_2$. Dry the organic phase with $MgSO_4$, filter and concentrate to give 0.19 g of crude mixture of 3-[5-(4-bromo-phenyl)-pyrimidin-2-ylmethyl]-benzoic acid/3-[5-(4-bromo-phenyl)-pyrimidin-2-ylmethyl]-benzamide as a powder.

Add $PdCl_2(dppf)_2$ (0.04 g, 0.05 mmol) and $Zn(CN)_2$ (0.17 g, 1.00 mmol) to a mixture of 3-[5-(4-bromo-phenyl)-pyrimidin-2-ylmethyl]-benzoic acid/3-[5-(4-bromo-phenyl)-pyrimidin-2-ylmethyl]-benzamide (0.18 g) in a microwave tube. Dissolve the mixture into 1.5 mL of DMF and 0.15 mL of $H_2O$. Heat the sealed tube to 180° C. for 10 min. Quench the mixture by careful addition of 20 mL of 5% HCl and extract with 3×20 mL EtOAc. Combine the organic fractions, dry with $MgSO_4$, filter and concentrate to give 0.18 g of a mixture of 3-[5-(4-cyano-phenyl)-pyrimidin-2-ylmethyl]-benzoic acid/3-[5-(4-cyano-phenyl)-pyrimidin-2-ylmethyl]-benzamide as an orange solid. The mixture is carried on without further purification.

React the crude 3-[5-(4-cyano-phenyl)-pyrimidin-2-ylmethyl]-benzoic acid according to the procedure in Example 2 to give 0.07 g of 3-[5-(4-cyano-phenyl)-pyrimidin-2-ylmethyl]-N—((S)-6-morpholin-4-yl-4,5,6,7-tetrahydro-benzothiazol-2-yl)-benzamide MS, ES+ 537.20 (M+H), rt 1.06 min.

The following compound was prepared analogously (Example 3)

Compound 63; 3-[5-(3-Cyano-phenyl)-pyrimidin-2-ylmethyl]-N—((S)-6-morpholin-4-yl-4,5,6,7-tetrahydro-benzothiazol-2-yl)-benzamide. MS, ES+ 537.20 (M+H), rt 1.07 min.

Example 4

Synthesis of 3-[4-(3-Cyano-phenyl)-piperazin-1-ylmethyl]-N—((S)-6-morpholin-4-yl-4,5,6,7-tetrahydro-benzothiazol-2-yl)-benzamide (Compound 16)

Dissolve 3-piperazin-1-yl-benzonitrile (0.19 g, 1.00 mmol), 3-formyl-benzoic acid methyl ester (0.33 g, 2.00 mmol) and AcOH (0.64 mL, 10.0 mmol) in 5 mL dichloroethane. Add NaBH(OAc)$_3$ (0.42 g, 2.00 mmol) and stir the mixture overnight. Add another portion of NaBH(OAc)$_3$ (0.42 g, 2.00 mmol) and stir the mixture an additional 24 h. Concentrate the crude reaction mixture under a stream of N$_2$. Dissolve the residue into 5% HCl and apply to a Dowex column. Wash the column with 1×50 mL 5% HCl, 2×50 mL H$_2$O, 2×50 mL of MeOH and 2×50 mL of dichloromethane. Liberate the basic residues by washing the resin with 3×30 mL of 10% NH$_3$/MeOH and 2×20 mL of dichloromethane. Concentrate the basic washings to give 0.27 g of 3-[4-(3-cyano-phenyl)-piperazin-1-ylmethyl]-benzoic acid methyl ester as a clear oil. $^1$H NMR indicates some contamination with starting amine. The mixture is carried on without further purification.

Dissolve 3-[4-(3-cyano-phenyl)-piperazin-1-ylmethyl]-benzoic acid methyl ester into 10 mL of 1:1 THF/MeOH and add 2 mL of 15% NaOH. Stir the mixture overnight and concentrate to dryness. Dissolve the residue in 5% HCl and

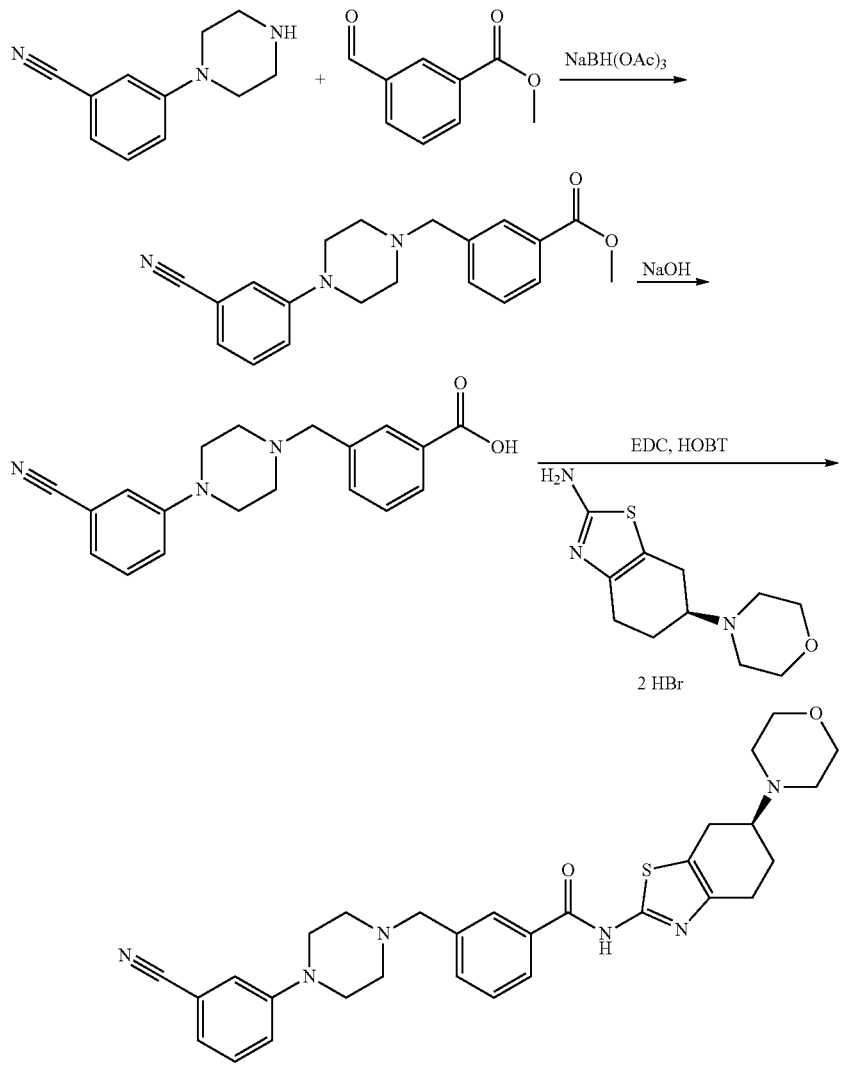

apply to Dowex column. Rinse the resin with 2×20 mL H₂O, 2×20 mL MeOH and 2×20 mL of dichloromethane. Liberate the basic residues by washing the resin with 3×20 mL of 10% NH₃/MeOH to give 0.26 g 3-[4-(3-cyano-phenyl)-piperazin-1-ylmethyl]-benzoic acid as a white solid. ¹H NMR indicates some contamination with starting amine. The crude intermediate is carried on without further purification.

React the crude 3-[4-(3-cyano-phenyl)-piperazin-1-ylmethyl]-benzoic according to Example 1 to give 0.13 g of 3-[4-(3-cyano-phenyl)-piperazin-1-ylmethyl]-N—((S)-6-morpholin-4-yl-4,5,6,7-tetrahydro-benzothiazol-2-yl)-benzamide MS, ES+ 543.77 (M+H), rt 0.96 min.

The following compound was prepared analogously (Example 4)

Compound 17; 3-[4-(4-Cyano-phenyl)-piperazin-1-ylmethyl]-N-((S)-6-morpholin-4-yl-4,5,6,7-tetrahydro-benzothiazol-2-yl)-benzamide: MS, ES+ 543.75 (M+H), rt 0.92 min.

Example 5

Synthesis of 3-[5-(4-Cyano-phenyl)-1,3,4-oxadiazol-2-ylmethyl]-N—((S)-6-morpholin-4-yl-4,5,6,7-tetrahydro-benzothiazol-2-yl)-benzamide (Compound 40)

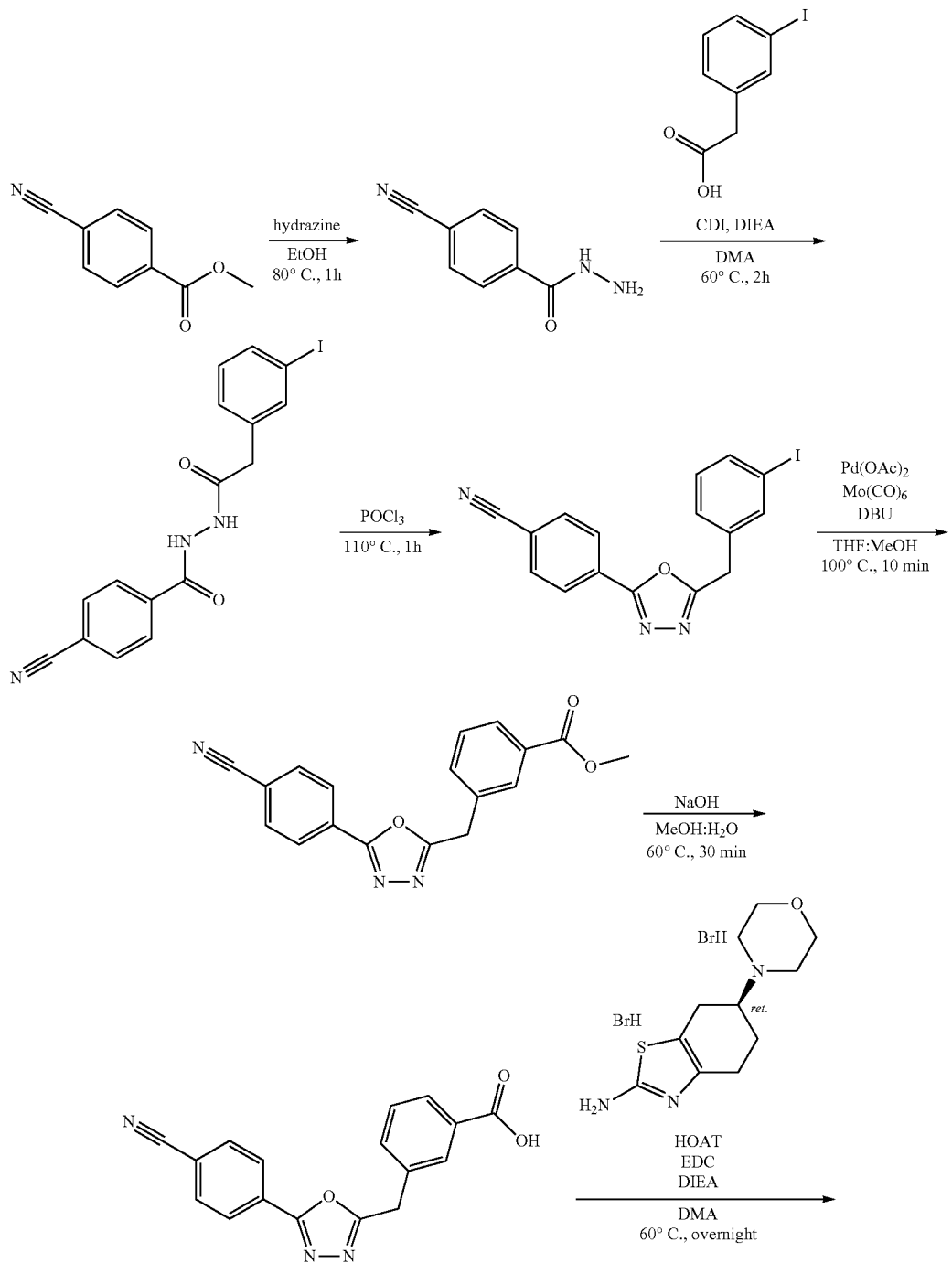

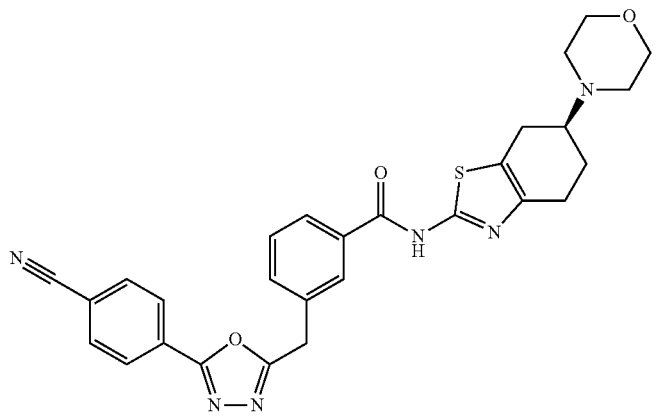

40

Add hydrazine monohydrate (5.50 mL, 110 mmol) to a solution of methyl 4-cyanobenzoate (3.30 g, 20.5 mmol) in 20 mL of EtOH. Heat the mixture at 80° C. for 1 h resulting in a solution. Cool the mixture to room temperature, causing a solid to precipitate from solution. Collect the precipitate by filtration, wash with cold EtOH followed by diethyl ether to provide 1.90 g, 58% yield of 4-cyano-benzoic acid hydrazide as a light yellow solid.

Add 1,1-carbonyldimidazole (0.72 g, 4.40 mmol) to a solution of 3-iodo-phenylacetic acid (1.20 g, 4.6 mmol) in 40 mL of N,N-dimethylacetamide, followed by N,N-diisopropylethylamine (0.79 mL, 4.40 mmol). Stir the mixture at room temperature for 2 h, add 4-cyano-benzoic acid hydrazide (0.64 g (4.0 mmol) and heat the mixture to 60° C. for 2 h. Cool the mixture to room temperature and dilute with H₂O causing a solid to precipitate from solution. Collect the precipitate by filtration, wash with H₂O and diethyl ether dry. Collect any further material that may crystallize from the filtrate. Extract the filtrate with CH₂Cl₂ and concentrate the combined organic phase provide a clear liquid. Dilute this mixture with H₂O resulting in a third crop of material to precipitate from solution. Collect and combine all solid material to give 1.31 g, 71% yield of 4-cyano-benzoic acid N'-[2-(3-iodo-phenyl)-acetyl]-hydrazide as a powder.

Suspend 4-cyano-benzoic acid N'-[2-(3-iodo-phenyl)-acetyl]-hydrazide (0.50 g, 1.23 mmol) in phosphorous oxychloride (2.00 mL, 21.0 mmol) and heat at 110° C. for 1 h, resulting in complete dissolution. Cool the mixture to room temperature, pour into ice water and stir until all of the ice melts resulting in a solid precipitate. Collect the formed solid by filtration, wash with H₂O and dry on the filter pad to provide 0.37 g 77% yield of 4-[5-(3-iodo-benzyl)-[1,3,4]oxadiazol-2-yl]-benzonitrile as a powder.

Add molybedinum hexacarbonyl (0.07 g, 0.26 mmol) to 4-[5-(3-iodo-benzyl)-[1,3,4]oxadiazol-2-yl]-benzonitrile (0.10 g (0.26 mmol) in 2 mL of a 1:1 mixture of tetrahydrofuran MeOH in a microwave pressure tube. Add DBU (0.11 mL, 0.74 mmol) causing the solution to darken. Add palladium acetate (0.006 g, 0.030 mmol) to the mixture, seal the tube and heat at 100° C. in a microwave reactor for 10 minutes. Cool the mixture to room temperature and purify by flash silica gel chromatography to give 0.04 g 48% yield of 3-[5-(4-cyano-phenyl)-[1,3,4]oxadiazol-2-ylmethyl]-benzoic acid methyl ester a solid.

Suspend of 3-[5-(4-cyano-phenyl)[1,3,4]oxadiazol-2-ylmethyl]-benzoic acid methyl ester (0.120 g, 0.376 mmol) in 4 mL of a 1:1 mixture of H₂O:MeOH. Heat the mixture to 60° C., and add 10% aqueous solution of NaOH (0.28 mL, 0.70 mmol). Stir at 60° C. for 30 minutes, cool to room temperature and adjust the pH to 5 by the addition of a 2 N solution of HCl. Concentrate the mixture overnight under a stream of air, dilute crude residue with H₂O and extract with methylene chloride. Wash the combined organic phase with brine, dry over anhydrous sodium sulfate and concentrate to provide 0.11 g 4% yield of 3-[5-(4-cyano-phenyl)-[1,3,4]oxadiazol-2-ylmethyl]-benzoic acid as a white solid.

Add N,N-diisopropylethyl amine (0.17 mL, 0.95 mmol), 7-aza-hydroxybenzotriazole (0.040 g, 0.29 mmol) and EDC (0.06 g (0.31 mmol) to a solution of 3-[5-(4-cyano-phenyl)-[1,3,4]oxadiazol-2-ylmethyl]-benzoic acid (0.106 g, 0.24 mmol) in 3 mL of N,N-dimethylacetamide. Stir the mixture at room temperature for 1 h then add (S)-6-morpholin-4-yl-4,5, 6,7-tetrahydro-benzothiazol-2-ylamine dihydrobromide (0.12 g, 0.30 mmol) in one portion and heat overnight at 60° C. Cool the reaction mixture to room temperature and dilute with H₂O. Add an aqueous solution of sodium bicarbonate until the pH of the solution is alkaline causing a solid to precipitate from solution. Collect the solid by filtration, wash with H₂O and dry on the filter pad. Purify the isolated material by preparative reverse phase HPLC to give 0.02 g, 13% yield of 3-[5-(4-cyano-phenyl)-1,3,4-oxadiazol-2-ylmethyl]-N—((S)-6-morpholin-4-yl-4,5,6,7-tetrahydro-benzothiazol-2-yl)-benzamide as a white powder. MS, ES⁺ 527.67 (M+H), rt 1.24 min.

Example 6
Synthesis of 3-[5-(4-Cyano-phenyl)-1,3,4-thiadiazol-2-ylmethyl]-N—((S)-6-morpholin-4-yl-4,5,6,7-tetrahydro-benzothiazol-2-yl)-benzamide (Compound 56)
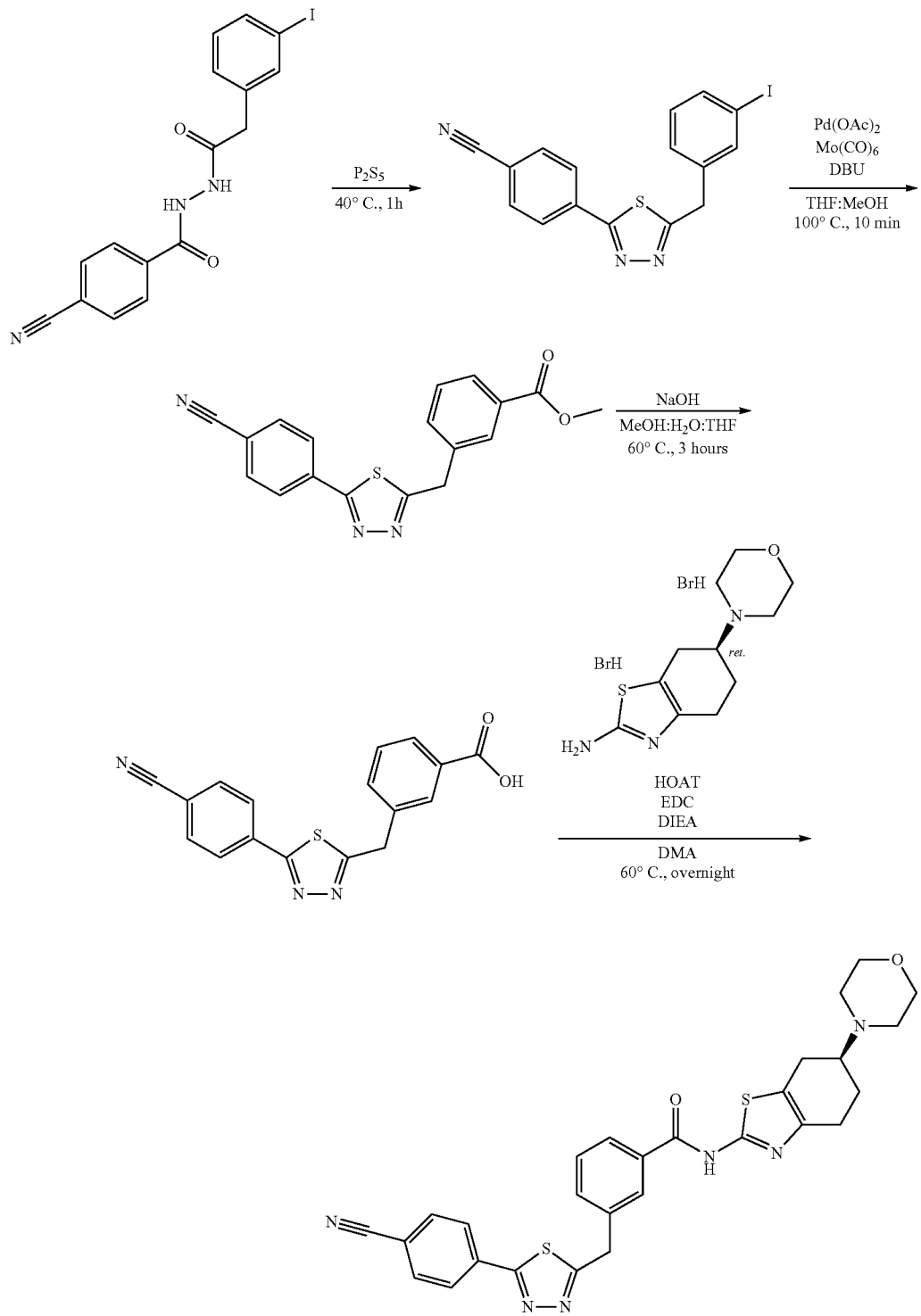
56

Suspend 4-cyano-benzoic acid N'-[2-(3-iodo-phenyl)-acetyl]-hydrazide (0.50 g, 1.23 mmol) in 10 mL of 1,4-dioxane. Add phosphorous pentasulfide (0.55 g, 2.5 mmol) in one portion. Stir the mixture at room temperature for 15 minutes and heat to 40° C. for 1 h. Cool the mixture to room temperature, pour into ice water and stir until all of the ice is melted. Extract the mixture with $CH_2Cl_2$, dry the combined organics over anhydrous sodium sulfate and concentrate under reduced pressure. Purify the residue by flash silica gel chromatography to provide 0.34 g, 61% yield of 4-[5-(3-iodo-benzyl)-[1,3,4]thiadiazol-2-yl]-benzonitrile as a solid.

Dissolve 4-[5-(3-iodo-benzyl)-[1,3,4]thiadiazol-2-yl]-benzonitrile (0.34 g, 0.75 mmol) into 8 mL of a 1:1 mixture of THF:MeOH in a microwave pressure tube. Add molybedinum hexacarbonyl (0.25 g, 0.95 mmol) and DBU (0.32 mL, 2.10 mmol) causing the solution to darken. Add palladium acetate (0.03 g, 0.11 mmol), seal the tube and heat at 100° C. in a microwave reactor for 10 min. Concentrate the mixture onto silica gel and purify by flash silica gel chromatography to provide (0.150 g, 60% yield of 3-[5-(4-cyano-phenyl)-[1,3,4]thiadiazol-2-ylmethyl]-benzoic acid methyl ester as a solid.

Suspend 3-[5-(4-cyano-phenyl)-[1,3,4]thiadiazol-2-ylmethyl]-benzoic acid methyl ester (0.15 g, 0.45 mmol) in 10 mL of a 1:1 mixture of $H_2O$:MeOH, add 10% aqueous solution of NaOH (0.48 mL, 1.20 mmol) and heat to 60° C. After stifling for 3 h add 5 mL of THF to the reaction mixture causing all of the solids to go into solution. Heat the mixture at 60° C. for an additional 2 h then cool to room temperature. Adjust the pH to slightly acidic by the addition of a 2N solution of HCl. Dilute the mixture with $H_2O$ and wash with $CH_2Cl_2$. Wash the combined organics with brine, dry over anhydrous sodium sulfate and concentrate to provide 0.13 g, 57% yield of 3-[5-(4-cyano-phenyl)-[1,3,4]thiadiazol-2-ylmethyl]-benzoic acid as a solid.

Dissolve 3-[5-(4-cyano-phenyl)-[1,3,4]-thiadiazol-2-ylmethyl]-benzoic acid (0.13 g, 0.28 mmol) in 3 mL of dimethylacetamide. Add N,N-diisopropylethyl amine (0.17 mL, 0.95 mmol), of 7-aza-hydroxybenzotriazole (0.05 g, 0.37 mmol) and EDC (0.07, (0.36 mmol). Stir the mixture at room temperature for 1 h and add (S)-6-morpholin-4-yl-4,5,6,7-tetrahydro-benzothiazol-2-ylamine dihydrobromide (0.14 g, 0.35 mmol) in one portion. Heat the mixture at 60° C. for 15 h. Cool to room temperature and dilute with $H_2O$. Add a saturated aqueous solution of sodium bicarbonate until the pH of the solution is alkaline causing a solid to precipitate from solution. Collect the solid by filtration, wash with $H_2O$ and dry on the filter pad. Purify the material by preparative reverse phase HPLC ($CH_3CN$:$H_2O$ with 0.1% trifluoroacetic acid) to give 0.025 g, 14% yield of 3-[5-(4-cyano-phenyl)-[1,3,4]thiadiazol-2-ylmethyl]-N—((S)-6-morpholin-4-yl-4,5,6,7-tetrahydro-benzothiazol-2-yl)-benzamide as a solid. MS, $ES^+$ 543.62 (M+H), rt 1.50 min.

Example 7

Synthesis of 3-[4-(4-Cyano-phenyl)-[1,2,3]triazol-1-ylmethyl]-N-(5-methyl-4,5,6,7-tetrahydro-thiazolo[5,4-c]pyridin-2-yl)-benzamide (Compound 2)

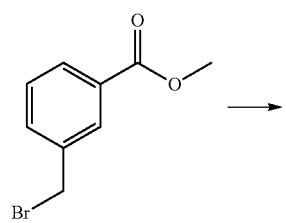

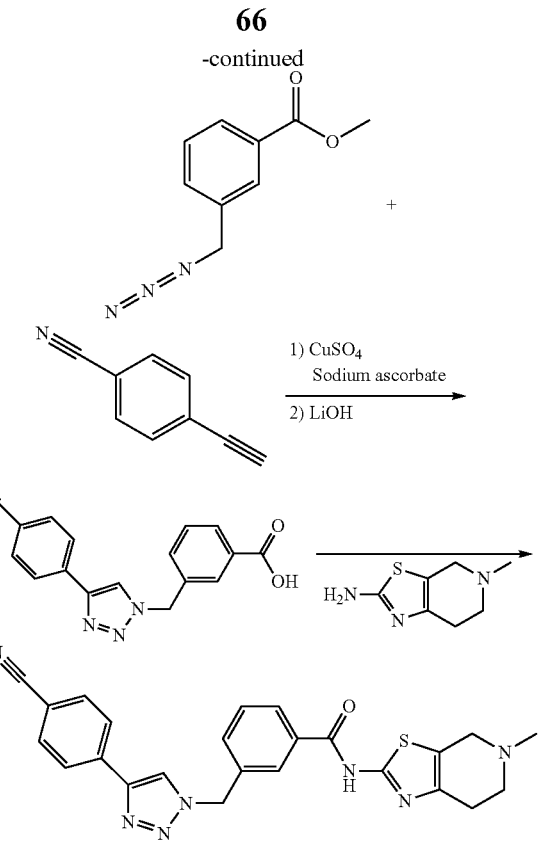

Add sodium azide (0.3 g, 4.8 mmol) to a solution of methyl 3-bromomethylbenzoate (1.00 g, 4.4 mmol) in 10 mL of dimethylacetamide. Stir at room temperature for several h, pour mixture into ice water and extract with EtOAc. Wash combined extracts 4 times with $H_2O$, brine and dry over sodium sulfate. Filter the mixture and concentrate to afford 0.81 g, 97% yield of 3-azidomethyl-benzoic acid methyl ester as an oil.

Treat a solution of 3-azidomethyl-benzoic acid methyl ester (0.4 g, 2.1 mmol) and 4-cyanophenylacetylene (0.25 g, 2.00 mmol) in 1 mL of dichloromethane with 1 mL of 0.1 M aqueous copper (II) sulfate solution and sodium ascorbate (0.06 g, 0.30 mmol). Stir at room temperature overnight, dilute the reaction with $CH_2Cl_2$ and wash 3 times with $H_2O$. Dry the organic layer over sodium sulfate, filter and concentrate to afford a solid. Suspend the residue in diethyl ether and filter to give 0.53 g, 84% yield of 3-[4-(4-cyano-phenyl)-[1,2,3]triazol-1-ylmethyl]-benzoic acid methyl ester.

Add LiOH monohydrate (0.10 g, 2.40 mmol) to a suspension of 3-[4-(4-cyano-phenyl)-[1,2,3]triazol-1-ylmethyl]-benzoic acid methyl ester (0.50 g, 1.60 mmol) in 15 mL of a 4:1 MeOH-water mixture and stir at room temperature for 3 days. Concentrate the mixture to remove most of the MeOH, dilute with additional $H_2O$ and neutralize by the addition of 1N aqueous HCl. Isolate the resulting solid by filtration and dry to afford 0.45 g, 94% yield of 3-[4-(4-Cyano-phenyl)-[1,2,3]triazol-1-ylmethyl]-benzoic acid.

React 3-[4-(4-cyano-phenyl)-[1,2,3]triazol-1-ylmethyl]-benzoic and 5-methyl-4,5,6,7-tetrahydro-thiazolo[5,4-c]pyridin-2-ylamine with HATU (O-(7-azabenzotriazol-1-yl)-N,N,N',N'-tetramethyluronium hexafluorophosphate) to afford 0.06 g, 59% yield of 3-[4-(4-cyano-phenyl)-[1,2,3]triazol-1-ylmethyl]-N-(5-methyl-4,5,6,7-tetrahydro-thiazolo[5,4-c]

pyridin-2-yl)-benzamide trifluoroacetate as described in Example 1. MS, ES+ 456.79 (M+H), rt 1.38 min.

The following compounds were prepared analogously (Example 7)

Compound 4: 3-[4-(4-Cyano-phenyl)-[1,2,3]triazol-1-ylmethyl]-N—((S)-6-dimethylamino-4,5,6,7-tetrahydro-benzothiazol-2-yl)-benzamide. MS, ES+ 484.77 (M+H), rt 1.49 min.

Compound 8: 3-[4-(4-Cyano-phenyl)-[1,2,3]triazol-1-ylmethyl]-N—((S)-6-morpholin-4-yl-4,5,6,7-tetrahydro-benzothiazol-2-yl)-benzamide. MS, ES+ 525.80 (M+H), rt 1.29

Example 8

Synthesis of 3-[4-(4-Cyano-phenyl)-pyrazol-1-ylmethyl]-N—((S)-6-dimethylamino-4,5,6,7-tetrahydro-benzothiazol-2-yl)-benzamide (Compound 5)

sodium sulfate, filter and concentrate to give an oil. Purify the residue by flash chromatography using a gradient of 0-50% EtOAc/hexanes to afford 0.20 g, 32% yield of 3-[4-(4-cyano-phenyl)-pyrazol-1-ylmethyl]-benzoic acid methyl ester as a solid.

Add LiOH monohydrate (0.03 g, 0.8 mmol) to a suspension of 3-[4-(4-cyano-phenyl)-pyrazol-1-ylmethyl]-benzoic acid methyl ester (0.2 g, 0.6 mmol) in 5 mL of a 4:1 MeOH-water mixture and stir the reaction at room temperature overnight. Concentrate the reaction to remove most of the MeOH, dilute with additional $H_2O$ and neutralize by the addition of 1 N aqueous HCl. Isolate the resulting solid by filtration and dry to afford 0.15 g, 71% yield of 3-[4-(4-cyano-phenyl)-pyrazol-1-ylmethyl]-benzoic acid.

React 3-[4-(4-cyano-phenyl)-pyrazol-1-ylmethyl]-benzoic acid and 5-methyl-4,5,6,7-tetrahydro-thiazolo[5,4-c]pyridin-2-ylamine under HATU conditions to afford 0.04 g, 51% yield of 3-[4-(4-cyano-phenyl)-pyrazol-1-ylmethyl]-N—((S)-6-dimethylamino-4,5,6,7-tetrahydro-benzothiazol-

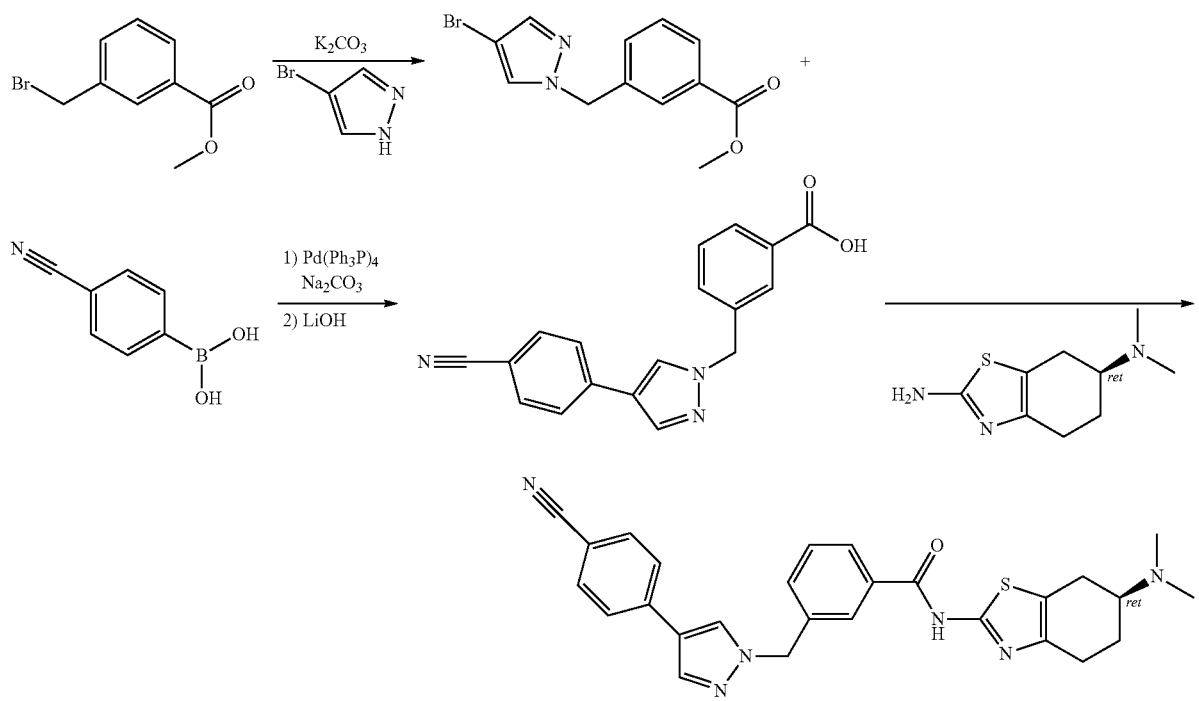

Add sodium carbonate (5.80 g, 41.7 mmol) to a solution of 4-bromopyrazole (3.10 g, 20.9 mmol) and methyl 3-bromomethylbenzoate (4.8 g, 20.9 mmol) in 40 mL of dimethylacetamide. Stir the mixture at 60° C. overnight. Cool the reaction to room temperature and pour into 300 mL of ice water. Collect the resulting solid by filtration and dry to afford 6.0 g, 98% yield of 3-(4-bromo-pyrazol-1-ylmethyl)-benzoic acid methyl ester.

Charge a microwave vial with 3-(4-bromo-pyrazol-1-ylmethyl)-benzoic acid methyl ester (0.60 g, 2.00 mmol), 4-cyanophenylboronic acid (0.35 g, 2.40 mmol), potassium carbonate (0.50 g, 4.80 mmol) and tetrakistriphenylphosphine palladium (0) (0.23 g, 0.2 mmol). Flush the vessel with inert gas and seal. Dissolve the contents of the vial in 10 mL of a 4:1 dioxane-water mixture and microwave at 150° C. for 5 minutes. Dilute the reaction mixture with EtOAc, dry over 2-yl)-benzamide trifluoroacetate as described in Example 1. MS, ES+ 483.80 (M+H), rt 1.30 min.

The following compounds were made analogously (Example 8)

Compound 7: 3-[4-(4-Cyano-phenyl)-pyrazol-1-ylmethyl]-N—((S)-6-morpholin-4-yl-4,5,6,7-tetrahydro-benzothiazol-2-yl)-benzamide. MS, ES+ 525.38 (M+H), rt 1.30
React 3-[4-(4-Cyano-phenyl)-pyrazol-1-ylmethyl]-benzoic acid and (S)-6-morpholin-4-yl-4,5,6,7-tetrahydro-benzothiazol-2-ylamine under the conditions described in Example 2

Compound 10: 3-[4-(4-Cyano-phenyl)-imidazol-1-ylmethyl]-N—((S)-6-morpholin-4-yl-4,5,6,7-tetrahydro-benzothiazol-2-yl)-benzamide. MS, ES+ 525.75 (M+H), rt 1.28 React 3-[4-(4-Cyano-phenyl)-2,3-dihydro-imidazol-1-ylmethyl]-benzoic acid and (S)-6-morpholin-4-yl-4,5,6,7-tetrahydro-benzothiazol-2-ylamine under the conditions described in Example 2

Example 9

Synthesis of ((S)-2-{3-[4-(4-Cyano-phenyl)-pyrazol-1-ylmethyl]-benzoylamino}-4,5,6,7-tetrahydro-benzothiazol-6-yl)-carbamic acid tert-butyl ester (Compound 50) and N—((S)-6-Amino-4,5,6,7-tetrahydro-benzothiazol-2-yl)-3-[4-(4-cyano-phenyl)-pyrazol-1-ylmethyl]-benzamide (Compound 28)

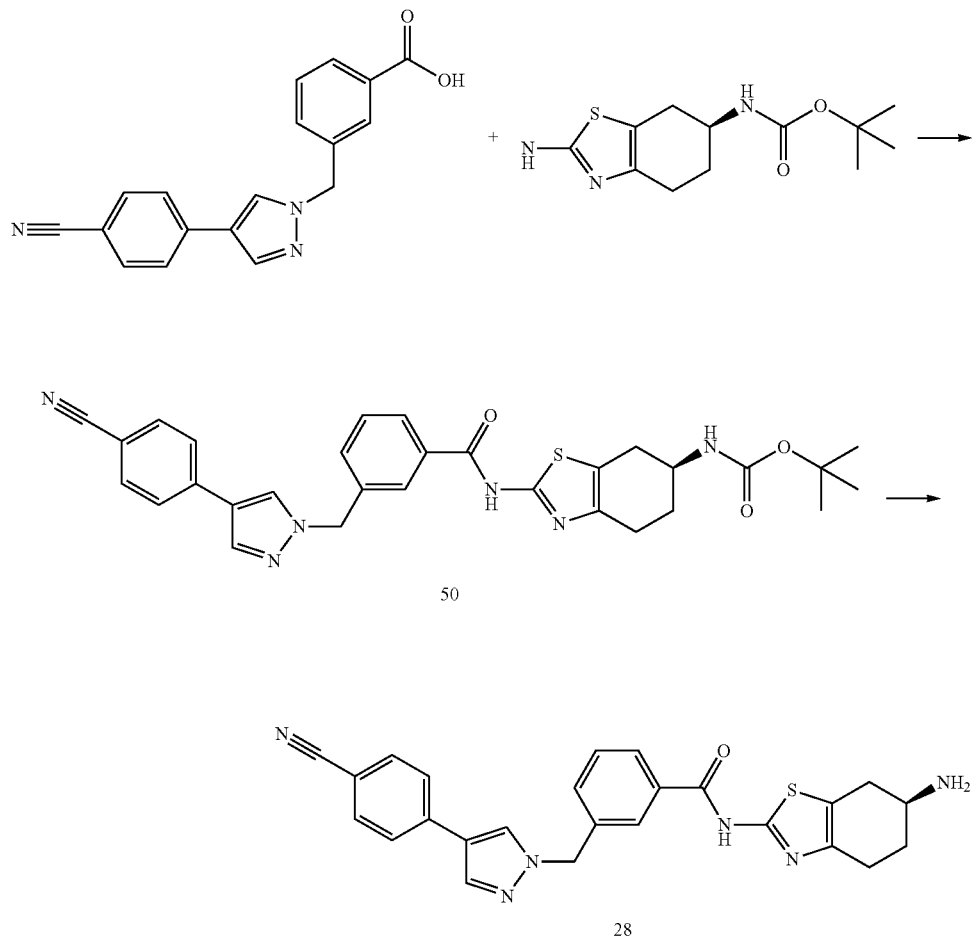

Dissolve 3-[4-(4-cyano-phenyl)-pyrazol-1-ylmethyl]-benzoic acid (0.25 g, 0.82 mmol) and ((S)-2-amino-4,5,6,7-tetrahydro-benzothiazol-6-yl)-carbamic acid tert-butyl ester (0.22 g, 0.82 mmol) and TBTU (0.40 g, 1.24 mmol) and N,N-diisopropylethylamine (0.40 ml, 2.47 mmol) into 1.5 mL dry DMF and stir overnight at room temperature under Ar. Pour the reaction into $H_2O$, giving a precipitate. Filter the solid, wash with $H_2O$, and dry. Extract the filtrate 3 times with EtOAc and washed 4 times with $H_2O$, 3 times with aq. $NH_4Cl$ and once with aq.$Na_2CO_3$. Dry the organic phase and concentrate to give an oil. Both crops are combined and purified via prep plate chromatography eluting with 3% MeOH/$CH_2Cl_2$ to give 0.42 g, 92% yield as a clear hard resin of ((S)-2-{3-[4-(4-cyano-phenyl)-pyrazol-1-ylmethyl]-benzoylamino}-4,5,6,7-tetrahydro-benzothiazol-6-yl)-carbamic acid tert-butyl ester.

MS, ES+ 555.62 (M+H), rt 1.95 min.

Stir ((S)-2-{3-[4-(4-cyano-phenyl)-pyrazol-1-ylmethyl]-benzoylamino}-4,5,6,7-tetrahydro-benzothiazol-6-yl)-carbamic acid tert-butyl ester (0.38 g, 0.69 mmol) in 2 mL $CH_2Cl_2$ and 2 mL TFA for 3 h in a capped flask. Concentrate the reaction and bring to alkaline pH with aq. $Na_2CO_3$. Triturate the residue with $CH_2Cl_2$ and filter the product to give 0.23 g 75% yield of N—((S)-6-amino-4,5,6,7-tetrahydro-benzothiazol-2-yl)-3-[4-(4-cyano-phenyl)-pyrazol-1-ylmethyl]-benzamide as a beige solid. MS, ES+ 455.73 (M+H), rt 1.39 min.

The following compound is prepared analogously (Example 9)

Compound 29: N—((S)-6-Amino-4,5,6,7-tetrahydro-benzothiazol-2-yl)-3-[4-(4-cyano-henyl)-[1,2,3]triazol-1-ylmethyl]-benzamide. MS, electrospray 456.70 (M+H), rt 1.35 min.

Example 10

Synthesis of; 3-[4-(4-Cyano-phenyl)-pyrazol-1-ylmethyl]-N—[(S)-6-(3,3,3-trifluoro-propylamino)-4,5,6,7-tetrahydro-benzothiazol-2-yl]-benzamide (Compound 20) and N-{(S)-6-[Bis-(3,3,3-trifluoro-propyl)-amino]-4,5,6,7-tetrahydro-benzothiazol-2-yl}-3-[4-(4-cyano-phenyl)-pyrazol-1-ylmethyl]-benzamide (Compound 19)

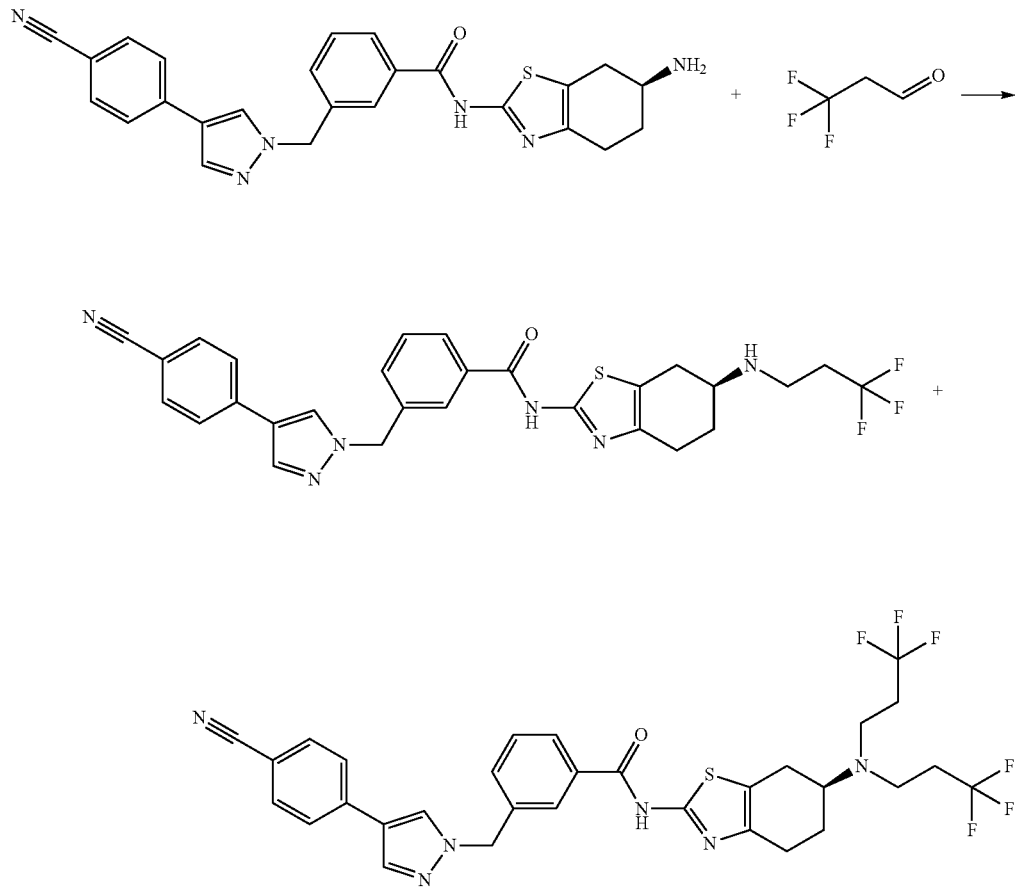

Dissolve N—((S)-6-amino-4,5,6,7-tetrahydro-benzothiazol-2-yl)-3-[4-(4-cyano-phenyl)-pyrazol-1-ylmethyl]-benzamide (0.22 g, 0.48 mmol) and 3,3,3-trifluoropropionaldehyde (0.22 g, 1.94 mmol) and sodium cyanoborohydride (0.12 g, 1.94 mmol) into 5 mL 20% MeOH/CH$_2$Cl$_2$. Add 250 microL of acetic acid and stir overnight at room temperature. Concentrate the mixture and add aq. Na$_2$CO$_3$. Extract 4 times with EtOAc, washed 2 times with aq. Na$_2$CO$_3$ and once with H$_2$O. Dry the organic phase and concentrate to give a clear oil. Purify via SiO$_2$ prep plate chromatography, eluting with 6% MeOH/CH$_2$Cl$_2$/0.5% NH$_4$OH to afford 0.013 g, 4% yield of N-{(S)-6-[bis-(3,3,3-trifluoro-propyl)-amino]-4,5,6,7-tetrahydro-benzothiazol-2-yl}-3-[4-(4-cyano-phenyl)-pyrazol-1-ylmethyl]-benzamide as an oil MS, electrospray 647.8 (M+H), rt 2.11 min. and 147.6 mg, 55% yield of 3-[4-(4-cyano-phenyl)-pyrazol-1-ylmethyl]-N—[(S)-6-(3,3,3-trifluoro-propylamino)-4,5,6,7-tetrahydro-benzothiazol-2-yl]-benzamide as a foamy resin. MS, electrospray 551.69 (M+H), rt 1.58 min.

The following compounds are prepared analogously (Example 10)

Compound 21: N-{(S)-6-[Bis-(3,3,3-trifluoro-propyl)-amino]-4,5,6,7-tetrahydro-benzothiazol-2-yl}-3-[4-(4-cyano-phenyl)-[1,2,3]triazol-1-ylmethyl]-benzamide. MS, electrospray 648.55 (M+H), rt 2.07 min.

Compound 22: 3-[4-(4-Cyano-phenyl)-[1,2,3]triazol-1-ylmethyl]-N—[(S)-6-(3,3,3-trifluoro-propylamino)-4,5,6,7-tetrahydro-benzothiazol-2-yl]-benzamide. MS, electrospray 552.39 (M+H), rt 1.52 min.

Compound 34: 3-[4-(4-Cyano-phenyl)-imidazol-1-ylmethyl]-N—[(S)-6-(3,3,3-trifluoro-propylamino)-4,5,6,7-tetrahydro-benzothiazol-2-yl]-benzamide. MS, electrospray 549.83 (M+H), rt 1.18 min.

Example 11

3-[4-(4-Cyano-phenyl)-pyrazol-1-ylmethyl]-N-{(S)-6-[methyl-(3,3,3-trifluoro-propyl)-amino]-4,5,6,7-tetrahydro-benzothiazol-2-yl}-benzamide (Compound 30)

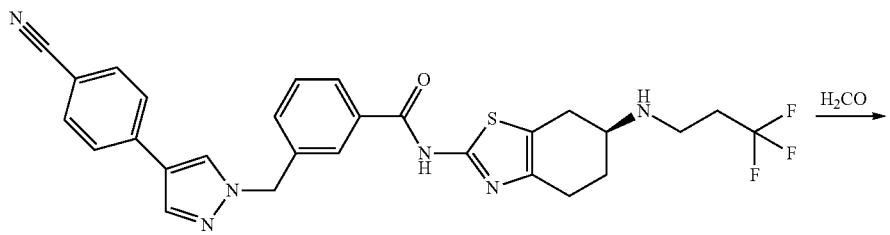

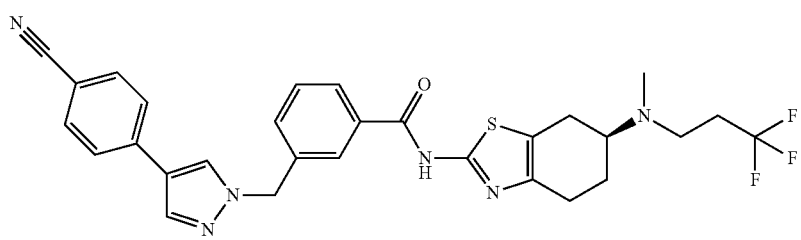

30

Stir a solution of 3-[4-(4-cyano-phenyl)-pyrazol-1-ylmethyl]-N—[(S)-6-(3,3,3-trifluoro-propylamino)-4,5,6,7-tetrahydro-benzothiazol-2-yl]-benzamide (0.063 g, 0.11 mmol) and formaldehyde solution (0.08 mL, 1.14 mmol, 37 wt % in $H_2O$) and sodium cyanoborohydride (0.014 g, 0.23 mmol) in 1 mL 20% MeOH/$CH_2Cl_2$ overnight at room temperature in a capped flask. Concentrate the mixture, add aq. $H_2O$ and extract the product 4×EtOAc, washed 3×$H_2O$. Dry the mixture with a drying agent and concentrate. Purify the product on a prep plate eluting with 5% MeOH/$CH_2Cl_2$ which affords 0.052 g, 80% yield of 3-[4-(4-cyano-phenyl)-pyrazol-1-ylmethyl]-N-{(S)-6-[methyl-(3,3,3-trifluoro-propyl)-amino]-4,5,6,7-tetrahydro-benzothiazol-2-yl}-benzamide as a clear resin. MS, electrospray 565.71 (M+H), room temperature 1.60 min. The following compound is prepared analogously (Example 11)

Compound 31: 3-[4-(4-Cyano-phenyl)-[1,2,3]triazol-1-ylmethyl]-N-{(S)-6-[methyl-(3,3,3-trifluoro-propyl)-amino]-4,5,6,7-tetrahydro-benzothiazol-2-yl}-benzamide. MS, electrospray 566.71 (M+H), rt 1.48 min.

Example 12

N—[(S)-6-(2-Cyano-ethylamino)-4,5,6,7-tetrahydro-benzothiazol-2-yl]-3-[4-(4-cyano-phenyl)-pyrazol-1-ylmethyl]-benzamide (Compound 33)

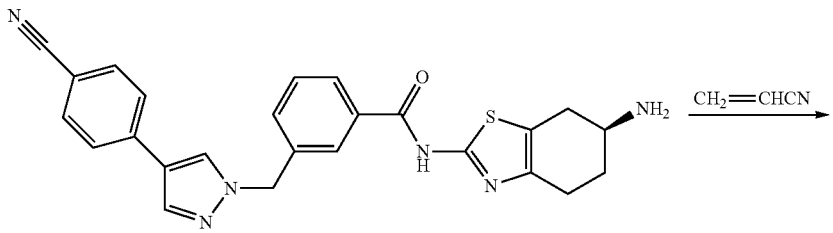

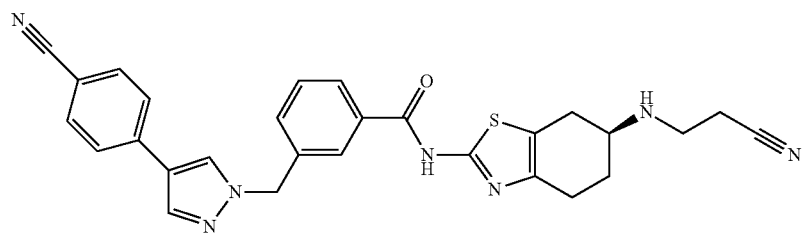

33

Heat a solution of N—((S)-6-amino-4,5,6,7-tetrahydro-benzothiazol-2-yl)-3-[4-(4-cyano-phenyl)-pyrazol-1-ylmethyl]-benzamide (0.22 g, 0.48 mmol) and acrylonitrile (0.32 mL, 4.84 mmol) in 5 mL alcohol at 75° C. overnight, giving some precipitate and some dark residue on the glass. Add another 10 eq. of acrylonitrile (0.319 ml) and heating is continued another 24 h. Cool the mixture to room temperature. Filter the precipitate to afford 0.060 g of a solid and concentrate the filtrate to afford an additional 0.26 g of a brown resin. Combine the crude material and purify on prep plates eluting with 8% MeOH/CH$_2$Cl$_2$/0.5% NH$_4$OH to afford 0.04 g of impure product. Repeat the purification on prep plates in 4% MeOH to get 0.03 g, yielding impure material. Repeat the prep plate purification eluting with 60% acetone/hexane to get 0.021 g, 9% yield of N—[(S)-6-(2-cyano-ethylamino)-4,5,6,7-tetrahydro-benzothiazol-2-yl]-3-[4-(4-cyano-phenyl)-pyrazol-1-ylmethyl]-benzamide as a clear oil. MS, electrospray 508.64 (M+H), rt 1.41 min.

The following compounds are prepared analogously to above (Example 12)

Compound 53: N-{(S)-6-[(2-Cyano-ethyl)-methyl-amino]-4,5,6,7-tetrahydro-benzothiazol-2-yl}-3-[4-(4-cyano-phenyl)-pyrazol-1-ylmethyl]-benzamide MS, electrospray 522.68 (M+H), rt 1.51 min.

Compound 13: N—[(S)-6-(2-Cyano-ethylamino)-4,5,6,7-tetrahydro-benzothiazol-2-yl]-3-[4-(4-cyano-phenyl)-[1,2,3]triazol-1-ylmethyl]-benzamide MS, electrospray 509.66 (M+H), rt 1.38 min.

Compound 32: N-{(S)-6-[(2-Cyano-ethyl)-methyl-amino]-4,5,6,7-tetrahydro-benzothiazol-2-yl}-3-[4-(4-cyano-phenyl)-[1,2,3]triazol-1-ylmethyl]-benzamide. MS, electrospray 523.69 (M+H), rt 1.36 min.

Example 13

3-[4-(4-Cyano-phenyl)-pyrazol-1-ylmethyl]-N-[6-((2R,6S)-2,6-dimethyl-morpholin-4-yl)-4,5,6,7-tetrahydro-benzothiazol-2-yl]-benzamide (Compound 26)

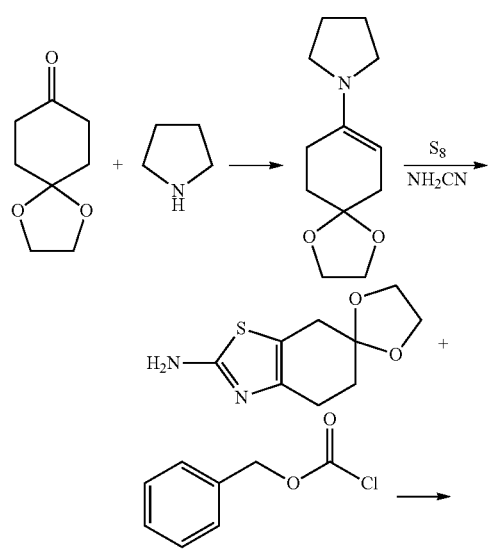

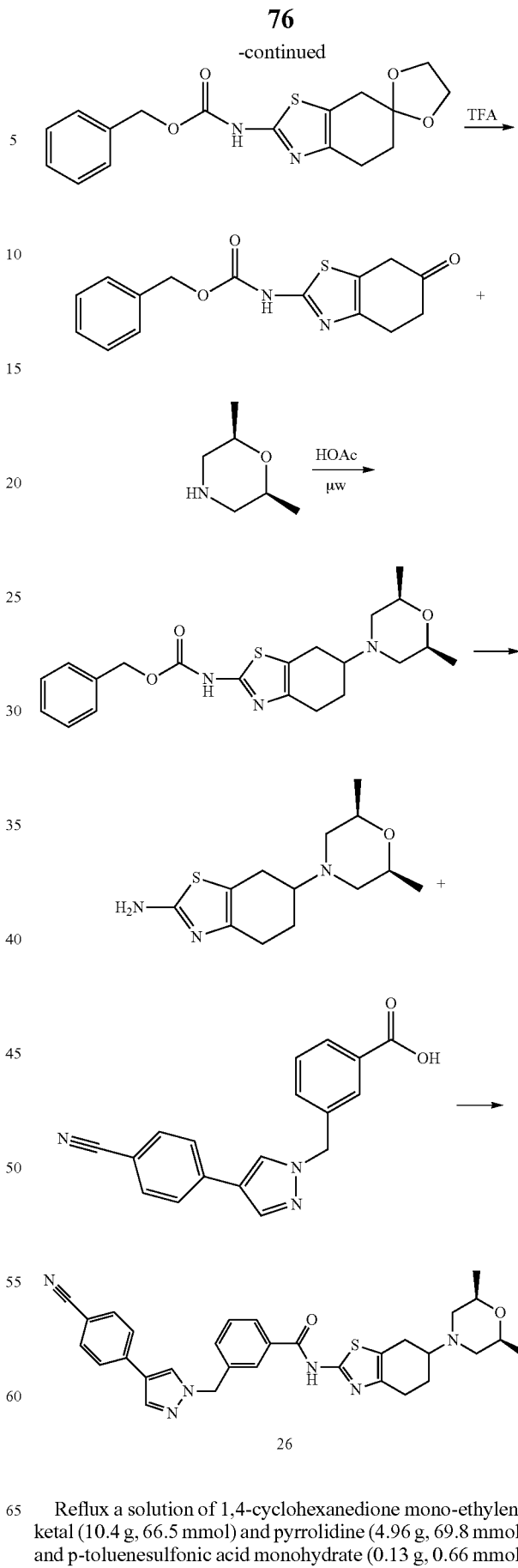

Reflux a solution of 1,4-cyclohexanedione mono-ethylene ketal (10.4 g, 66.5 mmol) and pyrrolidine (4.96 g, 69.8 mmol) and p-toluenesulfonic acid monohydrate (0.13 g, 0.66 mmol)

in 50 mL cyclohexane overnight with a Dean-Stark trap and drying tube. Filter the mixture, wash with Et$_2$O and concentrate the brown filtrate to afford 4.20 g of 1-(1,4-dioxa-spiro [4.5]dec-7-en-8-yl)-pyrrolidine as brown oil Stir a solution of cyanamide (2.80 g, 66.5 mmol) in 3 mL MeOH and add a solution of 1-(1,4-dioxa-spiro[4.5]dec-7-en-8-yl)-pyrrolidine (4.20 g, 66.5 mmol) and sulfur (2.13 g, 8.31 mmol) in 15 mL MeOH overnight at room temperature. Concentrate the mixture, dissolve in EtOAc and wash with H$_2$O. Extract the aqueous phase 2×EtOAc and wash with H$_2$O. Combine the organics and wash 3×aq. NH$_4$Cl and 1×H$_2$O. Re-extract aqueous phase with EtOAc, and wash with aq. NH$_4$Cl and H$_2$O. Combine organics, dry with drying agent and concentrate to give a dark resin. Triturate with Et$_2$O to afford 7.83 g, 56% yield of 2-amino-6-(1,4-dioxa-spiro)-4,5,6,7-tetrahydrobenzothiazole as a solid.

Add benzyl chloroformate (4.25 mL, 39.3 mmol) dropwise to a solution of 2-amino-6-(1,4-dioxa-spiro)-4,5,6,7-tetrahydrobenzothiazole (7.59 g, 35.8 mmol) and N,N-diisopropylethylamine (6.85 mL, 39.3 mmol) in 115 ml THF at 4° C. Stir the mixture 0.5 h in the cold warming to room temperature under Ar overnight. Concentrate the mixture and dissolve the residue in EtOAc. Wash with 1×H$_2$O and 3×aq. NH$_4$Cl. Re-extract aqueous phase with 2×EtOAc. Wash the combined organics with aq. Na$_2$CO$_3$, dry with a drying agent and concentrate to afford 11.0 g of a dark brown-resin. Purify by flash-chromatography eluting with CH$_2$Cl$_2$ to obtain 13.4 g of impure product. Triturate with acetone and filter to afford 8.90 g, 39% yield of (6-(1,4-dioxa-spiro)-4,5,6,7-tetrahydrobenzothiazol-2-yl)-carbamic acid benzyl ester as a solid.

Stir a solution of (6-(1,4-dioxa-spiro)-4,5,6,7-tetrahydrobenzothiazol-2-yl)-carbamic acid benzyl ester (8.88 g, 25.6 mmol) in 40 mL TFA/8 mL H$_2$O for 2.5 hr at 65° C. Concentrate the mixture, add aq. Na$_2$CO$_3$ and filter the product. Wash with H$_2$O and Et$_2$O and dry in vacuo at 50° C. overnight to afford 6.76 g, 87% of (6-oxo-4,5,6,7-tetrahydrobenzothiazol-2-yl)-carbamic acid benzyl ester as solid.

Purge a thick suspension of (6-oxo-4,5,6,7-tetrahydrobenzothiazol-2-yl)-carbamic acid benzyl ester (0.25 g, 0.83 mmol) and cis-2,6-dimethylmorpholine (0.48 g, 4.14 mmol) in 10 mL 1,2-dichloroethane and 0.2 mL AcOH with N$_2$ Heat the mixture for 15 min at 120° C. in a microwave reactor, resulting in a solution. Add sodium cyanoborohydride (0.10 g, 1.65 mmol) stir for 1 h. Wash the mixture with aq. Na$_2$CO$_3$, extract 3×CH$_2$Cl$_2$, dry with drying agent and concentrate. Dissolve the residue in EtOAc, wash 3×aq. NH$_4$Cl, and 1×aq. Na$_2$CO$_3$, dry with drying agent and concentrate to give 0.55 g of an oil. Purify on prep plates eluting with 5% MeOH/CH$_2$Cl$_2$ to afford 0.19 g, 58% yield of [6-((2S,6R)-2,6-dimethyl-morpholin-4-yl)-4,5,6,7-tetrahydro-benzothiazol-2-yl]-carbamic acid benzyl ester.

Stir a solution of [6-((2S,6R)-2,6-dimethyl-morpholin-4-yl)-4,5,6,7-tetrahydro-benzothiazol-2-yl]-carbamic acid benzyl ester (0.16 g, 0.40 mmol) in 1.5 mL 33% HBr/AcOH for 1 h at 50° C. Dilute the mixture with Et$_2$O resulting in a precipitate. Filter the precipitate, wash with ether, and air dry. Suspend the solid in Na$_2$CO$_3$, extract 6×CH$_2$Cl$_2$, dry with drying agent, and concentrate.

Purify on a prep plate eluting 10% MeOH/CH$_2$Cl$_2$/1% NH$_4$OH affording 0.044 g, 41% yield of 6-(2S,6R)-2,6-dimethyl-morpholin-4-yl)-4,5,6,7-tetrahydro-benzothiazol-2-ylamine as a resin.

Couple 6-((2S,6R)-2,6-dimethyl-morpholin-4-yl)-4,5,6,7-tetrahydro-benzothiazol-2-ylamine with 3-[4-(4-cyano-phenyl)-pyrazol-1-ylmethyl]-benzoic acid as described above in Example 9 to give 3-[4-(4-cyano-phenyl)-pyrazol-1-ylmethyl]-N-[6-((2R,6S)-2,6-dimethyl-morpholin-4-yl)-4,5,6,7-tetrahydro-benzothiazol-2-yl]-benzamide. MS, electrospray 553.78 (M+H), rt 1.56 min.

The following compound is prepared analogously (Example 13)

Compound 27: 3-[4-(4-Cyano-phenyl)-[1,2,3]triazol-1-ylmethyl]-N-[6-((2S,6R)-2,6-dimethyl-morpholin-4-yl)-4,5,6,7-tetrahydro-benzothiazol-2-yl]-benzamide. MS, electrospray 554.73 (M+H), rt 1.49 min.

The following compounds are prepared analogously by reductive amination of (6-oxo-4,5,6,7-tetrahydrobenzothiazol-2-yl)-carbamic acid benzyl ester with an appropriate amine, de-protection, coupling with a carboxylic acid, and reductive methylation in some cases as described above (Example 10)

Compound 51: 3-[4-(4-Cyano-phenyl)-pyrazol-1-ylmethyl]-N-[6-(2,2-difluoro-ethylamino)-4,5,6,7-tetrahydro-benzothiazol-2-yl]-benzamide. MS, electrospray 519.71 (M+H), rt 1.54 min.

Compound 59: 3-[4-(4-Cyano-phenyl)-pyrazol-1-ylmethyl]-N-{6-[(2,2-difluoro-ethyl)-methyl-amino]-4,5,6,7-tetrahydro-benzothiazol-2-yl}-benzamide. MS, electrospray 533.70 (M+H), rt 1.61 min.

Compound 52: 3-[4-(4-Cyano-phenyl)-[1,2,3]triazol-1-ylmethyl]-N-[6-(2,2-difluoro-ethylamino)-4,5,6,7-tetrahydro-benzothiazol-2-yl]-benzamide. MS, electrospray 520.71 (M+H), rt 1.46 min.

Compound 60: 3-[4-(4-Cyano-phenyl)-[1,2,3]triazol-1-ylmethyl]-N-{6-[(2,2-difluoro-ethyl)-methyl-amino]-4,5,6,7-tetrahydro-benzothiazol-2-yl}-benzamide. MS, electrospray 534.68 (M+H), rt 1.50 min.

Compound 67: 3-[4-(4-Cyano-phenyl)-pyrazol-1-ylmethyl]-N-[6-(cyclopropyl-methyl-amino)-4,5,6,7-tetrahydro-benzothiazol-2-yl]-benzamide. MS, electrospray 509.74 (M+H), rt 1.52 min.

Compound 68: 3-[4-(4-Cyano-phenyl)-[1,2,3]triazol-1-ylmethyl]-N-[6-(cyclopropyl-methyl-amino)-4,5,6,7-tetrahydro-benzothiazol-2-yl]-benzamide. MS, electrospray 510.68 (M+H), rt 1.48 min.

Compound 69: 3-[4-(4-Cyano-phenyl)-pyrazol-1-ylmethyl]-N-[6-(2,3-dihydro-indol-1-yl)-4,5,6,7-tetrahydro-benzothiazol-2-yl]-benzamide. MS, electrospray 557.53 (M+H), rt 2.12 min.

Compound 70: 3-[4-(4-Cyano-phenyl)-[1,2,3]triazol-1-ylmethyl]-N-[6-(2,3-dihydro-indol-1-yl)-4,5,6,7-tetrahydro-benzothiazol-2-yl]-benzamide. MS, electrospray 558.64 (M+H), rt 2.08 min.

Compound 71: 3-[4-(4-Cyano-phenyl)-pyrazol-1-ylmethyl]-N-[6-(3,3-difluoro-piperidin-1-yl)-4,5,6,7-tetrahydro-benzothiazol-2-yl]-benzamide. MS, electrospray 559.72 (M+H), rt 1.59 min.

Compound 72: 3-[4-(4-Cyano-phenyl)-[1,2,3]triazol-1-ylmethyl]-N-[6-(3,3-difluoro-piperidin-1-yl)-4,5,6,7-tetrahydro-benzothiazol-2-yl]-benzamide. MS, electrospray 560.68 (M+H), rt 1.52 min.

Compound 73: 3-[4-(4-Cyano-phenyl)-pyrazol-1-ylmethyl]-N-[6-(3,3-difluoro-pyrrolidin-1-yl)-4,5,6,7-tetrahydro-benzothiazol-2-yl]-benzamide. MS, electrospray 545.68 (M+H), rt 1.55 min.

Compound 74: 3-[4-(4-Cyano-phenyl)-[1,2,3]triazol-1-ylmethyl]-N-[6-(3,3-difluoro-pyrrolidin-1-yl)-4,5,6,7-tetrahydro-benzothiazol-2-yl]-benzamide. MS, electrospray 546.70 (M+H), rt 1.48 min.

Example 14

Synthesis of 3-[4-(4-Cyano-phenyl)-[1,2,3]triazol-1-ylmethyl]-N—[(R)-6-(2-methoxy-ethylamino)-4,5,6,7-tetrahydro-benzothiazol-2-yl]-benzamide (Compound 65) and 3-[4-(4-Cyano-phenyl)-[1,2,3]triazol-1-ylmethyl]-N-{(R)-6-[(2-methoxy-ethyl)-methyl-amino]-4,5,6,7-tetrahydro-benzothiazol-2-yl}-benzamide (Compound 66)

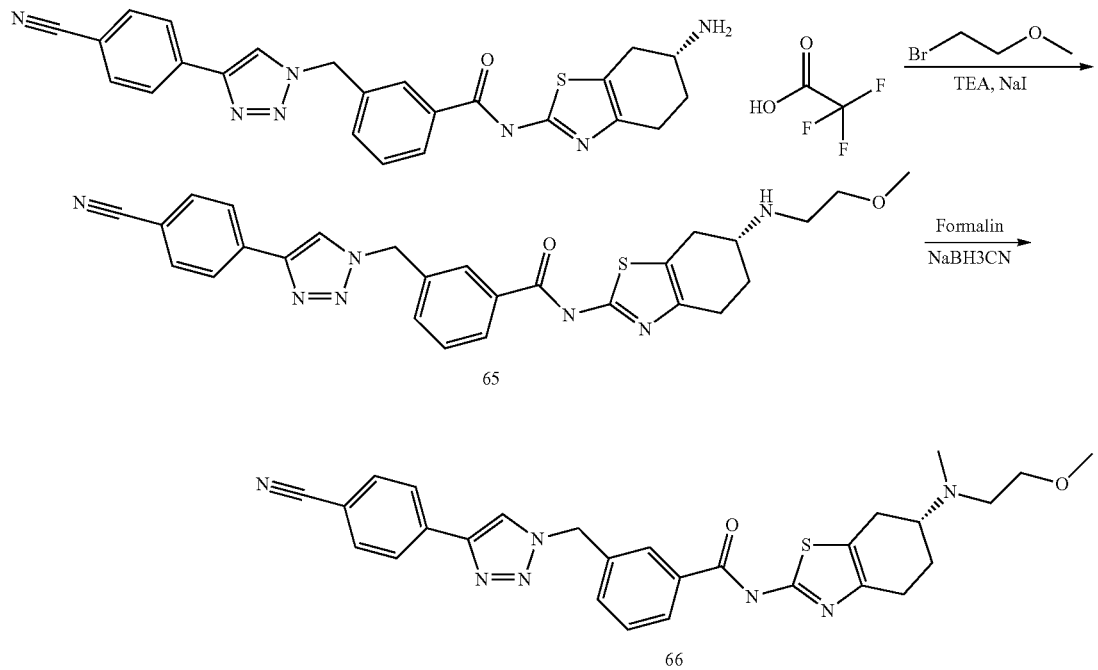

React 3-[4-(4-cyano-phenyl)-[1,2,3]triazol-1-ylmethyl]-benzoic acid and ((R)-2-amino-4,5,6,7-tetrahydro-benzothiazol-6-yl)-carbamic acid tert-butyl ester under TBTU coupling conditions as described in Example 1 to give ((R)-2-{3-[4-(4-cyano-phenyl)-1,2,3-triazol-1-ylmethyl]-benzoylamino}-4,5,6,7-tetrahydro-benzothiazol-6-yl)-carbamic acid tert-butyl ester React ((R)-2-{3-[4-(4-cyano-phenyl)-1,2,3-triazol-1-ylmethyl]-benzoylamino}-4,5,6,7-tetrahydro-benzothiazol-6-yl)-carbamic acid tert-butyl ester as in Example 9 to give N—((R)-6-amino-4,5,6,7-tetrahydro-benzothiazol-2-yl)-3-[4-(4-cyano-phenyl)-1,2,3-triazol-1-ylmethyl]-benzamide trifluoroacetate.

Add to a solution of N—((R)-6-amino-4,5,6,7-tetrahydro-benzothiazol-2-yl)-3-[4-(4-cyano-phenyl)-1,2,3-triazol-1-ylmethyl]-benzamide trifluoroacetate (0.92 g, 1.61 mmol), bromoethyl methyl ether (0.22 g, 1.61 mmol), triethylamine (0.33 g, 3.22 mmol) and sodium iodide (0.02 mg, 0.16 mmol) in 8 mL of EtOH. Heat the reaction mixture at 110° C. under microwave irradiation for 5 h. Filter the mixture, concentrate and purify via preparative HPLC to give 0.32 g, 39% yield of 3-[4-(4-cyano-phenyl)-[1,2,3]triazol-1-ylmethyl]-N—[(R)-6-(2-methoxy-ethylamino)-4,5,6,7-tetrahydro-benzothiazol-2-yl]-benzamide as white foam. MS, ES+ 514.45 (M+H), rt 5.27 min Add to a solution of 3-[4-(4-cyano-phenyl)-[1,2,3]triazol-1-ylmethyl]-N—[(R)-6-(2-methoxy-ethylamino)-4,5,6,7-tetrahydro-benzothiazol-2-yl]-benzamide (0.13 g, 0.20 mmol) in 5 mL MeOH formalin (0.3 mL) and sodium cyanoborohydride (51 mg, 0.82 mmol). Stir the mixture at room temperature for 2 h. Add sat. NH$_4$Cl to the mixture to quench any unreacted sodium cyanoborohydride. Concentrate the mixture, concentrate and purify via preparative HPLC to afford 0.06 g, 58% yield of 3-[4-(4-cyano-phenyl)-[1,2,3]triazol-1-ylmethyl]-N-{(R)-6-[(2-methoxy-ethyl)-methyl-amino]-4,5,6,7-tetrahydro-benzothiazol-2-yl}-benzamide. MS, ES+ 528.44 (M+H), rt 5.33 min The following compounds were prepared analogously (Example 14)

Compound 11: 3-[4-(4-Cyano-phenyl)-pyrazol-1-ylmethyl]-N-[6-(4-methyl-piperazin-1-yl)-4,5,6,7-tetrahydro-benzothiazol-2-yl]-benzamide. MS, ES+ 538.71 (M+H), rt 1.36 min.

Compound 12: 3-[4-(4-Cyano-phenyl)-pyrazol-1-ylmethyl]-N-[6-(4-cyclopropyl-piperazin-1-yl)-4,5,6,7-tetrahydro-benzothiazol-2-yl]-benzamide. MS, ES+ 564.71 (M+H), rt 1.49 min.

Compound 14: 3-[4-(4-Cyano-phenyl)-pyrazol-1-ylmethyl]-N-{6-[(2-methoxy-ethyl)-methyl-amino]-4,5,6,7-tetrahydro-benzothiazol-2-yl}-benzamide. MS, ES+ 527.47 (M+H), rt 5.46 min.

Compound 23: 3-[4-(4-Cyano-phenyl)-[1,2,3]triazol-1-ylmethyl]-N-[6-(4-methyl-piperazin-1-yl)-4,5,6,7-tetrahydro-benzothiazol-2-yl]-benzamide. MS, ES+ 539.36 (M+H), rt 5.07 min.

Compound 24: 3-[4-(4-Cyano-phenyl)-[1,2,3]triazol-1-ylmethyl]-N-{6-[(2-methoxy-ethyl)-methyl-amino]-4,5,6,7-tetrahydro-benzothiazol-2-yl}-benzamide. MS, ES+ 528.44 (M+H), rt 5.32 min.

Compound 25: 3-[4-(4-Cyano-phenyl)-pyrazol-1-ylmethyl]-N—[(S)-6-(4-methyl-piperazin-1-yl)-4,5,6,7-tetrahydro-benzothiazol-2-yl]-benzamide. MS, ES+ 538.46 (M+H), rt 5.26 min.

Compound 45: 3-[4-(4-Cyano-phenyl)-pyrazol-1-ylmethyl]-N—[(S)-6-(2-methoxy-ethylamino)-4,5,6,7-tetrahydro-benzothiazol-2-yl]-benzamide. MS, ES+ 513.73 (M+H), rt 1.50 min.

Compound 46: 3-[4-(4-Cyano-phenyl)-pyrazol-1-ylmethyl]-N-{(S)-6-[(2-methoxy-ethyl)-methyl-amino]-4,5,6,7-tetrahydro-benzothiazol-2-yl}-benzamide. MS, ES+ 527.69 (M+H), rt 1.48 min.

Compound 48: 3-[4-(4-Cyano-phenyl)-[1,2,3]triazol-1-ylmethyl]-N—[(S)-6-(2-methoxy-ethylamino)-4,5,6,7-tetrahydro-benzothiazol-2-yl]-benzamide. MS, ES+ 514.65 (M+H), rt 1.31 min.

Compound 49: 3-[4-(4-Cyano-phenyl)-[1,2,3]triazol-1-ylmethyl]-N-{(S)-6-[(2-methoxy-ethyl)-methyl-amino]-4,5,6,7-tetrahydro-benzothiazol-2-yl}-benzamide. MS, ES+ 528.44 (M+H), rt 5.26 min.

Compound 54: N—((R)-6-Amino-4,5,6,7-tetrahydro-benzothiazol-2-yl)-3-[4-(4-cyano-phenyl)-pyrazol-1-ylmethyl]-benzamide. MS, ES+ 455.40 (M+H), rt 5.34 min.

Compound 55: N-{(S)-6-[Bis-(2-methoxy-ethyl)-amino]-4,5,6,7-tetrahydro-benzothiazol-2-yl}-3-[4-(4-cyano-phenyl)-[1,2,3]triazol-1-ylmethyl]-benzamide. MS, ES+ 572.50 (M+H), rt 5.43 min.

Compound 57: 3-[4-(4-Cyano-phenyl)-pyrazol-1-ylmethyl]-N—[(R)-6-(2-methoxy-ethylamino)-4,5,6,7-tetrahydro-benzothiazol-2-yl]-benzamide. MS, ES+ 513.48 (M+H), rt 5.46 min.

Compound 58: N—((R)-6-Amino-4,5,6,7-tetrahydro-benzothiazol-2-yl)-3-[4-(4-cyano-phenyl)-[1,2,3]triazol-1-ylmethyl]-benzamide. MS, ES+ 456.39 (M+H), rt 5.21 min.

Compound 64: 3-[4-(4-Cyano-phenyl)-pyrazol-1-ylmethyl]-N-{(R)-6-[(2-methoxy-ethyl)-methyl-amino]-4,5,6,7-tetrahydro-benzothiazol-2-yl}-benzamide. MS, ES+ 527.47 (M+H), rt 5.36 min.

Example 15

Synthesis of 6-(4,4-Difluoro-piperidin-1-yl)-4,5,6,7-tetrahydro-benzothiazol-2-ylamine

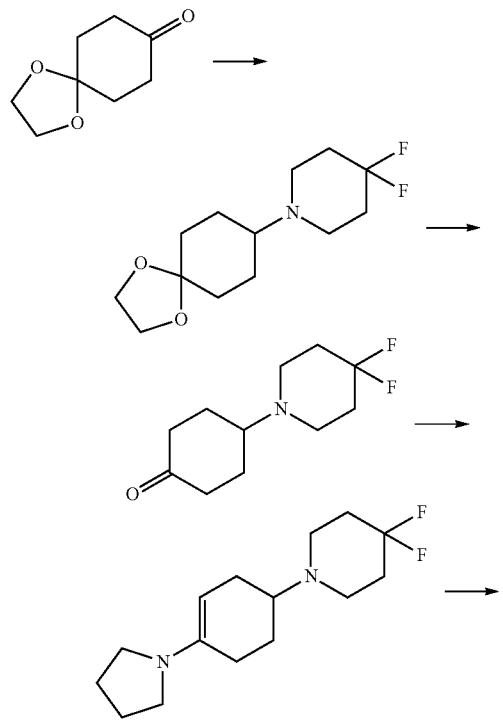

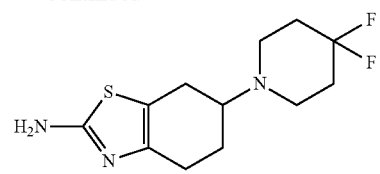

Partially dissolve a suspension of 4,4-difluoropiperidine hydrochloride (1.47 g, 9.34 mmol) in 75 mL of CH$_2$Cl$_2$ by sonication. Add AcOH (1.01 mL, 17.7 mmol), resulting in a clear solution. Add 1,4-cyclohexadione monoethylene ketal (1.38 g, 8.84 mmol) and solid sodium triacetoxyborohydride (3.00 g, 14.1 mmol). Stir the mixture for 20 h at room temperature. Adjust the pH of the mixture to 12 by the addition of 1M NaOH and extract with CH$_2$Cl$_2$. Dry the organic layer with MgSO$_4$ and evaporate to give 2.41 g, 100% yield of 1-(1,4-dioxa-spiro[4.5]dec-8-yl)-4,4-difluoro-piperidine.

Stir a solution of 1-(1,4-dioxa-spiro[4.5]dec-8-yl)-4,4-difluoro-piperidine (2.41 g, 9.22 mmol) in 4 mL of 6M hydrochloric acid at room temperature for 48 h. Neutralize the mixture with the addition of 30% NaOH solution and extract with 5×CH$_2$Cl$_2$. Dry the combined extracts with MgSO$_4$ and evaporate to give 1.93 g, 96% yield of 4-(4,4-difluoro-piperidin-1-yl)-cyclohexanone as a colorless liquid.

Heat a solution of 4-(4,4-difluoro-piperidin-1-yl)-cyclohexanone (1.93 g 8.88 mmol), pyrrolidine (0.89 mL, 10.7 mmol) and p-toluenesulfonic acid (1 crystal) in cyclohexane (50 mL) to reflux with a Dean-Stark trap for 7 h. Cool the solution and filter through a plug of cotton wool. Evaporate to give 2.31 g, 96% yield of 4,4-difluoro-1-(4-pyrrolidin-1-yl-cyclohex-3-enyl)-piperidine as an oil.

Add sulfur (0.26 g, 8.20 mmol) to a stifling solution of 4,4-difluoro-1-(4-pyrrolidin-1-yl-cyclohex-3-enyl)-piperidine (2.31 g, 8.54 mmol) in 12 mL of MeOH (12 mL) at room temperature After 15 min add cyanamide (0.40 mg, 8.54 mmol). Continue stifling for 4 days, by which time the sulfur dissolves. Evaporate the solvent and add CH$_2$Cl$_2$ to the residue. Filter undissolved particulate, wash with CH$_2$Cl$_2$ and dry to give 0.46 g, 20% yield of 6-(4,4-difluoro-piperidin-1-yl)-4,5,6,7-tetrahydro-benzothiazol-2-ylamine. Evaporate the filtrate and washings and purify by chromatography (CH$_2$Cl$_2$/20% MeOH/1% NH4OH) to provide more desired product 0.64 g, 32% yield.

6-(4-Fluoro-piperidin-1-yl)-4,5,6,7-tetrahydro-benzothiazol-2-ylamine was prepared analogously (Example 15)

Example 16

Synthesis of (S)-6-Piperidin-1-yl-4,5,6,7-tetrahydro-benzothiazol-2-ylamine dihydrobromide

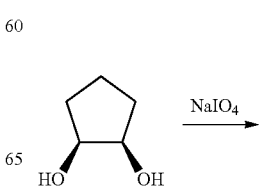

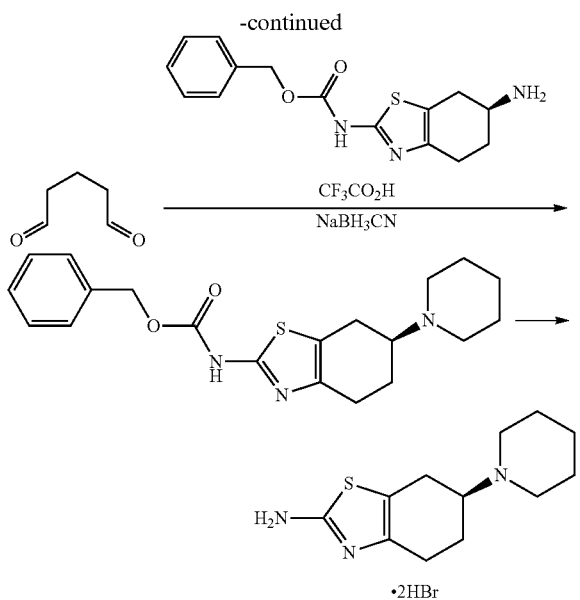

Add solid periodic acid (0.55 g, 2.40 mmol) to a solution of cyclopentane diol (245 mg, 2.40 mmol) in 2 mL water resulting in a clear solution. Stir the mixture at room temperature for 3 h. Add 2 mL of CH₃CN and neutralize with the addition of sat. NaHCO₃ solution, resulting in the formation of a precipitate. Filter the solid and wash with CH₃CN. Use the filtrate which contains the dialdehyde immediately in the next reaction.

Add (S)-6-amino-4,5,6,7-tetrahydro-benzothiazol-2-yl)-carbamic acid benzyl ester trifluoroacetate (0.10 g, 0.24 mmol) to the dialdehyde solution. Adjust the pH of the solution to 4 by adding a few drops of acetic acid and is stir for 30 min. Add sodium cyanoborohydride (0.15 g, 2.40 mmol) and stir the mixture stirred for 16 h at room temperature. Neutralize the solution by addition of Na₂CO₃ and extract with CH₂Cl₂. Dry the organic layer is with MgSO₄ and concentrate. Purify the residue with column chromatography eluting with 5-100% CH₂Cl₂/20% MeOH/1% NH4OH to give (S)-6-piperidin-1-yl-4,5,6,7-tetrahydro-benzothiazol-2-yl)-carbamic acid benzyl ester (0.08 g, 0.21 mmol).

Add (S)-6-piperidin-1-yl-4,5,6,7-tetrahydro-benzothiazol-2-yl)-carbamic acid benzyl ester (117 mg, 0.31 mmol) to a solution of HBr in acetic acid (33%, 1 mL) and stir the resulting solution at room temperature for 24 h. Add Et₂O (15 mL), resulting in the formation of a precipitate. Filter the solids and set aside. Wash the remaining semi-solid residue with two portions of Et₂O. Dissolve the residue in MeOH, and combine this solution with the bulk solid. Concentrate the solution to leave a yellow residue which crystallizes after standing for a few days to afford 0.12 g, 92% yield of (S)-6-piperidin-1-yl-4,5,6,7-tetrahydro-benzothiazol-2-ylamine dihydrobromide.

Example 17

Synthesis of 3-[4-(4-Cyano-phenyl)-pyrazol-1-ylmethyl]-N-[6-(4,4-difluoro-piperidin-1-yl)-4,5,6,7-tetrahydro-benzothiazol-2-yl]-benzamide trifluoroacetate (Compound 15)

React 3-[4-(4-cyano-phenyl)-pyrazol-1-ylmethyl]-benzoic acid and 6-(4,4-difluoro-piperidin-1-yl)-4,5,6,7-tetrahydro-benzothiazol-2-ylamine under TBTU conditions as in Example 1 to give 0.17 g, 61% yield of 3-[4-(4-Cyano-phenyl)-pyrazol-1-ylmethyl]-N-[6-(4,4-difluoro-piperidin-1-yl)-4,5,6,7-tetrahydro-benzothiazol-2-yl]-benzamide trifluoroacetate. MS, ES+ 559.68 (M+H), rt 1.47 min.

The following compounds were prepared analogously (Example 17)

Compound 18: 3-[4-(4-Cyano-phenyl)-pyrazol-1-ylmethyl]-N-[6-(4-fluoro-piperidin-1-yl)-4,5,6,7-tetrahydro-benzothiazol-2-yl]-benzamide trifluoroacetate. MS, ES+ 541.72 (M+H), rt 1.49 min.

Compound 41: 3-[4-(4-Cyano-phenyl)-1,2,3-triazol-1-ylmethyl]-N-[6-(4,4-difluoro-piperidin-1-yl)-4,5,6,7-tetrahydro-benzothiazol-2-yl]-benzamide. MS, ES+ 560.72 (M+H), rt 1.46 min.

Compound 42: 3-[4-(4-Cyano-phenyl)-1,2,3-triazol-1-ylmethyl]-N-[6-(4-fluoro-piperidin-1-yl)-4,5,6,7-tetrahydro-benzothiazol-2-yl]-benzamide MS, ES+ 542.68 (M+H), rt 1.39 min.

Compound 43: 3-[4-(4-Cyano-phenyl)-pyrazol-1-ylmethyl]-N—((S)-6-piperidin-1-yl-4,5,6,7-tetrahydro-benzothiazol-2-yl)-benzamide MS, ES+ 523.69 (M+H), rt 1.48 min.

Compound 44: 3-[4-(4-Cyano-phenyl)-1,2,3-triazol-1-ylmethyl]-N—((S)-6-piperidin-1-yl-4,5,6,7-tetrahydro-benzothiazol-2-yl)-benzamide. MS, ES+ 524.71 (M+H), rt 1.42 min.

Compound 35: 3-[4-(4-Cyano-phenyl)-imidazol-1-ylmethyl]-N-[6-(4,4-difluoro-piperidin-1-yl)-4,5,6,7-tetrahydro-benzothiazol-2-yl]-benzamide. MS, ES+ 538.22 (M+H), rt 0.58 min.

Compound 38: 3-[4-(4-Cyano-phenyl)-imidazol-1-ylmethyl]-N-[6-(4-fluoro-piperidin-1-yl)-4,5,6,7-tetrahydro-benzothiazol-2-yl]-benzamide. MS, ES+ 541.75 (M+H), rt 1.36 min.

Compound 39: 3-[4-(4-Cyano-phenyl)-imidazol-1-ylmethyl]-N-[6-(4-methyl-piperazin-1-yl)-4,5,6,7-tetrahydro-benzothiazol-2-yl]-benzamide. MS, ES+ 559.74 (M+H), rt 1.18 min.

Example 18

Synthesis of 3-[4-(4-Cyano-phenyl)-pyrazol-1-ylmethyl]-N—[(S)-6-(4-oxo-piperidin-1-yl)-4,5,6,7-tetrahydro-benzothiazol-2-yl]-benzamide (Compound 75)

Divinyl ketone is prepared from 1,5-dichloro-3-pentanone by the method of Jung et al, J. Am. Chem. Soc. 1981, 103, 6677.

Add a solution of divinyl ketone (0.08 g 1.03 mmol) in 1 mL of CH₂Cl₂ to a solution of N—((S)-6-amino-4,5,6,7-tetrahydro-benzothiazol-2-yl)-3-[4-(4-cyano-phenyl)-pyrazol-1-ylmethyl]-benzamide (0.47 g, 1.03 mmol) in 10 mL of CH₂Cl₂ and 10 mL of MeOH. Stir the solution for 3 h at room temperature and concentrate the mixture. Purify the residue via column chromatography eluting with 1-10% CH₂Cl₂/MeOH to give 0.16 g, 30% yield of 3-[4-(4-cyano-phenyl)-pyrazol-1-ylmethyl]-N—[(S)-6-(4-oxo-piperidin-1-yl)-4,5,6,7-tetrahydro-benzothiazol-2-yl]-benzamide. Both 1 cms and NMR show that the product exists as a mixture of ketone and hydrate. MS, ES+ 555.70 (M+H₂O+H), rt 1.21 min.

Example 19

Synthesis of 3-[4-(4-Cyano-phenyl)-1H-imidazol-2-ylmethyl]-N—((S)-6-morpholin-4-yl-4,5,6,7-tetrahydro-benzothiazol-2-yl)-benzamide (Compound 61)

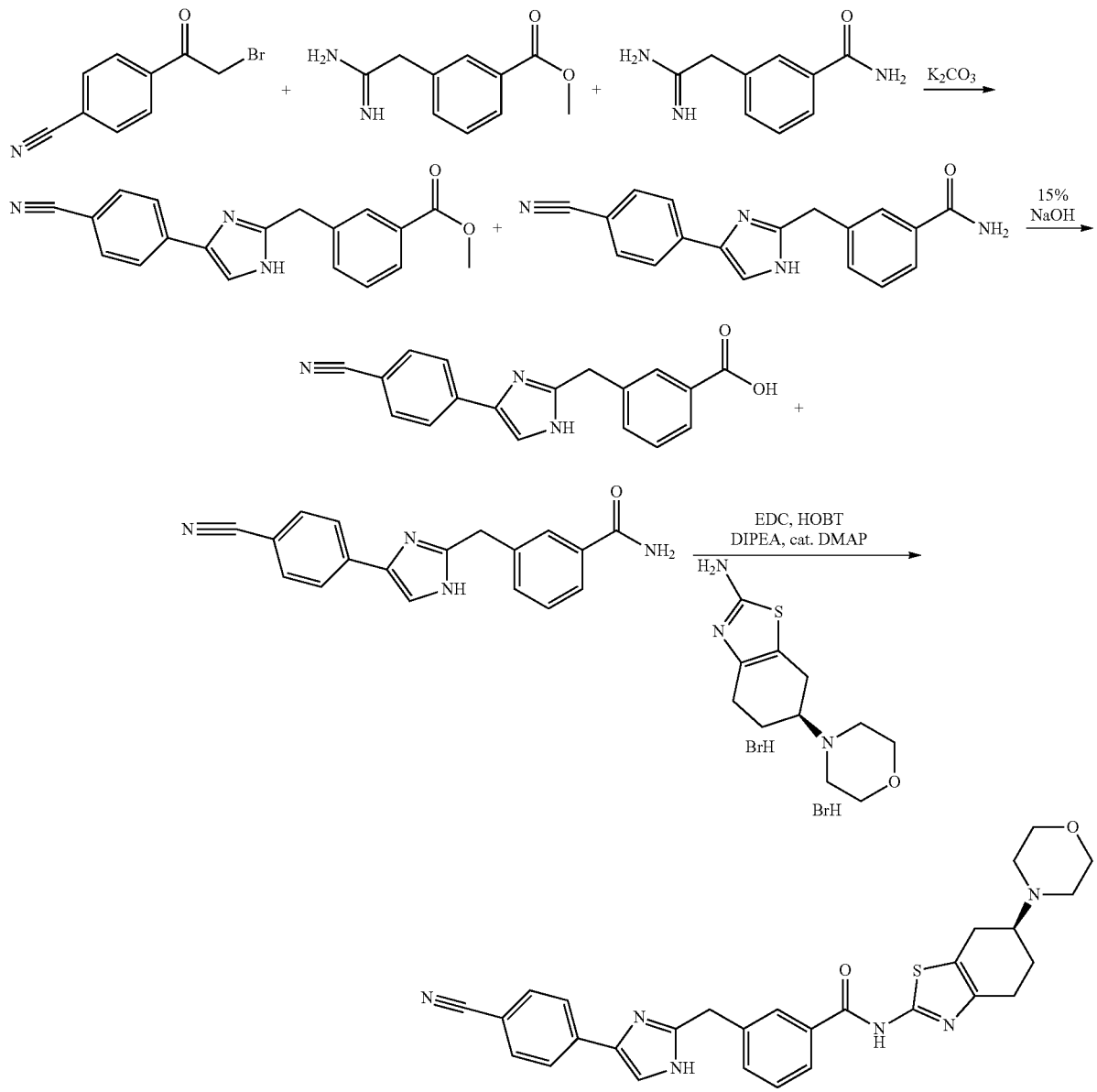

Suspend 4-(2-bromo-acetyl)-benzonitrile (0.11 g, 0.48 mmol), K$_2$CO$_3$ (0.28 g, 2.00 mmol) and a 2:1 mixture of 3-carbamimidoylmethyl-benzoic acid methyl ester hydrochloride/3-carbamimidoylmethyl-benzamide hydrochloride (0.14 g) into 5 mL of 4:1 THF/H$_2$O. Heat the mixture to reflux for 2 h. Concentrate the mixture to dryness and dissolve into 20 mL of H$_2$O. Add 5% aq HCl until pH is acidic. Extract with 2×20 mL of CH$_2$Cl$_2$. Dry organic phase with MgSO$_4$, filter and concentrate to give 0.13 g of crude 3-[4-(4-cyano-phenyl)-1H-imidazol-2-ylmethyl]-benzoic acid methyl ester and 3-[4-(4-cyano-phenyl)-1H-imidazol-2-ylmethyl]-benzamide as a purple residue.

Dissolve the mixture of crude 3-[4-(4-cyano-phenyl)-1H-imidazol-2-ylmethyl]-benzoic acid methyl ester and 3-[4-(4-cyano-phenyl)-1H-imidazol-2-ylmethyl]-benzamide (0.13 g) into 5 mL of 1:1 THF/MeOH. To this add 0.5 mL of 15% NaOH. Stir the mixture at room temperature for 2 h. Add 1 mL of 15% NaOH and stir an additional 2 h. Concentrate to dryness. Dissolve the residue into 5 mL of H$_2$O and make acidic by the addition of 5% HCl. Extract with 3×10 mL of CH$_2$Cl$_2$ and dry with MgSO$_4$. Concentrate to give 0.13 g of crude 3-[4-(4-cyano-phenyl)-1H-imidazol-2-ylmethyl]-benzoic acid and 3-[4-(4-cyano-phenyl)-1H-imidazol-2-ylmethyl]-benzamide as a purple residue.

The crude mixture was treated as described in Example 2 to provide the title compound 61. MS, ES+ 525.13 (M+H), rt 1.13 min.

Assessment of Biological Activity

Molecular Assays

The compounds of the invention may be evaluated in one or both of the following two molecular assays:

1. Luciferin-Luciferase Assay

The activity of ROCKII (1-543) kinase was measured utilizing Cambrex PKLight ATP Detection Reagent, a homogeneous assay technology using luciferin-luciferase to quantify residual ATP. The assay was performed in 384-well low-volume, white, non-binding surface microtiter plates (Corning). The assay buffer was 25 mM HEPES, pH 7.5, 10 mM $MgCl_2$, 50 mM KCl, 0.2% BSA, 0.01% CHAPS, 100 µM $Na_3VO_4$ and 0.5 mM DTT. Test compounds, dissolved in neat DMSO at 500 µg/mL, were serially diluted for dose response for a final starting concentration of 3 µg/mL in 1% DMSO of assay buffer. ROCKII (1-543) (62,408 Da) was diluted in assay buffer to a final concentration of 7.5 nM in a total volume of 15 µL. Positive controls were reaction mixtures containing no test compound; negative controls (blanks) were reaction mixtures containing no kinase. After 15 minutes of pre-incubation of the test compounds with the kinase, a mixture of ATP and peptide substrate (AKRRRLSSLRA) in assay buffer was added to each well for a final concentration of 750 nM ATP and 500 nM peptide, respectively. After 90 minutes of incubation of the kinase reaction at 28° C. temperature, 10 µL of PKLight ATP Detection Reagent (warmed to room temperature previously) was added to each well. The assay plate was incubated at room temperature for additional 15 minutes and then read on an Analyst in luminescence mode. Dose-response experiments for each of the test compounds were conducted in quadruplet. $IC_{50}$ values of test compounds represent 50% response of the positive control from the dose-response curve.

2. IMAP Assay

This assay is performed using FAM S6 substrate peptide (Catalogue #R7184) and IMAP FP Screening Express Kit detection reagents from Molecular Devices (Sunnyvale, Calif.) in IMAP kinase reaction buffer (Tris-HCl, pH 7.2, 10 mM MgCl2, 0.05% NaN3, 0.1% phosphate-free BSA) containing 1 mM DTT. Test compounds dissolved in neat DMSO at 0.3 mg/mL are serially diluted 1 to 3 for concentration response in 100% DMSO. The DMSO serial dilutions are further diluted 33.33-fold in kinase reaction buffer, and 10 µL of this buffer dilution is transferred to Corning black 96-well half area NBS plates for a final top concentration of 3 µg/mL in 1% DMSO. 10 µL aliquot of 3 nM ROCKII (1-543) diluted in kinase reaction buffer is added to each assay well for a final concentration of 1 nM kinase. 10 µL of a mixture of 600 nM FAM S6 peptide and 300 µM ATP diluted in kinase reaction buffer is added to each well for a final concentration of 200 nM peptide and 100 µM ATP. The kinase reaction mixture is incubated for 60 minutes at room temperature. Positive controls are reaction mixtures containing no test compound and negative controls (blanks) are reaction mixtures containing no kinase. The kinase reaction is stopped by addition of 60 µL IMAP progressive binding reagent (Catalog #R7284) diluted 400-fold in 1× Binding buffer A. After 30 min of incubation at room temperature, the plates are read for fluorescence polarization on Analyst Plate Reader using Ex 485 nm, Em 530 nm, and FL 505 dichroic mirror. The mP signals are converted to percent of control (POC) values using the formula:

$POC=100*(Signal-BCTRL) \div (PCTRL-BCTRL)$

Where Signal is the test well signal, BCTRL is the average of background (negative control) well signals on the plate and PCTRL is the average of positive control well signals on the plate. For the concentration-responsive compounds, POC as a function of test compound concentration is fitted to a 4-parameter logistic equation of the form:

$Y=A+(B-A)/[1+(x/C)D]$

Where A, B, C, and D are fitted parameters (parameter B is fixed at zero POC), and x and y are the independent and dependent variables, respectively. The $IC_{50}$ is determined as the inflection point parameter, C.

Representative compounds of the present invention were tested for activity in one or both of the above assays. Preferred compounds have an $IC_{50}$<1,000 nM and more preferred compounds have an $IC_{50}$<100 nM in these assays. As examples the following data were obtained for the compounds named below:

| Compound Number (Table 1) | Assay 1 $IC_{50}$ (nM) | Assay 2 $IC_{50}$ (nM) |
| --- | --- | --- |
| 1 | 4.8 | 54 |
| 2 | 2.8 | 11 |
| 3 | 2.0 | 0.67 |
| 4 |  | 0.49 |
| 5 |  | 0.20 |
| 6 | 2.0 | 1.3 |
| 7 |  | 0.40 |
| 8 |  | 1.0 |
| 10 | 2.7 | 0.87 |
| 11 |  | 0.58 |
| 13 |  | 1.0 |
| 14 |  | 0.41 |
| 15 | 4.60 | 2.4 |
| 18 | 2.2 | 0.66 |
| 20 |  | 0.47 |
| 22 | 2.2 | 1.1 |
| 23 |  | 1.3 |
| 24 | 3.1 | 2.6 |
| 25 |  | 0.65 |
| 26 | 4.3 | 3.9 |
| 27 | 3.1 | 3.9 |
| 28 |  | 0.35 |
| 29 |  | 0.73 |
| 30 | 2.1 | 7.3 |
| 31 |  | 3.1 |
| 32 | 2.9 | 2.0 |
| 33 |  | 0.35 |
| 36 | 9.9 |  |
| 40 | 3.2 | 12 |
| 41 | 7.1 | 5.8 |
| 42 | 3.4 | 1.1 |
| 43 |  | 0.37 |
| 44 | 2.4 | 0.53 |
| 45 | 2.1 | 0.35 |
| 46 |  | 0.34 |
| 48 |  | 0.32 |
| 49 | 1.7 | 0.73 |
| 51 | 1.8 |  |
| 52 | 9.4 |  |
| 53 | 1.9 |  |
| 55 | 2.3 | 6.5 |
| 56 | 2.5 | 4.0 |
| 57 | 1.9 |  |
| 58 | 2.2 |  |
| 59 | 7.3 |  |
| 64 | 2.0 |  |
| 65 | 1.9 |  |
| 66 | 6.5 |  |
| 67 | 4.5 |  |
| 68 | 7.3 |  |
| 71 | 7.2 |  |
| 73 | 8.5 |  |

Methods of Therapeutic Use

In accordance with the invention, there are provided novel methods of using the compounds of formula (I). The compounds disclosed herein effectively inhibit Rho kinase. The inhibition of Rho kinase is an attractive means for preventing and treating a variety of cardiovascular diseases or conditions associated with Rho kinase activation. Thus, the compounds are useful for the treatment of diseases and conditions as described in the Background section, including the following conditions and diseases:

hypertension, atherosclerosis, restenosis, stroke, myocardial infarction, heart failure, coronary artery disease, peripheral artery disease, coronary vasospasm, cerebral vasospasm, ischemia/reperfusion injury, pulmonary hypertension, angina, erectile dysfunction, renal disease and organ failure. As disclosed in the Background section, the compounds of the invention will also be useful for treating diseases or conditions associated with smooth muscle hyper reactivity or with activated Rho-kinase under other pathophysiological conditions. These diseases include but are not limited to asthma, glaucoma, cancer, Alzheimer's disease, multiple sclerosis, spinal cord injury, neuropathic pain, rheumatoid arthritis, psoriasis and inflammatory bowel disease.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of the formula I

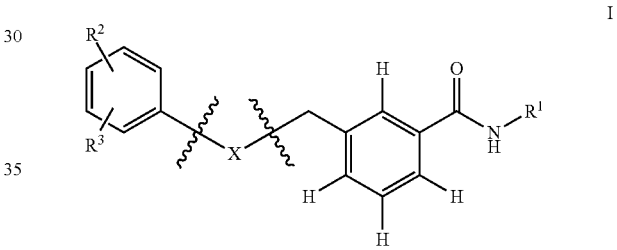

wherein:
X is selected from the group $X^a$ consisting of

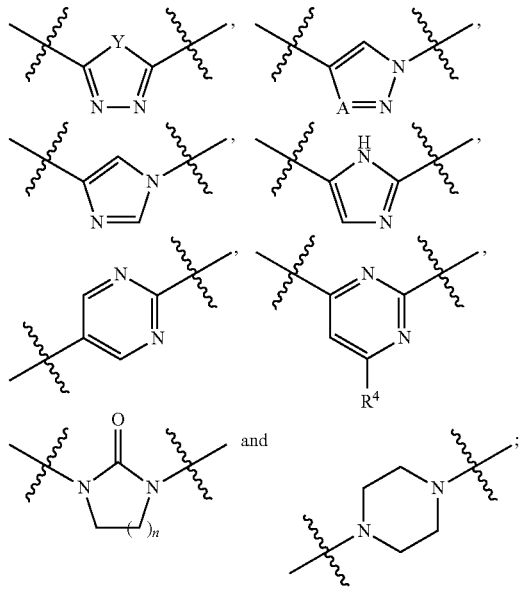

A is C or N;

Y is O or S;

$R^1$ is selected from the group $R^{1a}$ consisting of

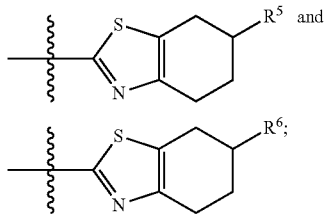

$R^2$ and $R^3$ are independently selected from H, —CH$_3$, —OCH$_3$, —F, —Cl, —C(O)NH$_2$, and —CN, provided that $R^2$ and $R^3$ are not both H;

$R^4$ is H or —CH$_3$;

$R^5$ is $C_{1-6}$alkyl;

$R^6$ is selected from a heterocyclyl group selected from piperidinyl, piperazinyl, morpholinyl, 2,3-dihydroindolyl and pyrrolidinyl, and

—N($R^7$)($R^8$), wherein the heterocyclyl group may be substituted with one to three groups selected from halogen, oxo, $C_{1-3}$alkyl and $C_{3-6}$cycloalkyl;

$R^7$ and $R^8$ are independently selected from H, $C_{1-3}$alkyl, $C_{3-6}$cycloalkyl and CO$_2$C$_{1-4}$-alkyl, wherein the $C_{1-3}$alkyl and $C_{3-6}$cycloalkyl are optionally substituted with —OCH$_3$, —CF$_3$, —CHF$_2$ or —CN; and n is 1 or 2;

or a salt thereof.

2. The compound of claim 1 wherein:

$R^2$ is selected from 3-CN and 4-CN;

$R^3$ is H; and $R^5$ is —CH$_3$;

or a salt thereof.

3. The compound of claim 1 wherein $R^1$ is

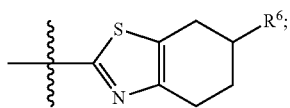

or a salt thereof.

4. The compound of claim 1 wherein:

X is selected from the group $X^b$ consisting of

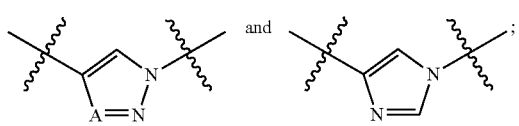

or a salt thereof.

5. The compound of claim 2 wherein:

$R^1$ is

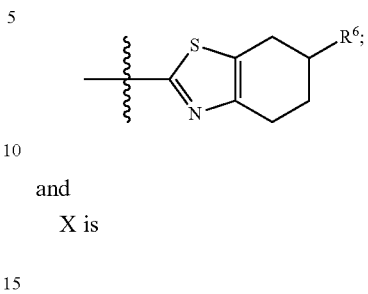

and

X is

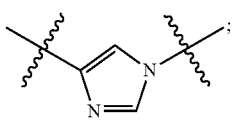 [SMILES: *c1cn(*)cn1]

or a salt thereof.

6. The compound of claim 2 wherein:

$R^1$ is

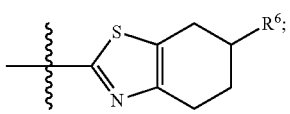

and

X is

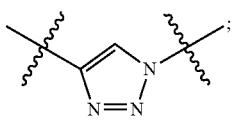 [SMILES: *c1cn(*)nn1]

or a salt thereof.

7. The compound of claim 2 wherein:

$R^1$ is

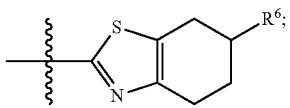

and

X is

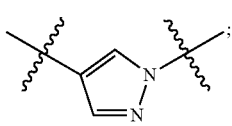 [SMILES: *c1cnn(*)c1]

or a salt thereof.

8. The compound of claim 2 wherein:
R¹ is
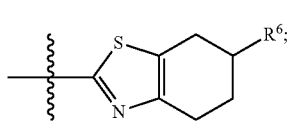
and
X is
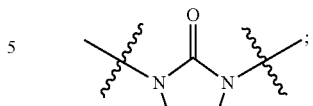
or a salt thereof.
9. A compound selected from the group consisting of
1
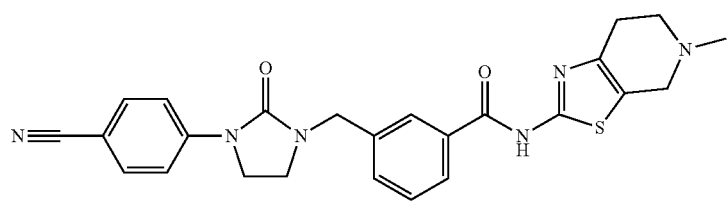
2
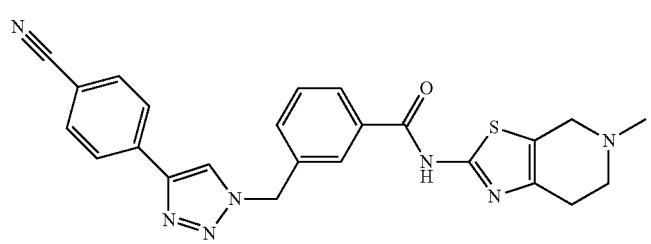
3
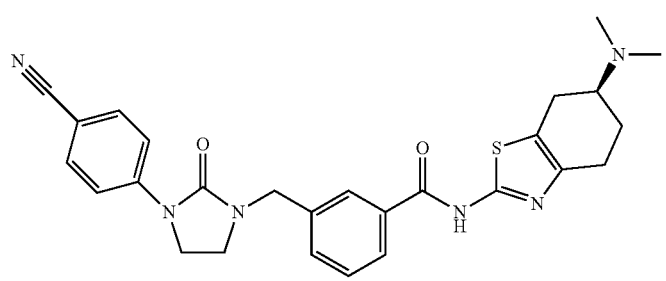
4
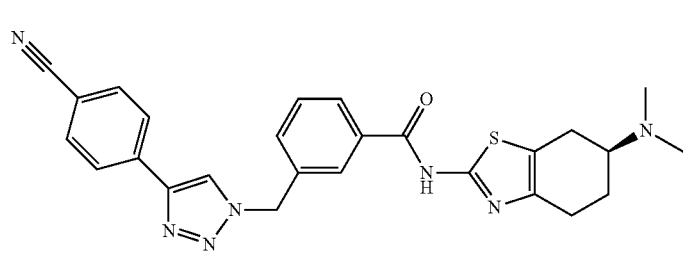
5
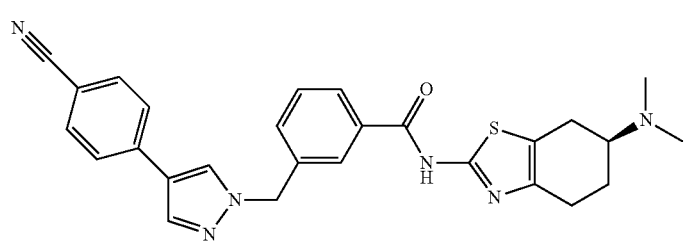

-continued
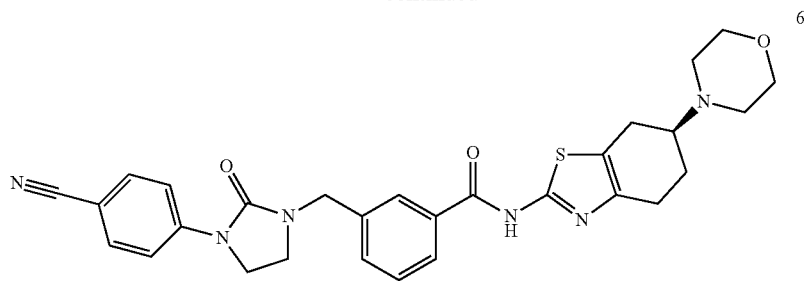
6
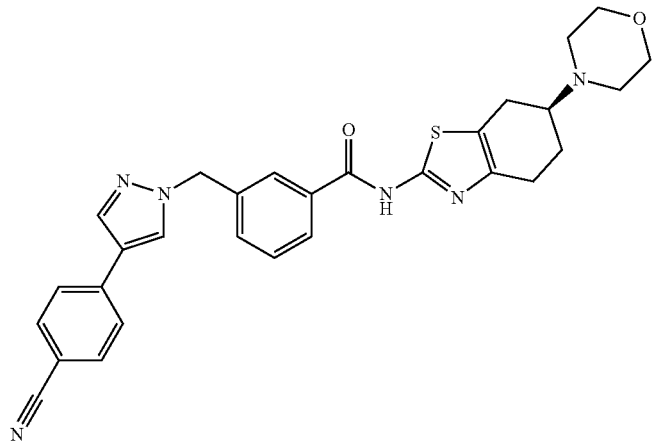
7
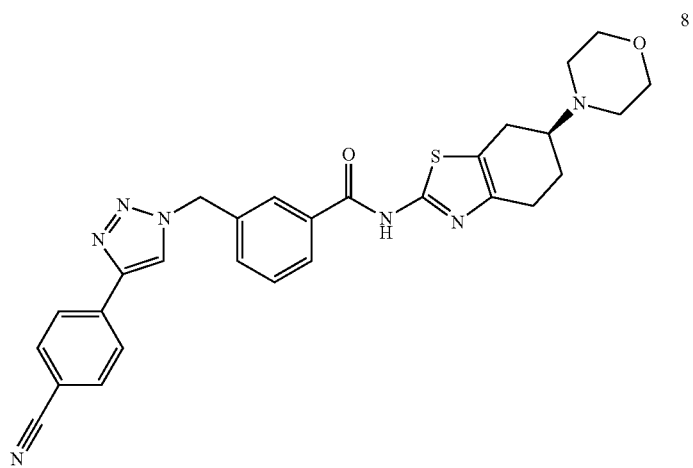
8
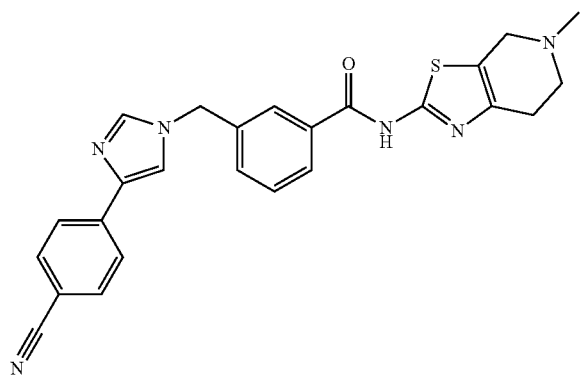
9

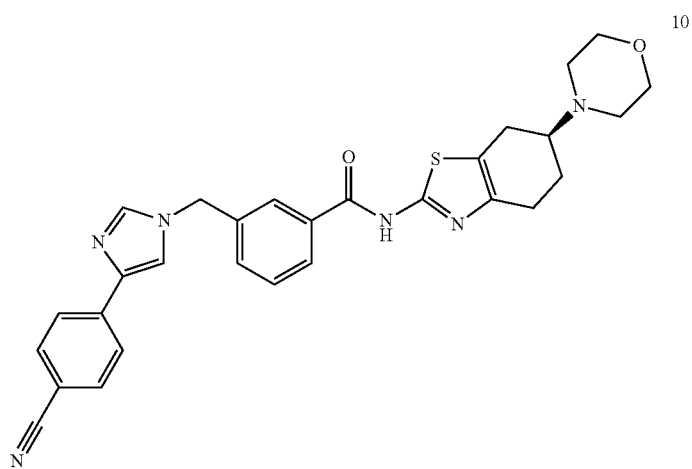
10
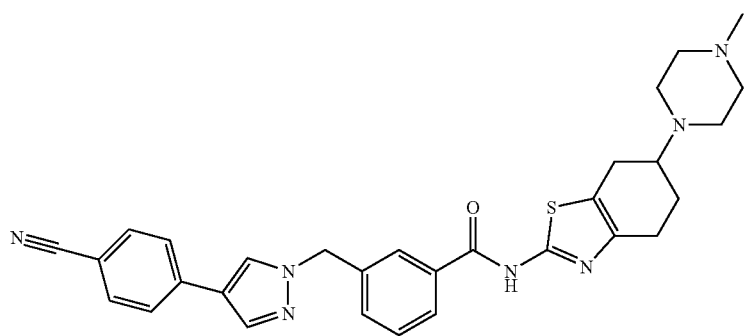
11
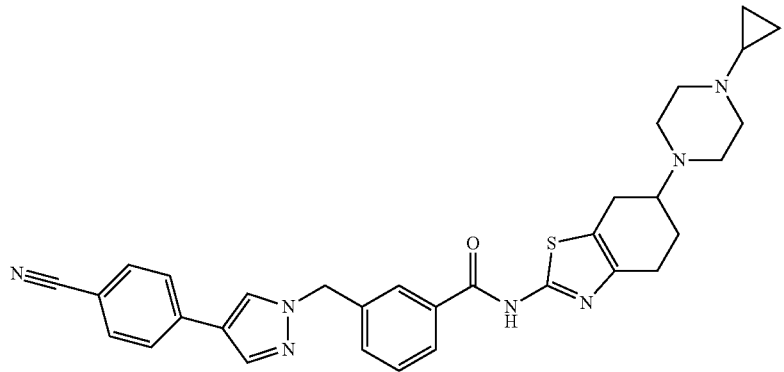
12
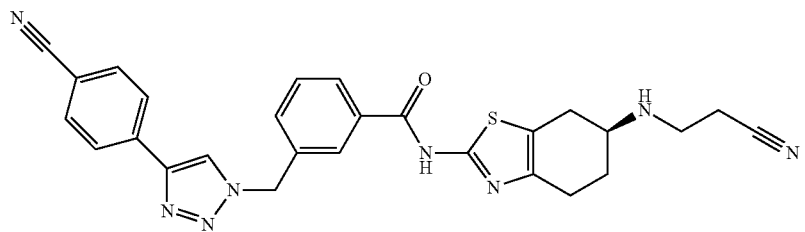
13

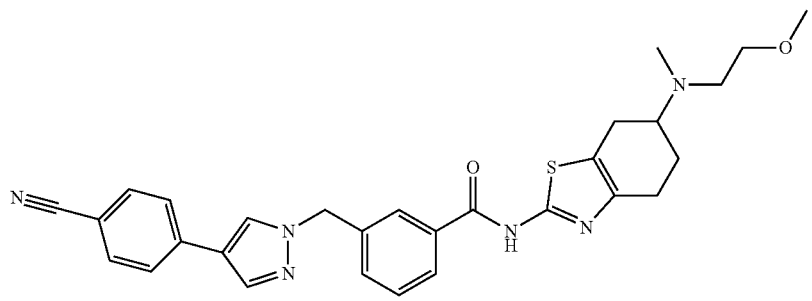
14
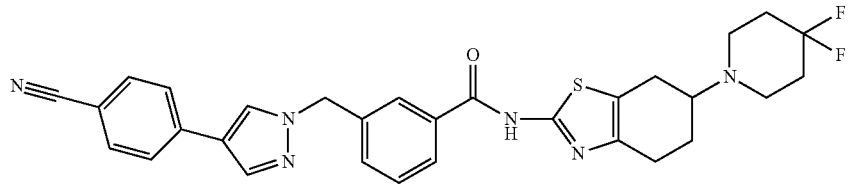
15
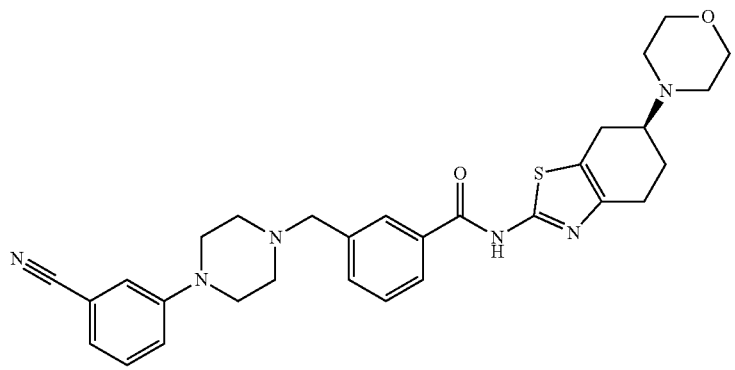
16
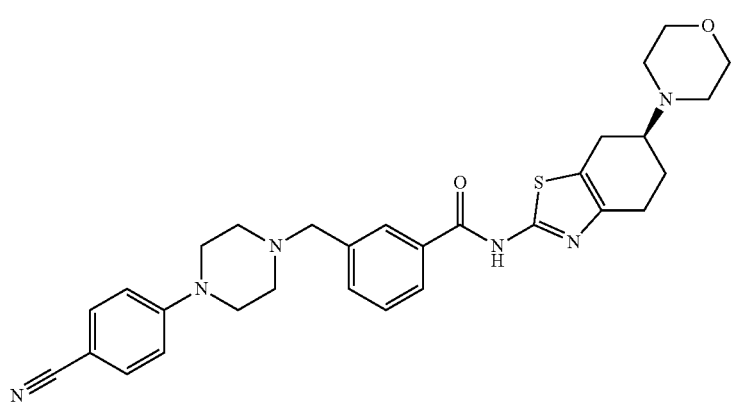
17
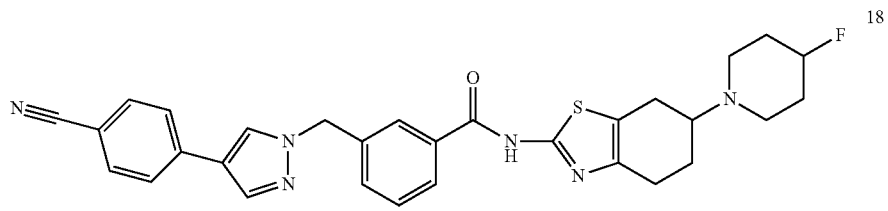
18

19
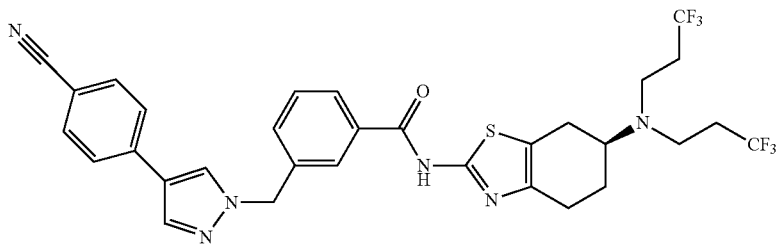
20
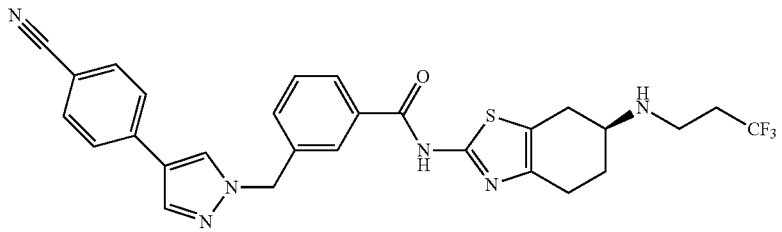
21
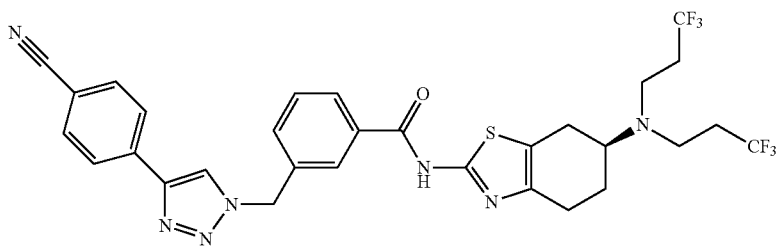
22
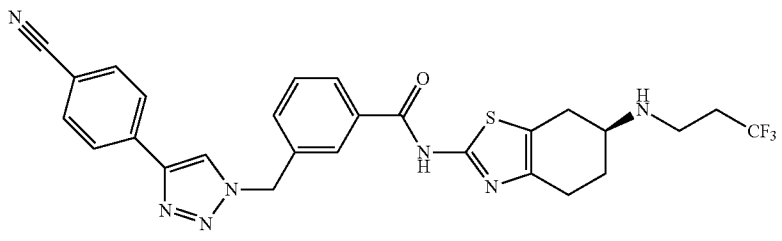
23
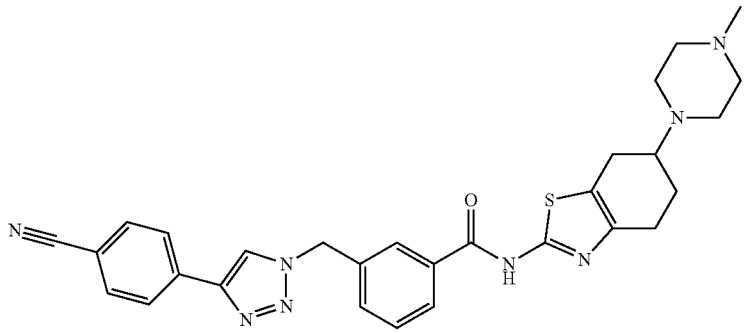
24
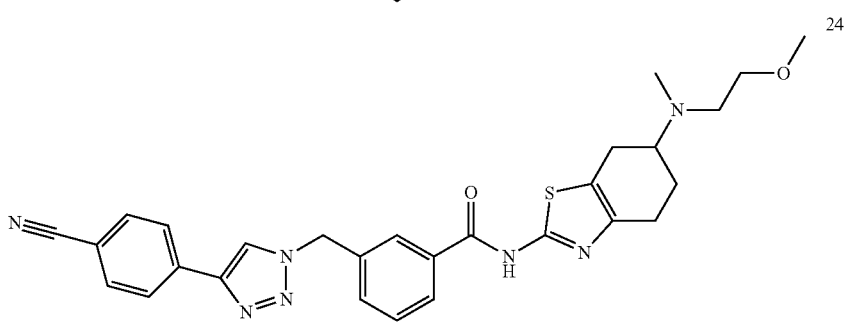

-continued
25
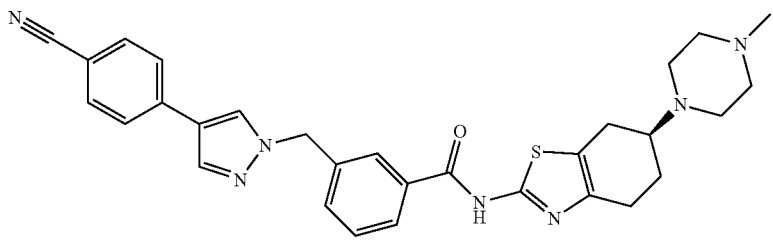
26
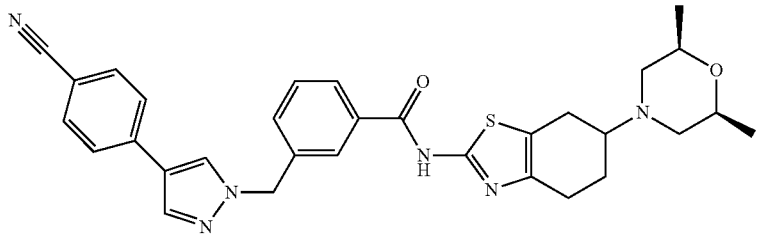
27
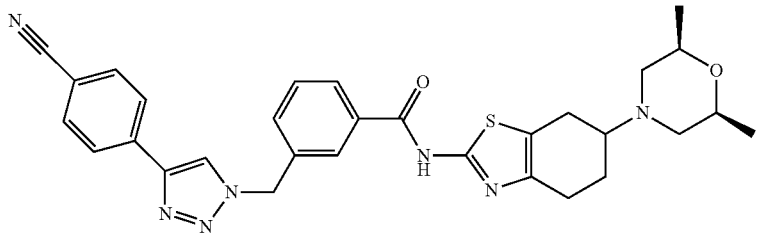
28
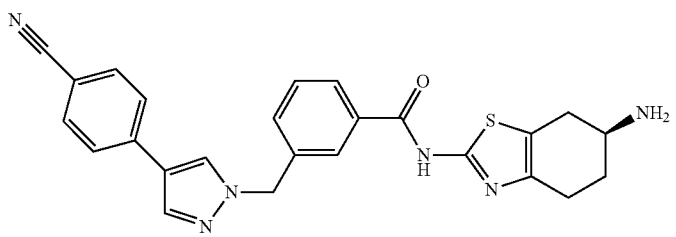
29
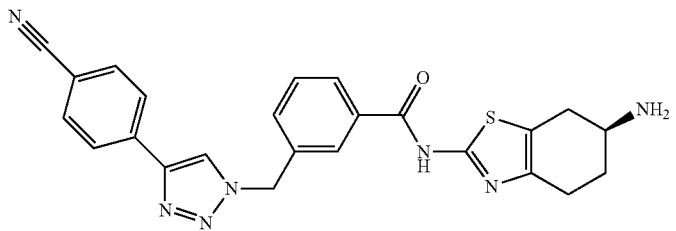
30
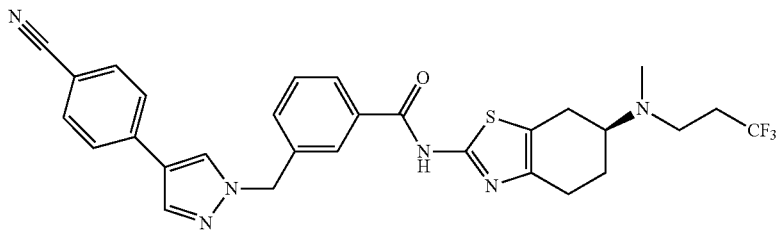

31
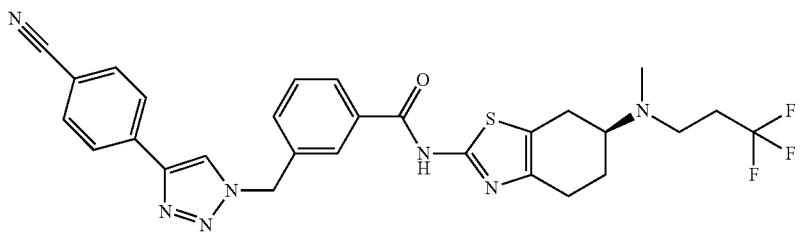
32
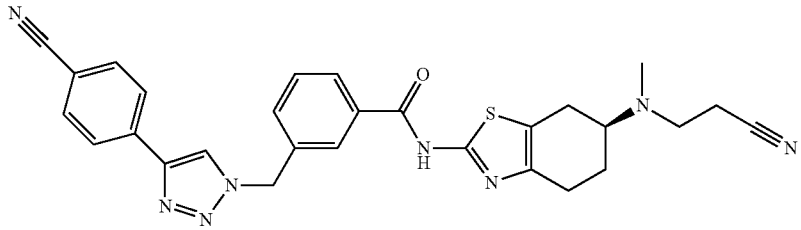
33
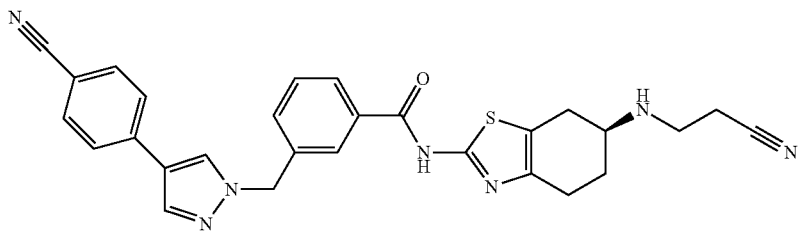
34
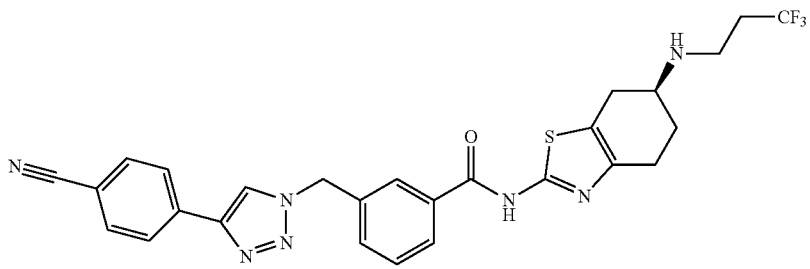
35
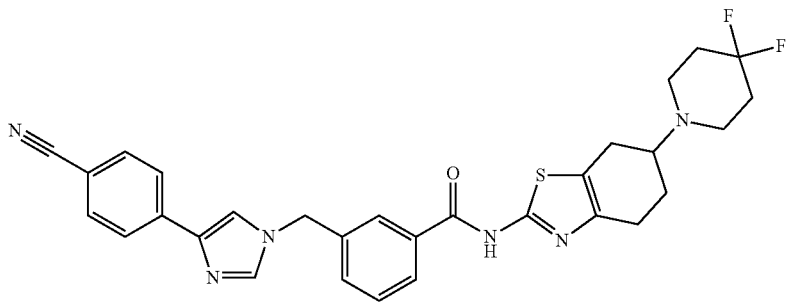
36
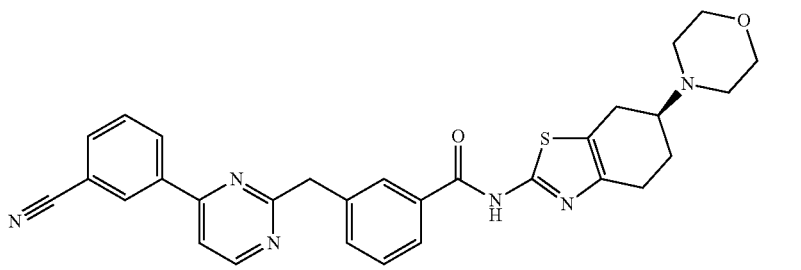

37
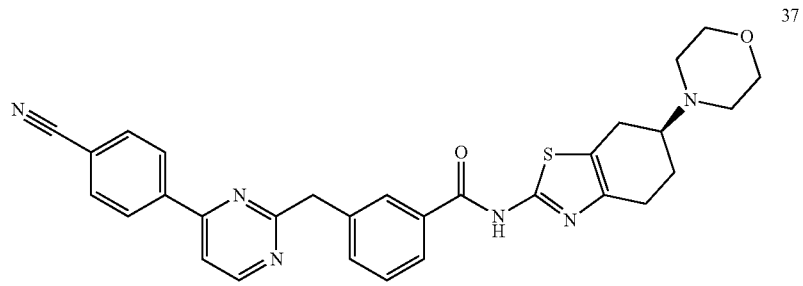
38
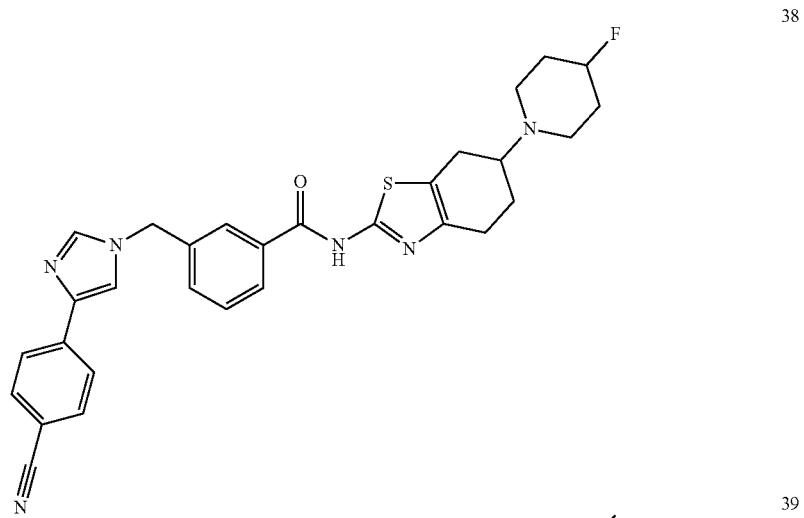
39
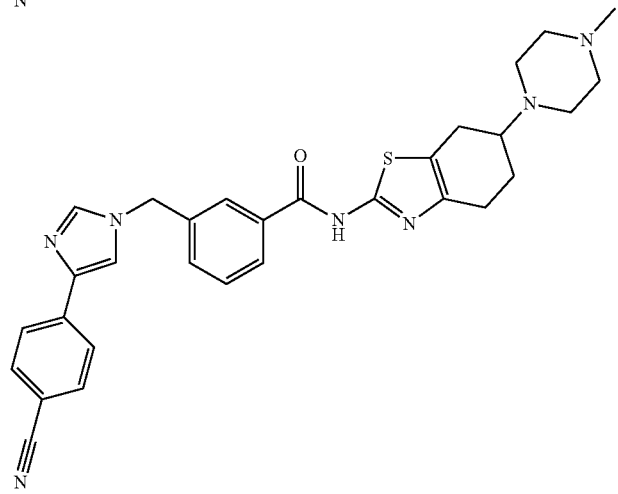
40
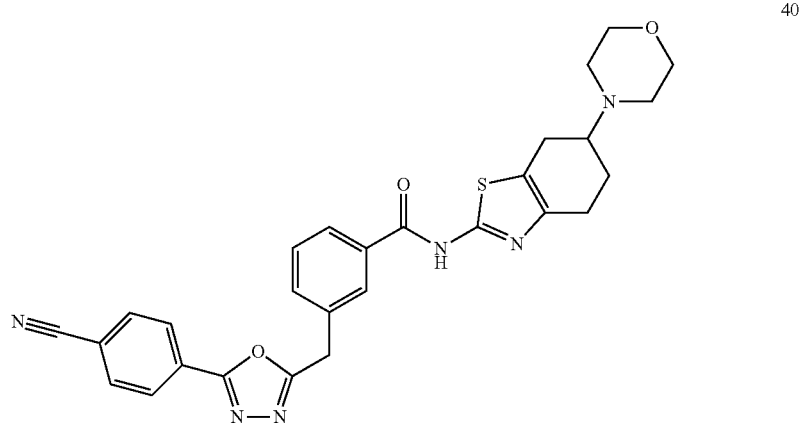

-continued
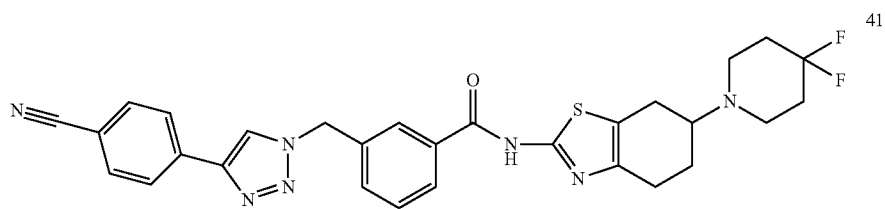
41
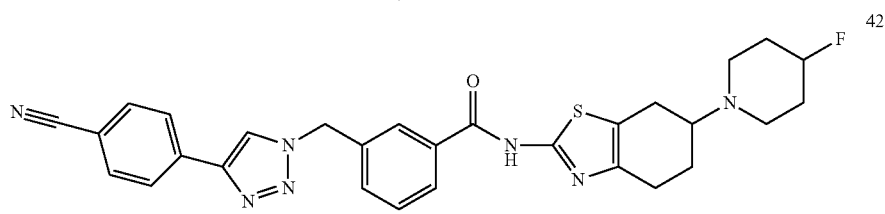
42
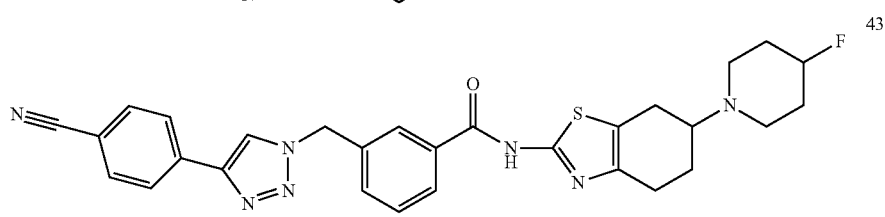
43
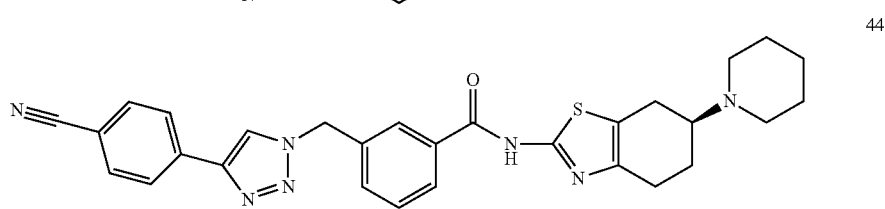
44
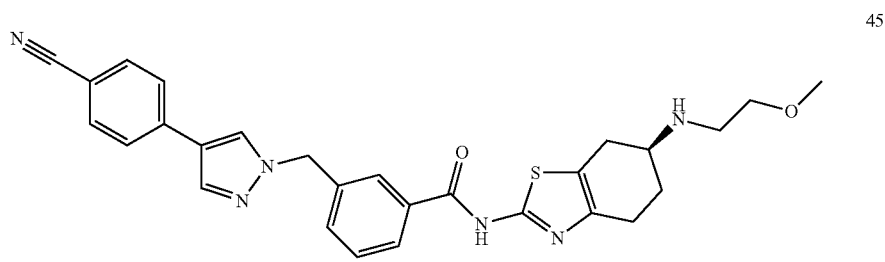
45
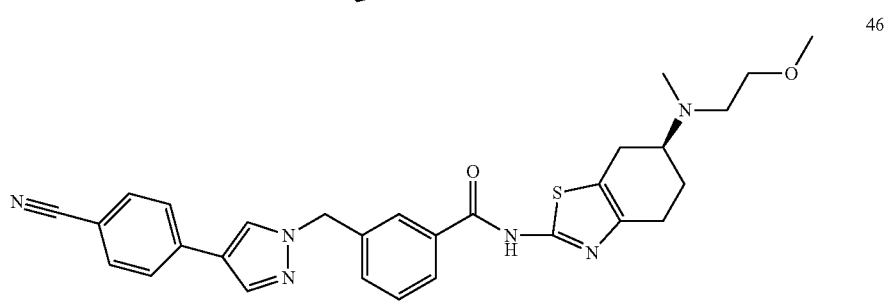
46
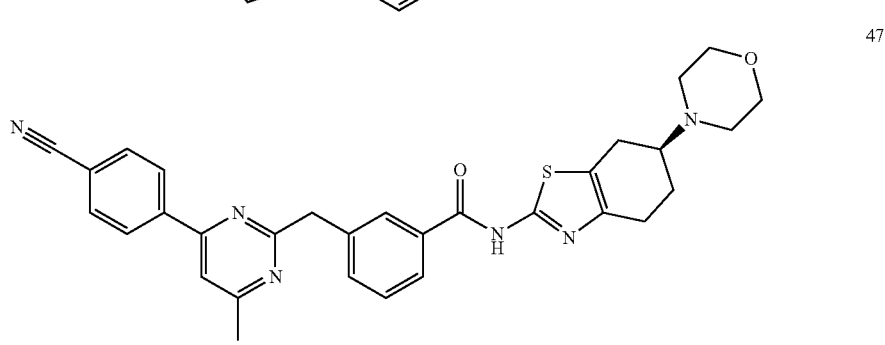
47

48
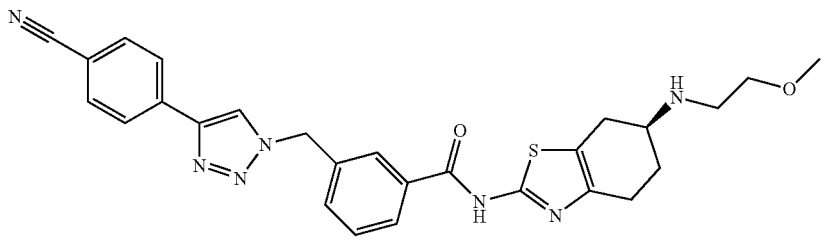
49
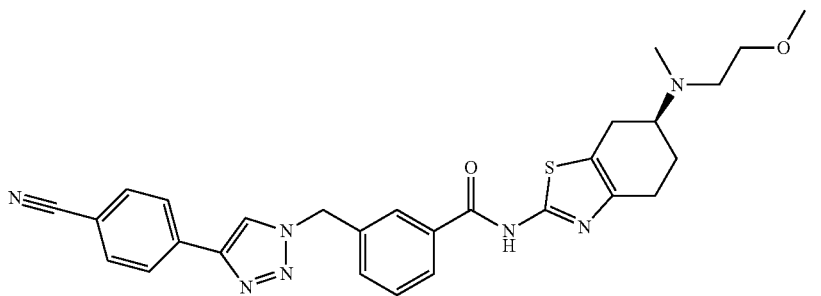
50
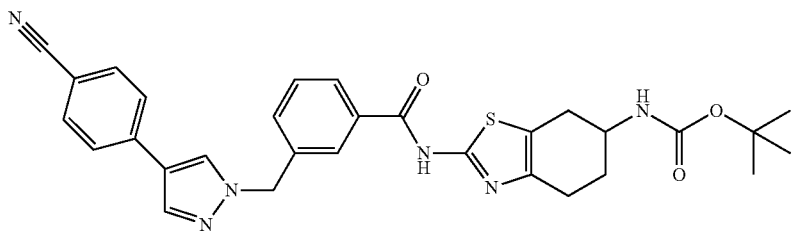
51
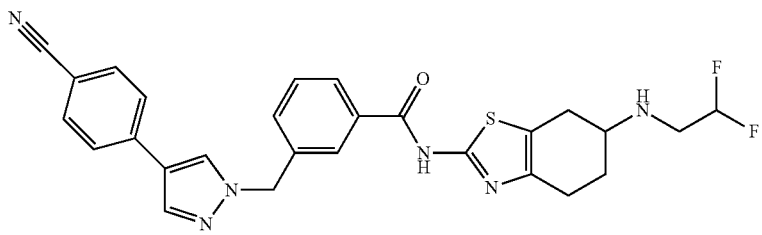
52
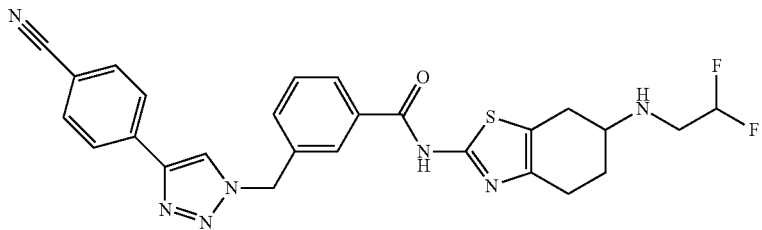
53
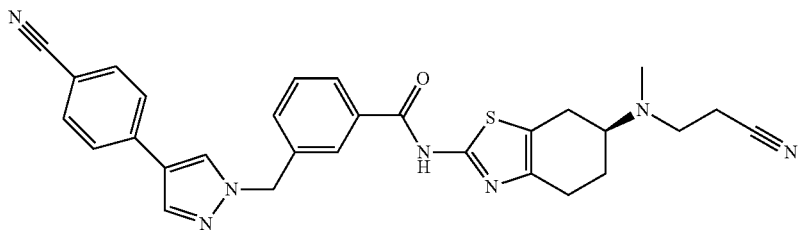

54
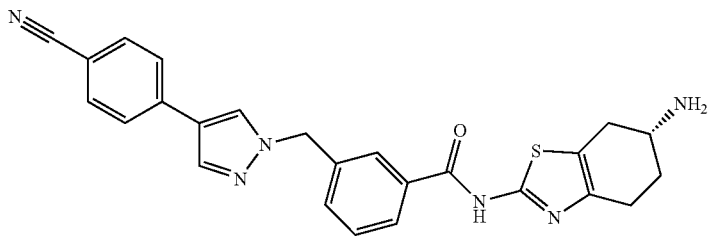
55
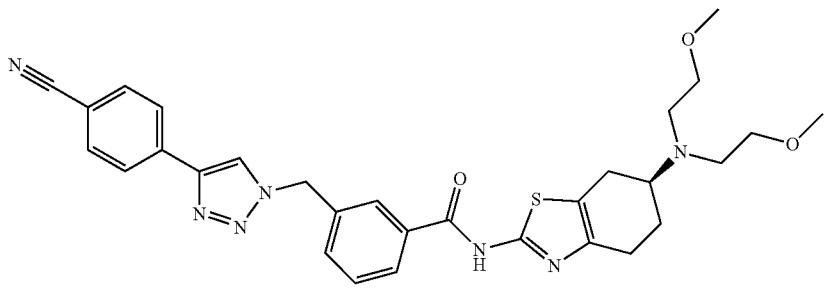
56
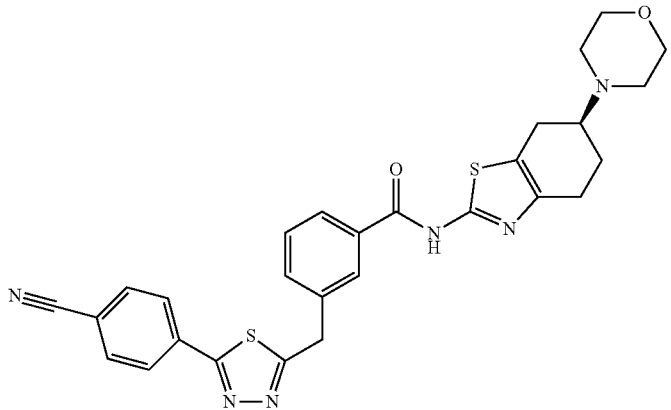
57
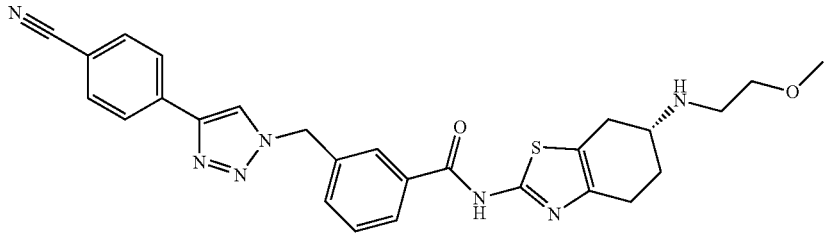
58
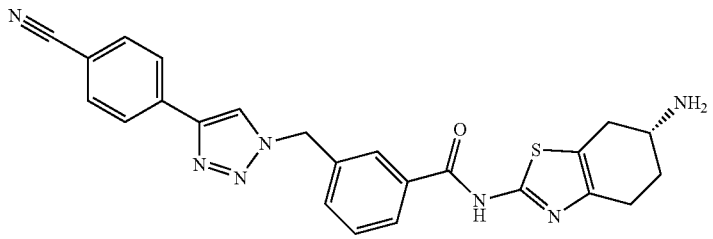

-continued
59
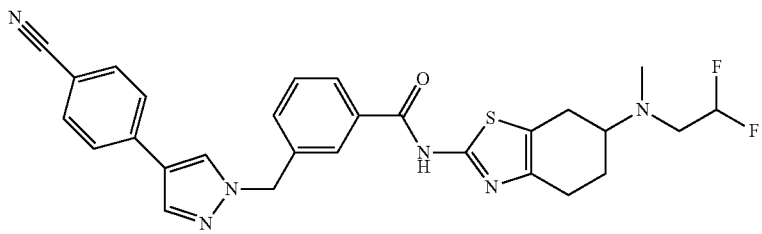
60
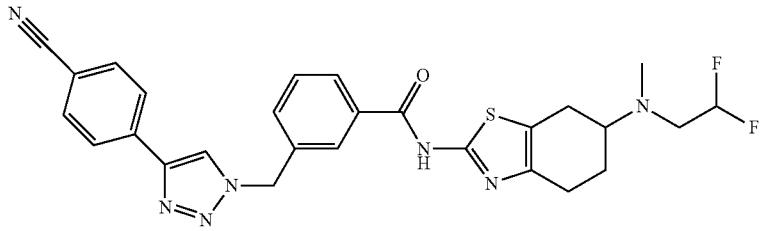
61
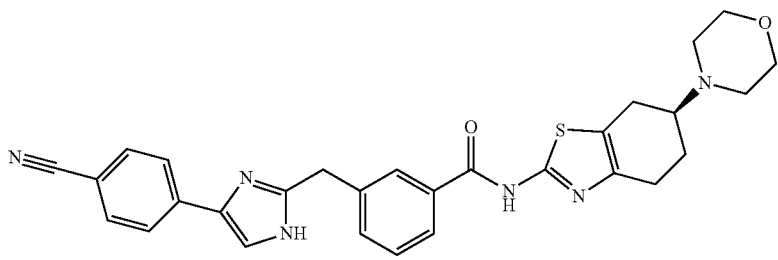
62
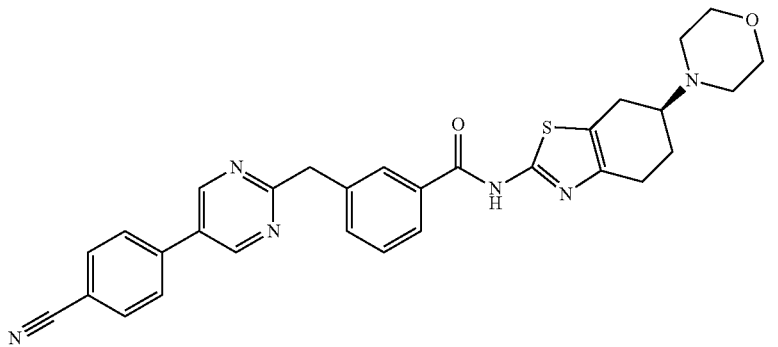
63
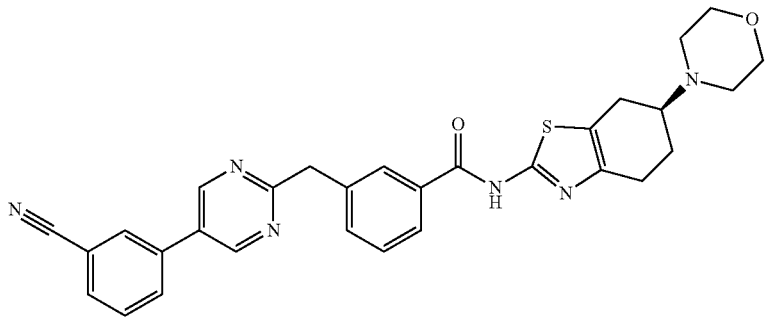

64
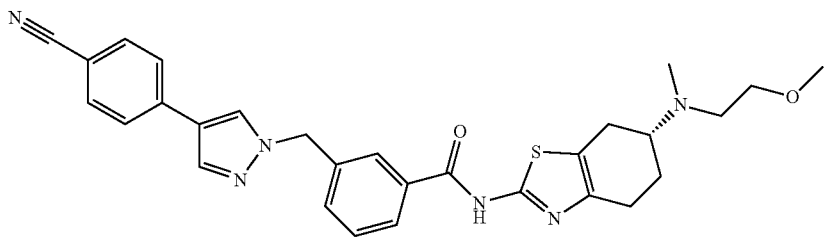
65
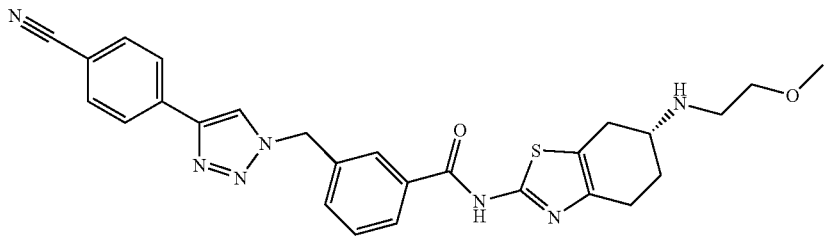
66
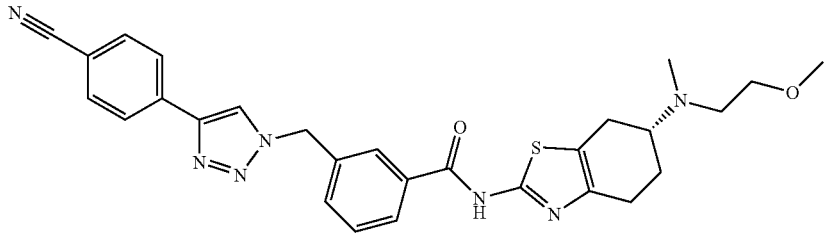
67
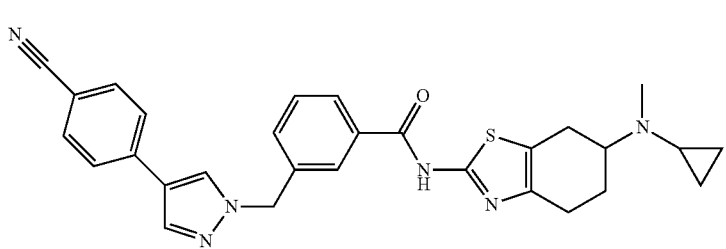
68
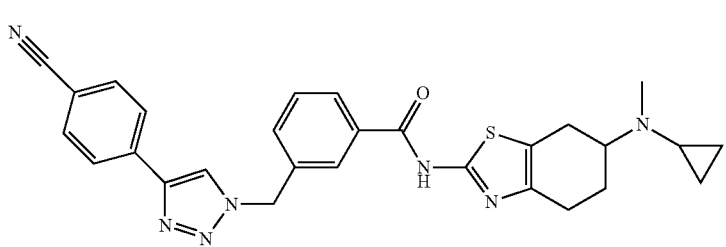
69
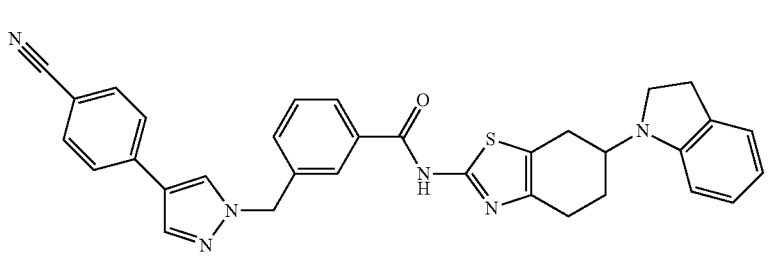

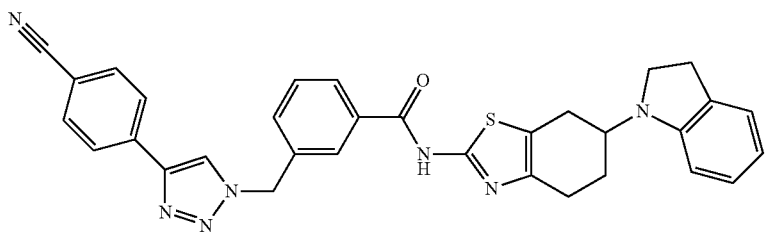
70
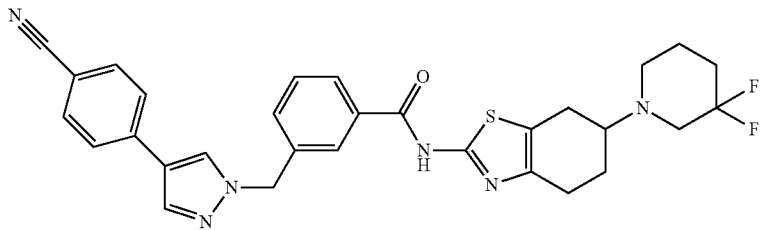
71
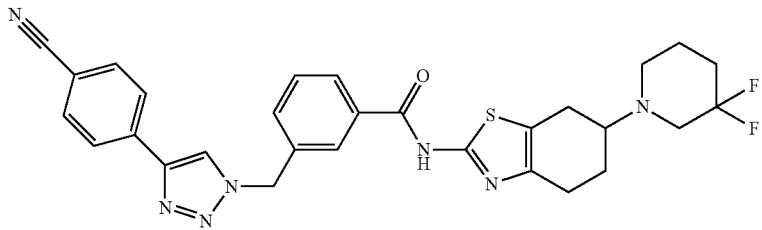
72
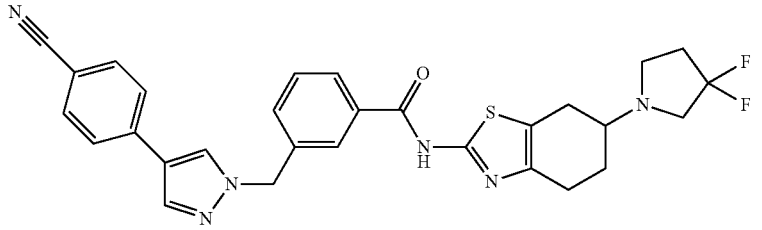
73
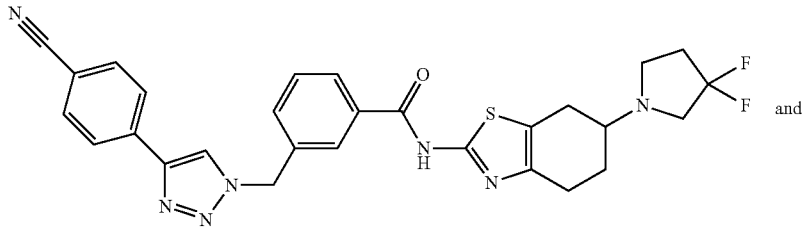
74
and
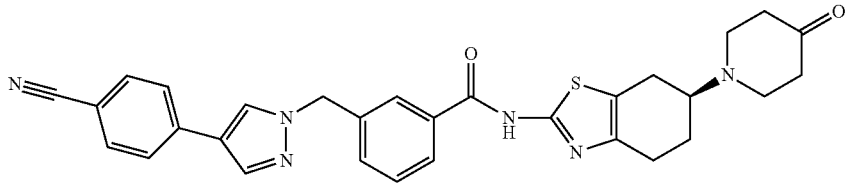
75
and the pharmaceutically acceptable salts thereof.
10. The compound of claim 9 selected from the group consisting of compound numbers 1-8, 10, 11, 13-15, 18, 20, 22-33, 36, 40-46, 48, 49, 51-53, 55-59, 64-68, 71 and 73 and the pharmaceutically acceptable salts thereof.
11. A pharmaceutical composition comprising the compound of claim 1 and a pharmaceutically acceptable excipient or carrier.
* * * * *